(12) United States Patent
Char et al.

(10) Patent No.: US 11,491,211 B2
(45) Date of Patent: *Nov. 8, 2022

(54) FORMULATIONS COMPRISING RECOMBINANT ACID ALPHA-GLUCOSIDASE

(71) Applicant: Amicus Therapeutics, Inc., Cranbury, NJ (US)

(72) Inventors: Hing Char, East Brunswick, NJ (US); Sergey Tesler, Monroe, NJ (US); Wendy Sunderland, Doylestown, PA (US); Enrique Diloné, Basking Ridge, NJ (US); Russell Gotschall, Doylestown, PA (US); Hung Do, New Hope, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/654,521

(22) Filed: Oct. 16, 2019

(65) Prior Publication Data

US 2020/0171133 A1    Jun. 4, 2020

Related U.S. Application Data

(63) Continuation of application No. 15/473,999, filed on Mar. 30, 2017, now Pat. No. 10,512,676.

(60) Provisional application No. 62/457,588, filed on Feb. 10, 2017, provisional application No. 62/315,436, filed on Mar. 30, 2016.

(51) Int. Cl.
| | | |
|---|---|---|
| *A61K 38/47* | (2006.01) | |
| *C12N 9/26* | (2006.01) | |
| *A61K 9/00* | (2006.01) | |
| *A61K 9/19* | (2006.01) | |
| *A61K 47/02* | (2006.01) | |
| *A61K 47/12* | (2006.01) | |
| *A61K 47/26* | (2006.01) | |

(52) U.S. Cl.
CPC ............ *A61K 38/47* (2013.01); *A61K 9/0095* (2013.01); *A61K 9/19* (2013.01); *A61K 47/02* (2013.01); *A61K 47/12* (2013.01); *A61K 47/26* (2013.01); *C12N 9/2408* (2013.01); *C12Y 302/0102* (2013.01)

(58) Field of Classification Search
CPC ........ C12N 9/2408; A61K 9/19; A61K 47/02; A61K 47/26; A61K 9/08; C12Y 302/0102; A61P 43/00; A61P 3/00
See application file for complete search history.

(56) References Cited

U.S. PATENT DOCUMENTS

| | | |
|---|---|---|
| 4,837,237 A | 6/1989 | Rohrschneider et al. |
| 4,985,445 A | 1/1991 | Tsuruoka et al. |
| 5,011,829 A | 4/1991 | Hirsch et al. |
| 5,103,008 A | 4/1992 | Scudder et al. |
| 5,236,838 A | 8/1993 | Rasmussen et al. |
| 5,399,567 A | 3/1995 | Platt et al. |
| 5,472,969 A | 12/1995 | Platt et al. |
| 5,580,757 A | 12/1996 | Desnick et al. |
| 5,786,369 A | 7/1998 | Platt et al. |
| 5,801,185 A | 9/1998 | Platt et al. |
| 5,879,680 A | 3/1999 | Ginns et al. |
| 6,083,725 A | 7/2000 | Selden et al. |
| 6,118,045 A | 9/2000 | Reuser et al. |
| 6,210,666 B1 | 4/2001 | Miyamura |
| 6,225,325 B1 | 5/2001 | Jacob |
| 6,274,597 B1 | 8/2001 | Fan et al. |
| 6,395,884 B1 | 5/2002 | Selden et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,465,488 B1 | 10/2002 | Butters et al. |
| 6,534,300 B1 | 3/2003 | Canfield |
| 6,537,785 B1 | 3/2003 | Canfield |

(Continued)

FOREIGN PATENT DOCUMENTS

| | | |
|---|---|---|
| EP | 1137762 B1 | 10/2008 |
| EP | 2020438 A1 | 2/2009 |

(Continued)

OTHER PUBLICATIONS

Amalfitano et al., "Recombinant human acid α-glucosidase enzyme therapy for infantile glycogen storage disease type II: Results of a phase I/II clinical trial," Genetics in Medicine 3(2): 132-138 (2001).
Asano, N. et al. (1994) "Nitrogen-in-the-ring pyranoses and furanoses: structural basis of inhibition of mammalian glycosidases" *J Med Chem*, 37:3701-3706.
Banati, M. et al. (2011) "Enzyme replacement therapy induces T-cell responses in late-onset Pompe disease" *Muscle Nerve*, 44(5):720-726.

(Continued)

*Primary Examiner* — Iqbal H Chowdhury
(74) *Attorney, Agent, or Firm* — Servilla Whitney LLC

(57) ABSTRACT

Provided are pharmaceutical formulations comprising a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa; at least one buffer selected from the group consisting of a citrate, a phosphate and combinations thereof; and at least one excipient selected from the group consisting of mannitol, polysorbate 80, and combinations thereof, wherein the formulation has a pH of from about 5.0 to about 7.0. Also provided are methods of treating Pompe disease using these pharmaceutical formulations.

23 Claims, 39 Drawing Sheets

Specification includes a Sequence Listing.

(56) References Cited

U.S. PATENT DOCUMENTS

| | | |
|---|---|---|
| 6,545,021 B1 | 4/2003 | Mueller et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,696,059 B2 | 2/2004 | Jacob et al. |
| 6,916,829 B2 | 7/2005 | Fan et al. |
| 7,141,582 B2 | 11/2006 | Fan et al. |
| 7,351,410 B2 | 4/2008 | van Bree et al. |
| 7,371,366 B2 | 5/2008 | Canfield |
| 7,396,811 B2 | 7/2008 | LeBowitz et al. |
| 7,560,424 B2 | 7/2009 | LeBowitz et al. |
| 7,655,226 B2 | 2/2010 | Van Bree et al. |
| 7,658,916 B2 | 2/2010 | Zhu et al. |
| 7,785,856 B2 | 8/2010 | LeBowitz et al. |
| 7,858,576 B2 | 12/2010 | LeBowitz et al. |
| 7,910,545 B2 | 3/2011 | Meeker et al. |
| 7,981,864 B2 | 7/2011 | LeBowitz |
| 8,785,168 B2 | 7/2014 | LeBowitz et al. |
| 8,900,552 B2 | 12/2014 | Chen |
| 8,940,766 B2 | 1/2015 | Boyd et al. |
| 9,056,101 B2 | 6/2015 | Lockhart et al. |
| 9,181,184 B2 | 11/2015 | Mugrage et al. |
| 9,186,420 B2 | 11/2015 | Koeberl |
| 9,303,249 B2 | 6/2016 | Valenzano et al. |
| 9,404,100 B2 | 8/2016 | Valenzano et al. |
| 10,227,577 B2 * | 3/2019 | Do ............................ A61P 3/08 |
| 10,512,676 B2 * | 12/2019 | Char ...................... A61K 9/0095 |
| 10,857,212 B2 * | 12/2020 | Do ........................ A61P 3/00 |
| 2002/0049233 A1 | 4/2002 | Kararli et al. |
| 2002/0073438 A1 | 6/2002 | Reuser et al. |
| 2002/0095135 A1 | 7/2002 | Meeker et al. |
| 2002/0137125 A1 | 9/2002 | Zhu |
| 2004/0180419 A1 | 9/2004 | Fan |
| 2004/0204379 A1 | 10/2004 | Cheng et al. |
| 2005/0058634 A1 | 3/2005 | Zhu |
| 2005/0244400 A1 | 11/2005 | LeBowitz et al. |
| 2006/0121018 A1 | 6/2006 | LeBowitz |
| 2006/0264467 A1 | 11/2006 | Mugrage et al. |
| 2007/0178081 A1 | 8/2007 | Fan |
| 2009/0117091 A1 | 5/2009 | LeBowitz et al. |
| 2009/0203575 A1 | 8/2009 | LeBowitz et al. |
| 2010/0119502 A1 | 5/2010 | Do et al. |
| 2010/0260740 A1 | 10/2010 | Boyd et al. |
| 2010/0266571 A1 | 10/2010 | Lockhart et al. |
| 2011/0136151 A1 | 6/2011 | Wustman et al. |
| 2011/0189710 A1 | 8/2011 | Wustman et al. |
| 2011/0268721 A1 | 11/2011 | Do et al. |
| 2011/0300120 A1 | 12/2011 | Avila et al. |
| 2012/0148556 A1 | 6/2012 | LeBowitz et al. |
| 2015/0044194 A1 | 2/2015 | Valenzano et al. |
| 2015/0086530 A1 | 3/2015 | Greene et al. |
| 2015/0147309 A1 | 5/2015 | Parenti et al. |
| 2015/0258081 A1 | 9/2015 | Lukas et al. |
| 2016/0184410 A1 | 6/2016 | Chen |
| 2016/0243203 A1 | 8/2016 | van Bree et al. |
| 2017/0056483 A1 | 3/2017 | Valenzano et al. |
| 2017/0298335 A1 | 10/2017 | Gotschall et al. |
| 2017/0335301 A1 | 11/2017 | Do et al. |

FOREIGN PATENT DOCUMENTS

| | | |
|---|---|---|
| FR | 2861991 A1 | 5/2005 |
| JP | 2005-523882 A | 8/2005 |
| JP | 2008-525457 A | 7/2008 |
| JP | 2008-545657 A | 12/2008 |
| JP | 2010-525084 A | 7/2010 |
| JP | 2011-512876 A | 4/2011 |
| WO | WO 00/034451 A1 | 6/2000 |
| WO | WO 01/019955 A2 | 3/2001 |
| WO | WO 03/032907 A2 | 4/2003 |
| WO | WO 2004/069190 A2 | 8/2004 |
| WO | WO 2005/077093 A2 | 8/2005 |
| WO | WO 2006/071613 A2 | 7/2006 |
| WO | WO 2006/125141 A2 | 11/2006 |
| WO | WO 2008/112525 A2 | 9/2008 |
| WO | WO 2008/134628 A2 | 11/2008 |
| WO | WO 2009/066069 A1 | 5/2009 |
| WO | WO 2009/114679 A2 | 9/2009 |
| WO | WO 2010/015816 A2 | 2/2010 |
| WO | WO 2010/148253 A2 | 12/2010 |
| WO | WO 2011/109600 A1 | 9/2011 |
| WO | WO 2012/145644 A1 | 10/2012 |
| WO | WO 2013/013017 A2 | 1/2013 |
| WO | WO 2013/091897 | 6/2013 |
| WO | WO 2016/054231 A1 | 4/2016 |

OTHER PUBLICATIONS

Barton, N.W. et al. (1991) "Replacement Therapy for Inherited Enzyme Deficiency—Macrophage-Targeted Glucocerebrosidase for Gaucher's Disease" *N Eng J Med*, 324:1464-1470.

Beck, M. (Sep. 2009) "Alglucosidase alfa: Long term use in the treatment of patients with Pompe disease" *Therapeutics and Clinical Risk Management*, 5:767-772.

Butters, T.D. et al. (2005) "Imino Sugar Inhibitors for Treating the Lysosomal Glycosphingolipidoses" *Glycobiology*, 15(10):43E-52R.

Courageot, M-P. et al. (2000) "α-Glucosidase inhibitors reduce dengue virus production by affecting the initial steps of virion morphogenesis in the endoplasmic reticulum" *J Virol*, 74:564-572.

Cox, T. et al. (2000) "Novel oral treatment of Gaucher's disease with N-butyldeoxynojirimycin (OGT 918) to decrease substrate biosynthesis" *The Lancet*, 355:1481-1485.

Dale, M.P. et al. (1985) "Reversible inhibitors of δ-glucosidase" *Biochemistry*, 24:3530-3539.

Database Score. SEQ ID No. 1 sequence in WO 2012145644 A1. Retrieved from: http://score.uspto.gov/ScoreAccessWeb/viewSeqldResult.htm, pp. 1-3; accessed Jan. 22, 2018, 3 pages.

Do, H. (Feb. 13, 2014) "Chemical Conjugation of Targeting Peptide to ERTs Improve Receptor Binding and Substrate Clearance in Mouse Models of Disease" Amicus Technologies: Presentation from the 10th Lysosomal Disease Network WORLDSymposium, San Diego, CA, Feb. 10-13, 2014; 14 pages.

Do, H. et al. (Feb. 13, 2014) "Chemical Conjugation of Targeting Peptide to ERTs Improve Receptor Binding and Substrate Clearance in Mouse Models of Disease" Amicus Technologies: Poster from the 10th Annual Lysosomal Disease Network WORLDSymposium, San Diego, CA, Feb. 10-13, 2014, Abstract #277; 1 page.

Do, H. et l. (2017) "ATB200/AT2221 Cleared Accumulated Glycogen and Reversed Cellular Dysfunction to Increase Functional Muscle Strength in Mouse Model of Pompe Disease" Amicus Technologies: Poster from the 13th Annual Lysosomal Disease Network WORLDSymposium, San Diego, CA, Feb. 13-17, 2017; Poster #74, Abstract A-348, 1 page.

Duke University Medical Center (1997) "Duke Obtains FDA Designation for Pompe Disease Therapy" Press Release, dated Sep. 2, 1997, 2 pages.

European Application No. 15845664.0, filed Apr. 6, 2017, by Amicus Therapeutics, Inc.: Supplementary European Search Report, dated Feb. 12, 2018, 13 pages.

Fryar, C.D. et al. (Oct. 2012) "Anthropometric Reference Data for Children and Adults: United States 2007-2010" National Center for Health Statistics. *Vital Health Stat*, Series 11, No. 252, 48 pages.

Genzyme Corporation (2010) Myozyme®. Highlights of Prescribing Information. Cambridge, MA: Genzyme Corporation, Jun. 2010, 3 pages.

Gotschall, R. (2015) "Novel rhGAA with Optimal Glycosylation Is Significantly Better than Alglucosidase Alfa for Glycogen Clearance in Skeletal Muscles of Gaa KO Mice" Amicus Technologies: Presentation from the 11th Lysosomal Disease Network WorldSymposium, Feb. 9-13, 2015, Orlando, Florida; 12 pages.

Gotschall, R. (2015) "Novel rhGAA with Optimal Glycosylation Is Significantly Better than Alglucosidase Alfa for Glycogen Clearance in Skeletal Muscles of Gaa KO Mice" Amicus Technologies: Poster from the ACMG Annual Clinical Genetics Meeting, Mar. 25-27, 2015, Salt Lake City, Utah; Abstract #739, 1 page.

Gotschall, R. et al. (2015) "Novel rhGAA with Optimal Glycosylation Is Significantly Better than Alglucosidase Alfa for Glycogen Clearance in Skeletal Muscles of Gaa KO Mice" Amicus Technologies:

(56) References Cited

OTHER PUBLICATIONS

Abstract from the 11th Lysosomal Disease Network WORLDSymposium, Feb. 9-13, 2015, Orlando, Florida. Abstract 94, 1 page.
Gotschall, R. et al. (2017) "ATB200/AT2221 Reverses Cellular Dysfunction and Increases Muscle Strength in a Pompe Disease Mouse Model" Amicus Therapeutics: Poster from the 4th International Glycogen Storage Disease (GSD) Conference, Jun. 15-17, 2017, University Medical Center, Groningen, The Netherlands; Abstract 48, 1 page.
Jeyakumar, M. et al. (1999) "Delayed symptom onset and increased life expectancy in Sandhoff disease mice treated with N-butyldeoxynojirimycin" *Proc Natl Acad Sci USA*, 96:6388-6393.
Johnson, F.K. et al. (2017) "First-in-Human Preliminary Pharmacokinetic and Safety Data on a Novel Recombinant Acid α-Glucosidase, ATB200, Co-administered With the Pharmacological Chaperone AT2221 in ERT-Experienced Patients With Pompe Disease" Amicus Technologies: Poster from the 13th Annual Lysosomal Disease Network WORLDSymposium, San Diego, CA, Feb. 13-17, 2017; Poster #LB-26, 1 page.
Khanna. R. et al. (2012) "The pharmacological chaperone AT2220 increases recombinant human acid α-glucosidase uptake and glycogen reduction in a mouse model of Pompe disease" *PLoS ONE*, 7(7):e40776, 14 pages.
Khanna, R. et al. (2014) "The pharmacological chaperone AT2220 increases the specific activity and lysosomal delivery of mutant acid alpha-glucosidase, and promotes glycogen reduction in a transgenic mouse model of Pompe disease" *PLoS One*, 9(7):e102092, 16 pages.
Khanna, R. et al. (2016) "Co-Administration of the Pharmacological Chaperone AT2221 with A Proprietary Recombinant Human Acid α-Glucosidase Leads to Greater Plasma Exposure and Substrate Reduction Compared to Alglucosidase Alfa" Amicus Therapeutics: Poster from the 12th Annual Lysosomal Disease Network WORLDSymposium Meeting, Feb. 29-Mar. 4, 2016, San Diego, California; 1 page.
Kishnani, P. et al. (2017) "Duvoglustat HCl Increases Systemic and Tissue Exposure of Active Acid α-Glucosidase in Pompe Patients Co-administered with Alglucosidase α" *Molecular Therapy*, 25(5):1199-1208.
Klinge, L. et al. (2005) "Enzyme replacement therapy in classical infantile Pompe disease: results of a ten-month follow-up study" *Neuropediatrics*, 36(1):6-11.
Legler, G. and S. Pohl (1986) "Synthesis of 5-amino-5-deoxy-D-galactopyranose and 1,5-dideoxy-1,5-imino-D-galactitol, and their inhibition of alpha- and beta-D-galactosidases" *Carbohydrate Res*, 155:119-129.
Lembcke, B. et al. (1991) "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)" *Res Exp Med*, 191(6): 389-404.
Lun, Y. et al. (2015) "Histological examination of the effect of a highly phosphorylated proprietary recombinant human acid alpha-glucosidase on glycogen reduction in disease-relevant muscles of Pompe mice" Amicus Technologies: Poster from the Lysosomal Disease Network 11th WORLDSymposium, Feb. 9-13, 2015, Orlando, Florida; 1 page.
Lun, Y. et al. (2017) "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice" Amicus Technologies: Poster from the 13th Annual Lysosomal Disease Network WORLDSymposium, San Diego, CA, Feb. 13-17, 2017; 1 page.
Lun, Y. et al. (2017) "Stabilized Next-Generation Recombinant Human Acid Alpha-Glucosidase ATB200 Clears Accumulated Glycogen and Reverses Cellular Dysfunction to Increase Muscle Strength in A Mouse Model of Pompe Disease" Amicus Therapeutics: Poster from the 2017 Muscular Dystrophy Association Scientific Conference, Mar. 19-11, 2017, Arlington, Virginia; 1 page.

Martiniuk et al., "Correction of Glycogen Storage Disease Type II by Enzyme Replacement with a Recombinant Human Acid Maltase Produced by Over-Expression in a CHO-HDFR$^{neg}$ Cell Line," Biochemical and Biophysical Research Communications, 276(3):917-923 (2000).
Mellor, H.R. et al. (2004) "Cellular effects of deoxynojirimycin analogues; uptake, retention and inhibition of glycosphingolipid biosynthesis" *Biochem J*, 381:861-866.
McVie-Wylie, et al., "Biochemical and pharmacological characterization of different recombinant acid α-glucosidase preparations evaluated for the treatment of Pompe disease," Molecular Genetics and Metabolism, 94: 448-455 (2008).
National Institutes of Health Clinical Center (2002) *Patient Education Materials: Giving a subcutaneous injection*. Bethesda, MD: NIH Clinical Center, 3 pages.
Okumiya et al., Chemical chaperones improve transport and enhance stability of mutant α-glucosidases in glycogen storage disease type II. Mol. Genet. Metab. 90: 49-57 (2007).
Parenti et al., A Chaperone Enhances Blood α-Glucosidase Activity in Pompe Disease Patients Treated with Enzyme Replacement Therapy. Mol. Ther. 22(11):2004-2012 (2014).
Parenti, G. et al. (2005) "Alpha-Glucosidase Enhancement in Fibroblasts from Patients with Pompe Disease" *J Inherit Metab Dis*, 28(Suppl. 1):193, Abstract 383-P.
PCT International Search Report and Written Opinion dated May 8, 2013, in PCT/US2013/029660, 8 pages.
PCT International Search Report and Written Opinion dated Oct. 1, 2013, in PCT/US2013/039215, 9 pages.
PCT International Search Report and Written Opinion dated Jan. 6, 2016, in PCT/US2015/053252, 9 pages.
PCT International Search Report and Written Opinion dated Mar. 7, 2017, in PCT/US2016/069243, 10 pages.
Platt, F.M. et al. (1997) "Prevention of Lysosomal Storage in Tay-Sachs Mice Treated with N-butyldeoxynojirimycin" *Science*, 276:428-431.
Porto, C. et al. (2009) "The Pharmacological Chaperone N-butyldeoxynojirimycin Enhances Enzyme Replacement Therapy in Pompe Disease Fibroblasts" *Mol Ther*, 17(6):964-971.
Raben, N. et al. (2005) "Replacing acid alpha-glucosidase in Pompe disease: recombinant and transgenic enzymes are equipotent, but neither completely clears glycogen from type II muscle fibers" *Mol Ther*, 11(1):48-56.
Ruvinov, S.B. et al. (1995) "Monovalent Cations Partially Repair a Conformational Defect in a Mutant Tryptophan Synthase $\alpha_2 \beta_2$ Complex (β-E109A)" *J Bio Chem*, 270: 17333-17338.
Sathe, S. et al. (2017) "Preliminary Pharmacokinetic and Safety Data in Patients With Pompe Disease in First-in-Human Study Receiving ATB200/AT2221" Amicus Therapeutics: Poster from the 2017 Muscular Dystrophy Association Scientific Conference, Mar. 19-11, 2017, Arlington, Virginia; 1 page.
Sathe, S. et al. (2017) "Preliminary Safety, Pharmacokinetic, Pharmacodynamic, and Efficacy Data in Patients With Pompe Disease Receiving ATB200/AT2221 in First-in-Human Study" Amicus Therapeutics: Poster from the 4th International Glycogen Storage Disease (GSD) Conference, Jun. 15-17, 2017, University Medical Center, Groningen, The Netherlands; 1 page.
U.S. Appl. No. 14/379,131: Non-Final Office Action, dated Sep. 15, 2015, 13 pages.
Valenzano, K.J. et al. (Jun. 2011) "Identification and characterization of pharmacological chaperones to correct enzyme deficiencies in lysosomal storage disorders" *Assay and Drug Development Technologies*, 9(3):213-235.
Van Der Ploeg, A.T. et al. (1988) "Receptor-Mediated Uptake of Acid α-Glucosidase Corrects Lysosomal Glycogen Storage in Cultured Skeletal Muscle" *Pediatric Research*, 24(1):90-94.
Van Hove, J.L.K. et al. (1996) "High-level production of recombinant human lysosomal acid α-glucosidase in Chinese hamster ovary cells which targets to heart muscle and corrects glycogen accumulation in fibroblasts from patients with Pompe disease" *Proc Natl Acad Sci USA*, 93:65-70.
Van Hove, J.L.K. et al. (1997) "Purification of recombinant human precursor acid α-glucosidase" *Biochem Mol Biol Int*, 43(3):613-623.

(56) References Cited

OTHER PUBLICATIONS

Wilson, B.A. et al. (2003) *Prentice Hall Nurse's Drug Guide 2003 Companion Website*. [online]. Retrieved from: http://wps.prenhall.com/chet_wilson_drugguides_1_/6/1576/403472.cw/index.html; accessed Sep. 30, 2014.

Shin-Buehring, Y.S. et al. (1978) "Separation of acid and neutral α-glucosidase isoenzymes from fetal and adult tissues, cultivated fibroblasts and amniotic fluid cells by DEAE-cellulose and Sephadex G-100 column chromatography" *Clinica Chimica Acta* 89(3):393-404, 12 pages.

Hermans et al., "Human lysosomal α-glucosidase: functional characterization of the glycosylation sites," Biochem J., 1993, 289:681-686.

Khanna R. et al., Molecular Genetics and Metabolism, vol. 117, Issue 2, Feb. 2016, pp. S66-S67. doi:10.1016/j.ymgme.2015.12.318).

\* cited by examiner

Structure and Receptor Affinity for High Mannose and Phosphorylated Oligosaccharides

Non-phosphorylated High Mannose N-glycan:

Mono-M6P N-glycan: Lower affinity for CI-MPR ($K_n \sim 7000$ nM)

Bis-M6P N-glycan: High Affinity for CI-MPR ($K_n = 2$ nM)

Distribution of N-Glycans on mGAA Preparations

| | Lumizyme | BP-mGAA* | ATB200 1 | ATB200 2 |
|---|---|---|---|---|
| Complex Type N-Glycans | 70.7% | 48.9% | 51.0% | 47.5% |
| Hybrid Type N-Glycans | 6.7% | 9.7% | 4.4% | 3.7% |
| High Mannose Type N-Glycans: | | | | |
| Non-phosphorylated | 15.6% | 23.7% | 14.0% | 9.9% |
| Mono-M6P | 5.2% | 10.4% | 13.4% | 14.2% |
| Bis-M6P | 1.6% | 6.8% | 17.2% | 24.7% |

FIG. 8

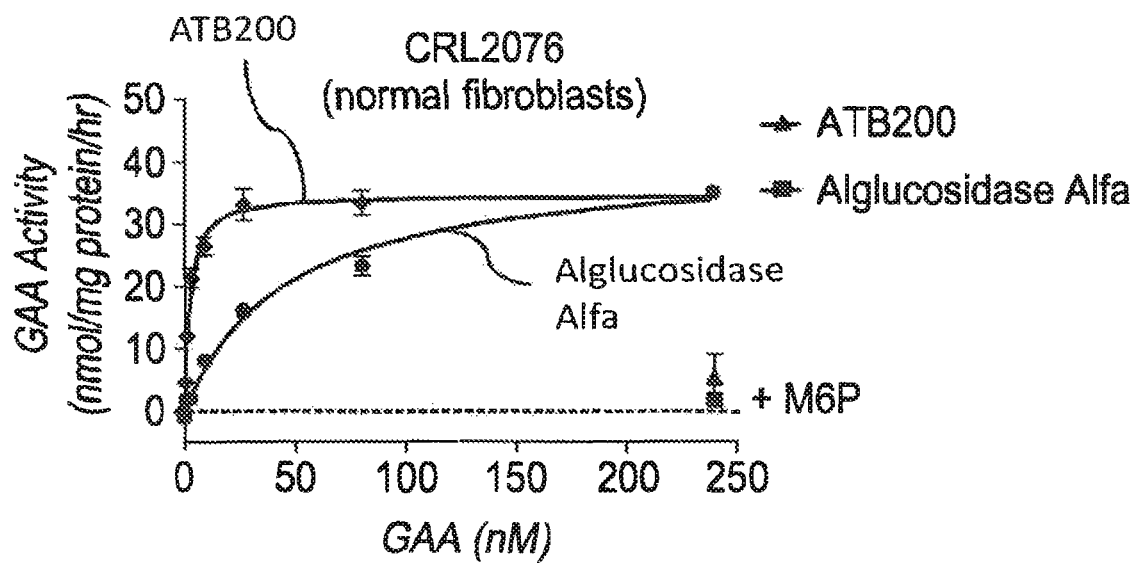
FIG. 11A
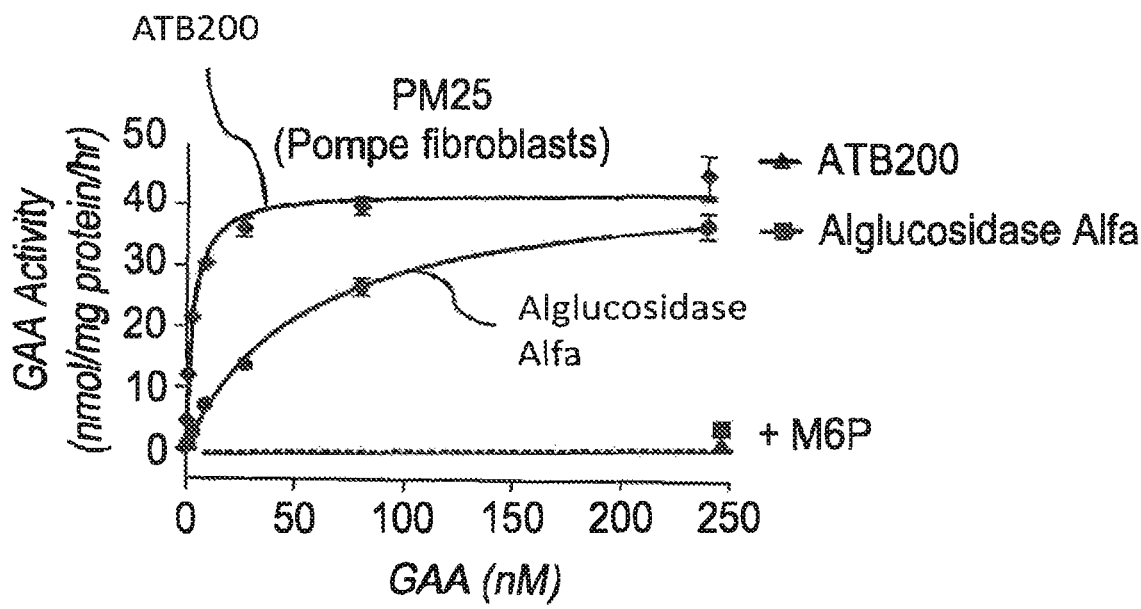
FIG. 11B
| Cell Line | $K_{uptake}$ (nM) | |
|---|---|---|
| | ATB200 | Lumizyme |
| normal | 2 | 56 |
| Pompe | 3 | 57 |
FIG. 11C

| Comparison of % glycogen reduction in *Gaa* KO mice after Lumizyme or ATB200 administration (with or without miglustat) | | |
|---|---|---|
| Enzyme ± Chaperone | Quadriceps | Triceps |
| Lumizyme alone (20 mg/kg) | 14 | 14 |
| ATB200 alone (20 mg/kg) | 74 | 62 |
| ATB200 + Miglustat (20 mg/kg) + (10 mg/kg) | 94 | 73 |

FORMULATIONS COMPRISING RECOMBINANT ACID ALPHA-GLUCOSIDASE

CROSS-REFERENCE TO RELATED APPLICATIONS

This application is a continuation of U.S. patent application Ser. No. 15/473,999, filed Mar. 30, 2017 and issued as U.S. Pat. No. 10,512,676, which claims the benefit under 35 U.S.C. § 119(e) to U.S. Provisional Application No. 62/315,436, filed Mar. 30, 2016, and U.S. Provisional Application No. 62/457,588, filed Feb. 10, 2017, the entire contents of each of which are incorporated herein by reference in their entirety.

SEQUENCE LISTING

The sequence listing of the present application has been submitted electronically via EFS-Web as an ASCII formatted sequence listing with a file name 14322_0009_01_SL.txt, creation date of Oct. 16, 2019, and a size of 16,155 bytes. The sequence listing is part of the specification and is herein incorporated by reference in its entirety.

TECHNICAL FIELD

Principles and embodiments of the present invention relate generally to formulations comprising recombinant acid α-Glucosidase, and particularly liquid formulations.

BACKGROUND

Pompe disease, also known as acid maltase deficiency or glycogen storage disease type II, is one of several lysosomal storage disorders. Lysosomal storage disorders are a group of autosomal recessive genetic diseases characterized by the accumulation of cellular glycosphingolipids, glycogen, or mucopolysaccharides within intracellular compartments called lysosomes. Individuals with these diseases carry mutant genes coding for enzymes which are defective in catalyzing the hydrolysis of one or more of these substances, which then build up in the lysosomes. Other examples of lysosomal disorders include Gaucher disease, GM1-gangliosidosis, fucosidosis, mucopolysaccharidoses, Hurler-Scheie disease, Niemann-Pick A and B diseases, and Fabry disease. Pompe disease is also classified as a neuromuscular disease or a metabolic myopathy.

Pompe disease is estimated to occur in about 1 in 40,000 births, and is caused by a mutation in the GAA gene, which codes for the enzyme lysosomal α-glucosidase (EC: 3.2.1.20), also commonly known as acid α-glucosidase. Acid α-glucosidase is involved in the metabolism of glycogen, a branched polysaccharide which is the major storage form of glucose in animals, by catalyzing its hydrolysis into glucose within the lysosomes. Because individuals with Pompe disease produce mutant, defective acid α-glucosidase which is inactive or has reduced activity, glycogen breakdown occurs slowly or not at all, and glycogen accumulates in the lysosomes of various tissues, particularly in striated muscles, leading to a broad spectrum of clinical manifestations, including progressive muscle weakness and respiratory insufficiency. Tissues such as the heart and skeletal muscles are particularly affected.

Pompe disease can vary widely in the degree of enzyme deficiency, severity and age of onset, and over 500 different mutations in the GAA gene have been identified, many of which cause disease symptoms of varying severity. The disease has been classified into broad types: early onset or infantile and late onset. Earlier onset of disease and lower enzymatic activity are generally associated with a more severe clinical course. Infantile Pompe disease is the most severe, resulting from complete or near complete acid α-glucosidase deficiency, and presents with symptoms that include severe lack of muscle tone, weakness, enlarged liver and heart, and cardiomyopathy. The tongue may become enlarged and protrude, and swallowing may become difficult. Most affected children die from respiratory or cardiac complications before the age of two. Late onset Pompe disease can present at any age older than 12 months and is characterized by a lack of cardiac involvement and better short-term prognosis. Symptoms are related to progressive skeletal muscle dysfunction, and involve generalized muscle weakness and wasting of respiratory muscles in the trunk, proximal lower limbs, and diaphragm. Some adult patients are devoid of major symptoms or motor limitations. Prognosis generally depends on the extent of respiratory muscle involvement. Most subjects with Pompe disease eventually progress to physical debilitation requiring the use of a wheelchair and assisted ventilation, with premature death often occurring due to respiratory failure.

Recent treatment options for Pompe disease include enzyme replacement therapy (ERT) with recombinant human acid α-glucosidase (rhGAA). Conventional rhGAA products are known under the names alglucosidase alfa, Myozyme® or Lumizyme® from Genzyme, Inc. ERT is a chronic treatment required throughout the lifetime of the patient, and involves administering the replacement enzyme by intravenous infusion. The replacement enzyme is then transported in the circulation and enters lysosomes within cells, where it acts to break down the accumulated glycogen, compensating for the deficient activity of the endogenous defective mutant enzyme, and thus relieving the disease symptoms.

The way in which replacement enzymes, such as rhGAA, are prepared, stored, transported and administered to patients is difficult. The enzymes used in ERT are generally relatively complex and delicate, making selection of accompanying buffers, excipients, etc. critical. If the enzyme is not preserved properly, then high quantities may be required, making treatment costly and inefficient.

Some conventional rhGAA products are provided to patients as a lyophilized (freeze-dried) powder in single-use vials without preservatives. The rhGAA must then be reconstituted in the vials, then diluted and administered intravenously. While lyophilization helps to preserve the enzyme after manufacture until it is ready to be administered to a patient, this process in and of itself can damage enzyme. Thus, great care must be taken in selection of the components in the rhGAA formulation so that they help preserve protein concentration and activity.

Furthermore, recombinant enzymes are often structurally different from wild-type enzymes. Even if the amino acids in the recombinant enzyme may be identical to its wild-type counterpart, there may be differences in the carbohydrate chemistry. Thus, as new recombinant enzymes are discovered, the formulations for the enzymes must be developed specific the chemistry of the newly discovered enzymes.

Accordingly, there is an ongoing need for formulations to store and transport recombinant enzymes, such as rhGAA, which preserve enzyme activity and concentration.

SUMMARY

One aspect of the invention pertains to a pharmaceutical formulation. In embodiment one, the formulation comprises:

(a) a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa;

(b) at least one buffer selected from the group consisting of a citrate, a phosphate and combinations thereof; and (c) at least one excipient selected from the group consisting of mannitol, polysorbate 80, and combinations thereof, wherein the formulation has a pH of from about 5.0 to about 7.0.

Embodiment two includes a modification to the pharmaceutical formulation of embodiment one, wherein the recombinant acid α-glucosidase is present in a concentration of about 5 to about 50 mg/mL.

Embodiment three includes a modification to the pharmaceutical formulation of embodiment one or two, wherein the recombinant acid α-glucosidase is present in a concentration of about 15 mg/mL.

Embodiment four includes a modification to the pharmaceutical formulation of any of embodiments 1-3, wherein the formulation has a pH of from about 5.5 to about 7.0.

Embodiment five includes a modification to the pharmaceutical formulation of any of embodiments 1-4, wherein the formulation has a pH of about 6.0.

Embodiment six includes a modification to the pharmaceutical formulation of any of embodiments 1-5, wherein the at least one buffer comprises citrate.

Embodiment seven includes a modification to the pharmaceutical formulation of any of embodiments 1-6, wherein the at least one buffer comprises a potassium, sodium or ammonium salt.

Embodiment eight includes a modification to the pharmaceutical formulation of any of embodiments 1-7, wherein the at least one buffer comprises sodium citrate.

Embodiment nine includes a modification to the pharmaceutical formulation of any of embodiments 1-8, wherein the at least one buffer is present in a concentration of about 10 to about 100 mM.

Embodiment ten includes a modification to the pharmaceutical formulation of any of embodiments 1-9, wherein the at least one buffer is present in a concentration of about 25 mM.

Embodiment 11 includes a modification to the pharmaceutical formulation of any of embodiments 1-10, wherein trehalose, sucrose, glycine or combinations thereof is excluded.

Embodiment 12 includes a modification to the pharmaceutical formulation of any of embodiments 1-11, wherein the at least one excipient is mannitol present in a concentration of about 10 to about 50 mg/mL.

Embodiment 13 includes a modification to the pharmaceutical formulation of any of embodiments 1-12, wherein the at least one excipient is polysorbate 80 present in a concentration of about 0.2 to about 0.5 mg/mL.

Embodiment 14 includes a modification to the pharmaceutical formulation of any of embodiments 1-13, wherein the mannitol is present at a concentration of about 20 mg/mL and the polysorbate 80 is present at a concentration of about 0.5 mg/mL.

Embodiment 15 includes a modification to the pharmaceutical formulation of any of embodiments 1-14, further comprising: (d) water.

Embodiment 16 includes a modification to the pharmaceutical formulation of any of embodiments 1-15, further comprising: (d) an alkalizing agent; and/or (e) an acidifying agent, wherein the alkalizing agent and acidifying agent are present in amounts to maintain the pharmaceutical formulation at a pH of from about 5.0 to about 6.0.

Embodiment 17 includes a modification to the pharmaceutical formulation of any of embodiments 1-16, wherein at least 30% of molecules of the recombinant human acid α-glucosidase comprise one or more N-glycan units bearing one or two mannose-6-phosphate residues.

Embodiment 18 includes a modification to the pharmaceutical formulation of any of embodiments 1-17, wherein the recombinant human acid α-glucosidase comprises on average from 0.5 to 7.0 moles of N-glycan units bearing one or two mannose-6-phosphate residues per mole of recombinant human acid α-glucosidase.

Embodiment 19 includes a modification to the pharmaceutical formulation of any of embodiments 1-18, wherein the recombinant human acid α-glucosidase comprises on average at least 3 moles of mannose-6-phosphate residues per mole of recombinant human acid α-glucosidase and at least 4 moles of sialic acid residues per mole of recombinant human acid α-glucosidase.

Embodiment 20 includes a modification to the pharmaceutical formulation of any of embodiments 1-19, wherein the recombinant human acid α-glucosidase comprises seven potential N-glycosylation sites, at least 50% of molecules of the recombinant human acid α-glucosidase comprise an N-glycan unit bearing two mannose-6-phosphate residues at the first site, at least 30% of molecules of the recombinant human acid α-glucosidase comprise an N-glycan unit bearing one mannose-6-phosphate residue at the second site, at least 30% of molecules of the recombinant human acid α-glucosidase comprise an N-glycan unit bearing two mannose-6-phosphate residue at the fourth site, and at least 20% of molecules of the recombinant human acid α-glucosidase comprise an N-glycan unit bearing one mannose-6-phosphate residue at the fourth site.

Embodiment 21 includes a modification to the pharmaceutical formulation of any of embodiments 1-20, wherein the pharmaceutical formulation consists essentially of:

(a) the recombinant acid α-glucosidase;

(b1) sodium citrate;

(b2) citric acid monohydrate;

(c1) mannitol;

(c2) polysorbate 80;

(d) water;

(e) optionally, an acidifying agent; and (f) optionally, an alkalizing agent, wherein the formulation has a pH of from about 5.0 to about 6.0.

Embodiment 22 includes a modification to the pharmaceutical formulation of any of embodiments 1-21, wherein the pharmaceutical formulation consists essentially of:

(a) the recombinant acid α-glucosidase, present at a concentration of about 15 mg/mL;

(b) sodium citrate buffer, present at a concentration of about 25 mM;

(c1) mannitol, present at a concentration of about 20 mg/mL;

(c2) polysorbate 80, present at a concentration of about 0.5 mg/mL; and
(d) water;
(e) optionally, an acidifying agent; and
(f) optionally, an alkalizing agent,
wherein the formulation has a pH of from about 5.0 to about 6.0.

Another aspect of the invention pertains to a lyophilized pharmaceutical composition. Accordingly, embodiment 23 pertains to a pharmaceutical composition comprising the formulation of any of embodiments 1-22 after lyophilization. Embodiment 24 pertains to a pharmaceutical composition comprising a lyophilized mixture comprising:
(a) a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa;
(b) a buffer selected from the group consisting of a citrate, a phosphate and combinations thereof; and
(c) at least one excipient selected from the group consisting of trehalose, mannitol, polysorbate 80, and combinations thereof.

Another aspect of the invention pertains to a method of treating Pompe disease. Accordingly, embodiment 25 comprises administering to a patient in need thereof the pharmaceutical formulation of embodiments 1-22. Embodiment 26 includes a modification to the method of embodiment 25, further comprising diluting the pharmaceutical formulation prior to administration to the patient. Embodiment 27 pertains to a method of treating Pompe disease comprising: reconstituting the pharmaceutical composition of embodiment 23 or 24; and administering the reconstituted pharmaceutical composition to a patient in need thereof.

Another aspect of the invention pertains to a method of preparing the above pharmaceutical formulations. Accordingly, embodiment 28 pertains to a method of preparing the pharmaceutical formulation of any of embodiments 1-22, the method comprising: adding the at least one buffer, at least one excipient and recombinant acid α-glucosidase to water to provide a solution; optionally adjusting the pH of the solution; and optionally adding additional water to the solution. Embodiment 29 includes a modification to the method of embodiment 28, further comprising filtering the solution. Embodiment 30 includes a modification to the method of embodiment 27 or 28, further comprising storing the solution.

BRIEF DESCRIPTION OF THE DRAWINGS

Further features of the present invention will become apparent from the following written description and the accompanying figures, in which:

As shown in FIG. 3A, 78% of the GAA activity in Lumizyme® eluted prior to addition of M6P. FIG. 3B shows that 73% of the GAA Myozyme® activity eluted prior to addition of M6P. Only 22% or 27% of the rhGAA in Lumizyme® or Myozyme®, respectively, was eluted with M6P. These figures show that most of the rhGAA in these two conventional rhGAA products lack glycans having M6P needed to target CIMPR in target muscle tissues.

FIG. 8 is a table showing a summary of N-glycan structures of Lumizyme® compared to three different preparations of ATB200 rhGAA, identified as BP-rhGAA, ATB200-1 and ATB200-2.

FIG. 11A is a graph comparing ATB200 rhGAA activity (left trace) with Lumizyme® rhGAA activity (right trace) inside normal fibroblasts at various GAA concentrations.

FIG. 11B is a table comparing ATB200 rhGAA activity (left trace) with Lumizyme® rhGAA activity (right trace) inside fibroblasts from a subject having Pompe Disease at various GAA concentrations.

FIG. 11C is a table comparing $K_{uptake}$ of fibroblasts from normal subjects and subjects with Pompe Disease.

DETAILED DESCRIPTION

Figure 1A:
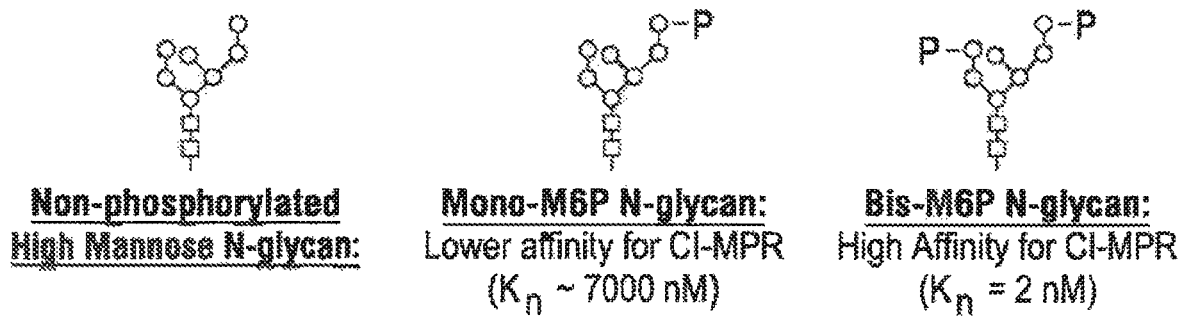
FIG. 1A shows non-phosphorylated high mannose glycan, a mono-M6P glycan, and a bis-M6P glycan.

Before describing several exemplary embodiments of the invention, it is to be understood that the invention is not limited to the details of construction or process steps set forth in the following description. The invention is capable of other embodiments and of being practiced or being carried out in various ways. It will be understood that the embodiments listed below may be combined not only as listed below, but in other suitable combinations in accordance with the scope of the invention.

It has been surprisingly discovered that by careful selection of buffers and excipients, a formulation for the recombinant GAA protein ATB200 can be provided that exhibits superior stability and can undergo the processes associated with formulation preparation, storage, transportation, reconstitution and administration while maintaining enzyme activity and effectiveness, but minimizing precipitation of the enzyme. Accordingly, one aspect of the invention pertains to a formulation comprising rhGAA, a buffer, and at least one excipient. In one or more embodiments, the rhGAA comprises ATB200. In some embodiments, the formulation is a liquid formulation. Details and various embodiments regarding the various ingredients of the formulation follow below.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

As used herein, the term "Pompe disease," also referred to as acid maltase deficiency, glycogen storage disease type II (GSDII), and glycogenosis type II, is intended to refer to a genetic lysosomal storage disorder characterized by mutations in the GAA gene, which codes for the human acid α-glucosidase enzyme. The term includes but is not limited to early and late onset forms of the disease, including but not limited to infantile, juvenile and adult-onset Pompe disease.

As used herein, the term "acid α-glucosidase" is intended to refer to a lysosomal enzyme which hydrolyzes α-1,4 linkages between the D-glucose units of glycogen, maltose, and isomaltose. Alternative names include but are not limited to lysosomal α-glucosidase (EC: 3.2.1.20); glucoamylase; 1,4-α-D-glucan glucohydrolase; amyloglucosidase; gamma-amylase and exo-1,4-α-glucosidase. Human acid α-glucosidase is encoded by the GAA gene (National Centre for Biotechnology Information (NCBI) Gene ID 2548), which has been mapped to the long arm of chromosome 17 (location 17q25.2-q25.3). The full wild-type GAA amino acid sequence is set forth in SEQ ID NO: 1, as described in U.S. Pat. No. 8,592,362 and has GenBank accession number AHE24104.1 (GI: 568760974).

More than 500 mutations have currently been identified in the human GAA gene, many of which are associated with Pompe disease. Mutations resulting in misfolding or misprocessing of the acid α-glucosidase enzyme include T1064C (Leu355Pro) and C2104T (Arg702Cys). In addition, GAA mutations which affect maturation and processing of the enzyme include Leu405Pro and Met519Thr. The conserved hexapeptide WIDMNE at amino acid residues 516-521 is required for activity of the acid α-glucosidase protein. As used herein, the abbreviation "GAA" is intended to refer to the acid α-glucosidase enzyme, while the italicized abbreviation "GAA" is intended to refer to the human gene coding for the human acid α-glucosidase enzyme. Thus, the abbreviation "rhGAA" is intended to refer to the recombinant human acid α-glucosidase enzyme.

As used herein, the term "alglucosidase alfa" is intended to refer to a recombinant human acid α-glucosidase identified as [199-arginine,223-histidine]prepro-α-glucosidase (human); Chemical Abstracts Registry Number 420794-05-0. Alglucosidase alfa is approved for marketing in the United States by Genzyme, as of January 2016, as the products Lumizyme® and Myozyme®.

As used herein, the term "ATB200" is intended to refer to a recombinant human acid α-glucosidase described in co-pending patent application PCT/US2015/053252, the disclosure of which is herein incorporated by reference.

As used herein, the term "glycan" is intended to refer to a polysaccharide chain covalently bound to an amino acid residue on a protein or polypeptide. As used herein, the term "N-glycan" or "N-linked glycan" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans can contain one or several monosaccharide units, and the monosaccharide units can be covalently linked to form a straight chain or a branched chain. In at least one embodiment, N-glycan units attached to ATB200 can comprise one or more monosaccharide units each independently selected from N-acetylglucosamine, mannose, galactose or sialic acid. The N-glycan units on the protein can be determined by any appropriate analytical technique, such as mass spectrometry. In some embodiments, the N-glycan units can be determined by liquid chromatography-tandem mass spectrometry (LC-MS/MS) utilizing an instrument such as the Thermo Scientific Orbitrap Velos Pro™ Mass Spectrometer, Thermo Scientific Orbitrap Fusion Lumos Tribid™ Mass Spectrometer or Waters Xevo® G2-XS QTof Mass Spectrometer.

As used herein, the term "high mannose N-glycan" is intended to refer to an N-glycan having one to six or more mannose units. In at least one embodiment, a high mannose N-glycan unit can contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position; i.e. having a phosphate group bonded to the hydroxyl group at the 6 position. In at least one embodiment, one or more mannose units of one or more N-glycan units are phosphorylated at the 6 position to form mannose-6-phosphate units.

As used herein, the term "complex N-glycan" is intended to refer to an N-glycan containing one or more galactose and/or sialic acid units. In at least one embodiment, a complex N-glycan can be a high mannose N-glycan in which one or mannose units are further bonded to one or more monosaccharide units each independently selected from N-acetylglucosamine, galactose and sialic acid.

As used herein, the "therapeutically effective dose" and "effective amount" are intended to refer to an amount of acid α-glucosidase, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Pompe disease such as those known in the art. Symptoms or markers of Pompe disease include but are not limited to decreased acid α-glucosidase tissue activity; cardiomyopathy; cardiomegaly; progressive muscle weakness, especially in the trunk or lower limbs; profound hypotonia; macroglossia (and in some cases, protrusion of the tongue); difficulty swallowing, sucking, and/or feeding; respiratory insufficiency; hepatomegaly (moderate); laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the term "excipient" refers to a substance other than the active ingredients included in a formulation, and are generally an inactive material. The excipient may help transport the active drug to the site where the drug is intended to take effect, control the release of the active drug, or help with solubilization, or can serve a variety of other functions. Examples of excipients include, but are not limited to, buffering agents, surfactants, antimicrobial agents, antioxidants, bulking agents, stabilizer, tonicity modifiers etc.

As used herein, the term "buffer" is intended to refer to a solution containing both a weak acid and its conjugate weak base, the pH of which changes only slightly with the addition of an alkali or acid. As will be explained further below, in some embodiments, the buffer used in the pharmaceutical formulation is a citrate and/or phosphate buffer.

As used herein, the terms "subject" or "patient" are intended to refer to a human or non-human animal. In at least one embodiment, the subject is a mammal. In at least one embodiment, the subject is a human.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in various embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

ATB200 rhGAA

The formulation comprises ATB200, which is a recombinant GAA (rhGAA) protein suitable for use in enzyme replacement therapy. Details regarding the structure and production of ATB200, as well as variants, are provided below.

Figure 1B:
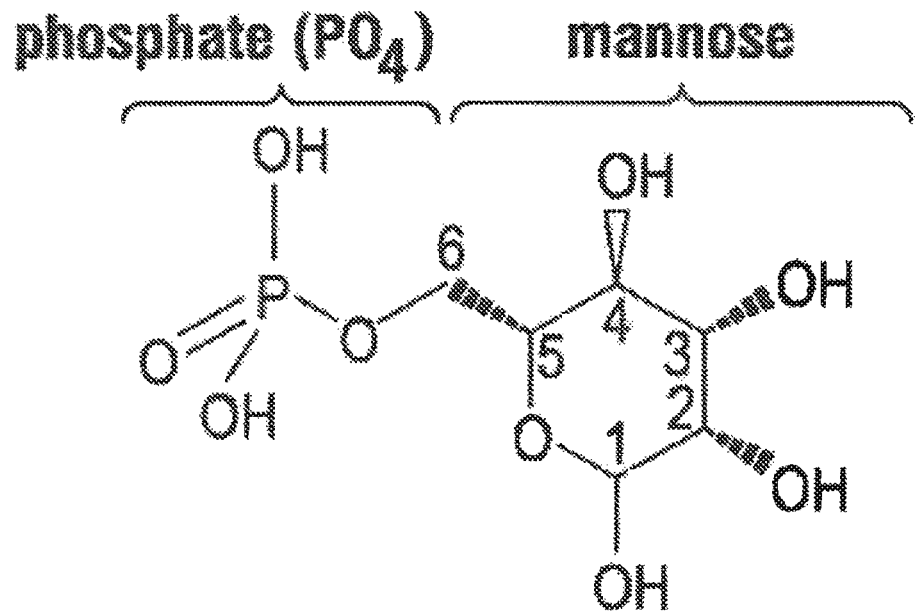
FIG. 1B shows the chemical structure of the M6P group.
Figures 2A, 2B:
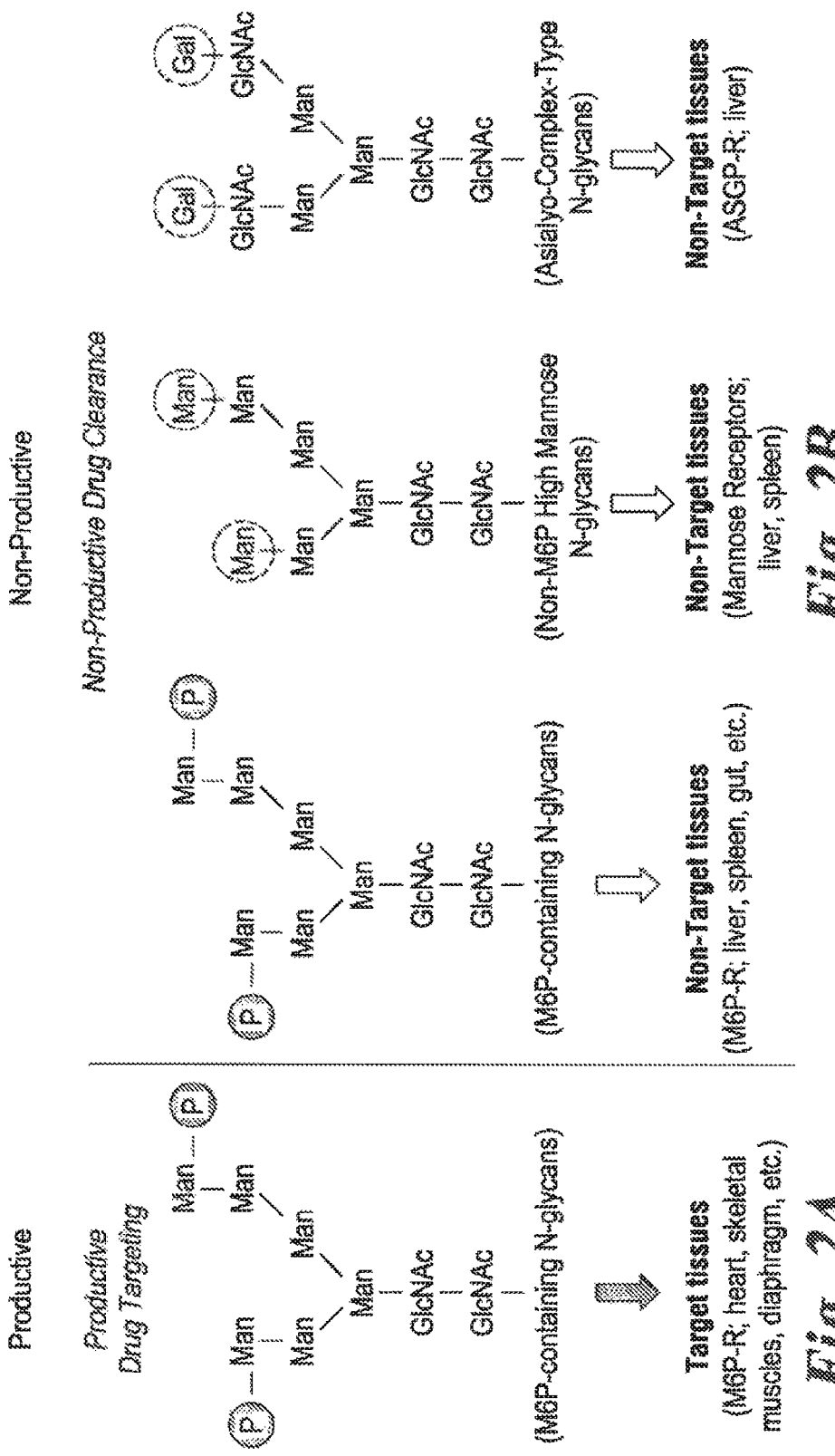
FIG. 2A describes productive targeting of rhGAA via glycans bearing M6P to target tissues (e.g. muscle tissues of subject with Pompe Disease).
FIG. 2B describes non-productive drug clearance to non-target tissues (e.g. liver and spleen) or by binding of non-M6P glycans to non-target tissues.

In at least one embodiment, the ATB200 is expressed in Chinese hamster ovary (CHO) cells and comprises an increased content of N-glycan units bearing one or more mannose-6-phosphate residues when compared to a content of N-glycan units bearing one or more mannose-6-phosphate residues of alglucosidase alfa. There are seven potential N-linked glycosylation sites on rhGAA. Since each glycosylation site is heterogeneous in the type of N-linked oligosaccharides (N-glycans) present, rhGAA consist of a complex mixture of proteins with N-glycans having varying binding affinities for M6P receptor and other carbohydrate receptors. rhGAA that contains a high mannose N-glycans having one M6P group (mono-M6P) binds to CIMPR with low (~6,000 nM) affinity while rhGAA that contains two M6P groups on same N-glycan (bis-M6P) bind with high (~2 nM) affinity. Representative structures for non-phosphorylated, mono-M6P, and bis-M6P glycans are shown by FIG. 1A. The mannose-6-P group is shown by FIG. 1B. Once inside the lysosome, rhGAA can enzymatically degrade accumulated glycogen. However, conventional rhGAAs have low total levels of M6P- and bis-M6P bearing glycans and, thus, target muscle cells poorly resulting in inferior delivery of rhGAA to the lysosomes. Productive drug targeting of rhGAA is shown in FIG. 2A. The majority of rhGAA molecules in these conventional products do not have phosphorylated N-glycans, thereby lacking affinity for the CIMPR. Non-phosphorylated high mannose glycans can also be cleared by the mannose receptor which results in non-productive clearance of the ERT (FIG. 2B).

The other type of N-glycans, complex carbohydrates, which contain galactose and sialic acids, are also present on rhGAA. Since complex N-glycans are not phosphorylated they have no affinity for CIMPR. However, complex-type N-glycans with exposed galactose residues have moderate to high affinity for the asialoglycoprotein receptor on liver hepatocytes which leads to rapid non-productive clearance of rhGAA (FIG. 2B).

In at least one embodiment, the acid α-glucosidase is a recombinant human acid α-glucosidase referred to herein as ATB200, as described in co-pending international patent application PCT/US2015/053252. ATB200 has been shown to bind cation-independent mannose-6-phosphate receptors (CIMPR) with high affinity ($K_D$~2-4 nM) and to be efficiently internalized by Pompe fibroblasts and skeletal muscle myoblasts ($K_{uptake}$~7-14 nM). ATB200 was characterized in vivo and shown to have a shorter apparent plasma half-life ($t_{1/2}$~45 min) than alglucosidase alfa ($t_{1/2}$~60 min).

In one or more embodiments, the recombinant human acid α-glucosidase has a wild-type GAA amino acid sequence as set forth in SEQ ID NO: 2, which corresponds to amino acid residues 57-952 and is identical to wild-type (WT) human GAA after natural intracellular proteolytic processing that removes the initial 56 residues comprising the signal peptide and precursor peptide. The ATB200 amino acid sequence has been verified by tryptic digestion followed by liquid chromatography/mass spectroscopy as well as by amino acid sequencing. By contrast, the current standard of care rhGAA enzyme replacement therapy (ERT) (commercially available products containing alglucosidase alfa are Myozyme® in most countries and Lumizyme® in the US, Genzyme, a Sanofi Company) differs from WT GAA and contains 3 amino acid residues substitutions: histidine changed to arginine at position 199, arginine changed to histidine at 223, and valine changed to isoleucine at 780.

In at least one embodiment, the recombinant human acid α-glucosidase undergoes post-translational and/or chemical modifications at one or more amino acid residues in the protein. For example, methionine and tryptophan residues can undergo oxidation. As another example, asparagine residues can undergo deamidation to aspartic acid. As yet another example, aspartic acid can undergo isomerization to iso-aspartic acid. Accordingly, in some embodiments the enzyme is initially expressed as having an amino acid sequence as set forth in SEQ ID NO: 1, or SEQ ID NO: 2, and the enzyme undergoes one or more of these post-translational and/or chemical modifications. Such modifications are also within the scope of the present disclosure.

In at least one embodiment, the recombinant human acid α-glucosidase has a wild-type GAA amino acid sequence as set forth in SEQ ID NO: 1, as described in U.S. Pat. No. 8,592,362 and has GenBank accession number AHE24104.1 (GI: 568760974). In at least one embodiment, the recombinant human acid α-glucosidase is glucosidase alfa, the human acid α-glucosidase enzyme encoded by the most predominant of nine observed haplotypes of the GAA gene.

In at least one embodiment, the recombinant human acid α-glucosidase is initially expressed as having the full-length 952 amino acid sequence of wild-type GAA as set forth in SEQ ID NO: 1, and the recombinant human acid α-glucosidase undergoes intracellular processing that removes a portion of the amino acids, e.g. the first 56 amino acids. Accordingly, the recombinant human acid α-glucosidase that is secreted by the host cell can have a shorter amino acid sequence than the recombinant human acid α-glucosidase that is initially expressed within the cell. In at least one embodiment, the shorter protein can have the amino acid sequence set forth in SEQ ID NO: 2, which only differs from SEQ ID NO: 1 in that the first 56 amino acids comprising the signal peptide and precursor peptide have been removed, thus resulting in a protein having 896 amino acids. Other variations in the number of amino acids is also possible, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. In some embodiments, the rhGAA product includes a mixture of recombinant human acid α-glucosidase molecules having different amino acid lengths.

In at least one embodiment, the recombinant human acid α-glucosidase undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments the enzyme is initially expressed as having an amino acid sequence as set forth in SEQ ID NO: 1 or SEQ ID NO: 2, and the enzyme undergoes one or more of these post-translational and/or chemical modifications. Such modifications are also within the scope of the present disclosure.

Preferably, no more than 70, 65, 60, 55, 45, 40, 35, 30, 25, 20, 15, 10, or 5% of the total recombinant human acid α-glucosidase molecules lack an N-glycan unit bearing one or more mannose-6-phosphate residues or lacks a capacity to bind to the cation independent mannose-6-phosphate receptor (CIMPR). Alternatively, 30, 35, 40, 45, 50, 55, 60, 65, 70, 75, 80, 85, 90, 95, 99%, <100% or more of the recombinant human acid α-glucosidase molecules comprise at least one N-glycan unit bearing one or more mannose-6-phosphate residues or has the capacity to bind to CIMPR.

The recombinant human acid α-glucosidase molecules may have 1, 2, 3 or 4 mannose-6-phosphate (M6P) groups on their glycans. For example, only one N-glycan on a recombinant human acid α-glucosidase molecule may bear M6P (mono-phosphorylated), a single N-glycan may bear two M6P groups (bis-phosphorylated), or two different N-glycans on the same recombinant human acid α-glucosidase molecule may each bear single M6P groups. Recombinant human acid α-glucosidase molecules may also have N-glycans bearing no M6P groups. In another embodiment, on average the N-glycans contain greater than 3 mol/mol of M6P and greater than 4 mol/mol sialic acid, such that the recombinant human acid α-glucosidase comprises on average at least 3 moles of mannose-6-phosphate residues per mole of recombinant human acid α-glucosidase and at least 4 moles of sialic acid per mole of recombinant human acid α-glucosidase. On average at least about 3, 4, 5, 6, 7, 8, 9, or 10% of the total glycans on the recombinant human acid α-glucosidase may be in the form of a mono-M6P glycan, for example, about 6.25% of the total glycans may carry a single M6P group and on average, at least about 0.5, 1, 1.5, 2.0, 2.5, 3.0% of the total glycans on the recombinant human acid α-glucosidase are in the form of a bis-M6P glycan and on average less than 25% of total recombinant human acid α-glucosidase contains no phosphorylated glycan binding to CIMPR.

The recombinant human acid α-glucosidase may have an average content of N-glycans carrying M6P ranging from 0.5 to 7.0 mol/mol recombinant human acid α-glucosidase or any intermediate value of subrange including 0.5, 1.0, 1.5, 2.0, 2.5, 3.0, 3.5, 4.0, 4.5, 5.0, 5.5, 6.0, 6.5, or 7.0 mol/mol recombinant human acid α-glucosidase. The recombinant human acid α-glucosidase can be fractionated to provide recombinant human acid α-glucosidase preparations with different average numbers of M6P-bearing or bis-M6P-bearing glycans thus permitting further customization of the recombinant human acid α-glucosidase targeting to the lysosomes in target tissues by selecting a particular fraction or by selectively combining different fractions.

In some embodiments, the recombinant human acid α-glucosidase will bear, on average, 2.0 to 8.0 moles of M6P per mole of recombinant human acid α-glucosidase. This range includes all intermediate values and subranges including 2.0, 2.5, 3.0, 3.5, 4.0, 4.5, 5.0, 5.5, 6.0, 6.5, 7.0, 7.5 and 8.0 mol M6P/mol recombinant human acid α-glucosidase.

Up to 60% of the N-glycans on the recombinant human acid α-glucosidase may be fully sialylated, for example, up to 10%, 20%, 30%, 40%, 50% or 60% of the N-glycans may be fully sialylated. In some embodiments from 4 to 20% of the total N-glycans are fully sialylated. In other embodiments no more than 5%, 10%, 20% or 30% of N-glycans on the recombinant human acid α-glucosidase carry sialic acid and a terminal galactose residue (Gal). This range includes all intermediate values and subranges, for example, 7 to 30% of the total N-glycans on the recombinant human acid α-glucosidase can carry sialic acid and terminal galactose. In yet other embodiments, no more than 5, 10, 15, 16, 17, 18, 19 or 20% of the N-glycans on the recombinant human acid α-glucosidase have a terminal galactose only and do not contain sialic acid. This range includes all intermediate values and subranges, for example, from 8 to 19% of the total N-glycans on the recombinant human acid α-glucosidase in the composition may have terminal galactose only and do not contain sialic acid.

In other embodiments of the invention, 40, 45, 50, 55 to 60% of the total N-glycans on the recombinant human acid α-glucosidase are complex type N-glycans; or no more than 1, 2, 3, 4, 5, 6, 7% of total N-glycans on the recombinant human acid α-glucosidase are hybrid-type N-glycans; no more than 5, 10, or 15% of the high mannose-type N-glycans on the recombinant human acid α-glucosidase are non-phosphorylated; at least 5% or 10% of the high mannose-type N-glycans on the recombinant human acid α-glucosidase are mono-M6P phosphorylated; and/or at least 1 or 2% of the high mannose-type N-glycans on the recombinant human acid α-glucosidase are bis-M6P phosphorylated. These values include all intermediate values and subranges. A recombinant human acid α-glucosidase may meet one or more of the content ranges described above.

In some embodiments, the recombinant human acid α-glucosidase will bear, on average, 2.0 to 8.0 moles of sialic acid residues per mole of recombinant human acid α-glucosidase. This range includes all intermediate values and subranges including 2.0, 2.5, 3.0, 3.5, 4.0, 4.5, 5.0, 5.5, 6.0, 6.5, 7.0, 7.5 and 8.0 mol residues/mol recombinant human acid α-glucosidase. Without being bound by theory, it is believed that the presence of N-glycan units bearing sialic acid residues may prevent non-productive clearance of the recombinant human acid α-glucosidase by asialoglycoprotein receptors.

In one or more embodiments, the rhGAA has M6P and/or sialic acid units at certain N-glycosylation sites of the recombinant human lysosomal protein. For example, there are seven potential N-linked glycosylation sites on rhGAA. These potential glycosylation sites are at the following positions of SEQ ID NO: 2: N84, N177, N334, N414, N596, N826 and N869. Similarly, for the full-length amino acid sequence of SEQ ID NO: 1, these potential glycosylation sites are at the following positions: N140, N233, N390, N470, N652, N882 and N925. Other variants of rhGAA can have similar glycosylation sites, depending on the location of asparagine residues. Generally, sequences of ASN-X-SER or ASN-X-THR in the protein amino acid sequence indicate potential glycosylation sites, with the exception that X cannot be HIS or PRO.

In various embodiments, the rhGAA has a certain N-glycosylation profile. In one or more embodiments, at least 20% of the rhGAA is phosphorylated at the first N-glycosylation site (e.g. N84 for SEQ ID NO: 2 and N140 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the first N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the first N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the first N-glycosylation site.

In one or more embodiments, at least 20% of the rhGAA is phosphorylated at the second N-glycosylation site (e.g. N177 for SEQ ID NO: 2 and N223 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the second N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the second N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the second N-glycosylation site. In one or more embodiments, at least 5% of the rhGAA is phosphorylated at the third N-glycosylation site (e.g. N334 for SEQ ID NO: 2 and N390 for SEQ ID NO: 1). In other embodiments, less than 5%, 10%, 15%, 20% or 25% of the rhGAA is phosphorylated at the third N-glycosylation site. For example, the third N-glycosylation site can have a mixture of non-phosphorylated high mannose glycans, di-, tri-, and tetra-antennary complex glycans, and hybrid glycans as the major species. In some embodiments, at least 3%, 5%, 8%, 10%, 15%, 20%, 25%, 30%, 35%, 40%, 45% or 50% of the rhGAA is sialylated at the third N-glycosylation site.

In one or more embodiments, at least 20% of the rhGAA is phosphorylated at the fourth N-glycosylation site (e.g. N414 for SEQ ID NO: 2 and N470 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the fourth N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the fourth N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the fourth N-glycosylation site. In some embodiments, at least 3%, 5%, 8%, 10%, 15%, 20% or 25% of the rhGAA is sialylated at the fourth N-glycosylation site.

In one or more embodiments, at least 5% of the rhGAA is phosphorylated at the fifth N-glycosylation site (e.g. N596 for SEQ ID NO: 2 and N692 for SEQ ID NO: 1). In other embodiments, less than 5%, 10%, 15%, 20% or 25% of the rhGAA is phosphorylated at the fifth N-glycosylation site. For example, the fifth N-glycosylation site can have fucosylated di-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the fifth N-glycosylation site.

In one or more embodiments, at least 5% of the rhGAA is phosphorylated at the sixth N-glycosylation site (e.g. N826 for SEQ ID NO: 2 and N882 for SEQ ID NO: 1). In other embodiments, less than 5%, 10%, 15%, 20% or 25% of the rhGAA is phosphorylated at the sixth N-glycosylation site. For example, the sixth N-glycosylation site can have a mixture of di-, tri-, and tetra-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the sixth N-glycosylation site.

In one or more embodiments, at least 5% of the rhGAA is phosphorylated at the seventh N-glycosylation site (e.g. N869 for SEQ ID NO: 2 and N925 for SEQ ID NO: 1). In other embodiments, less than 5%, 10%, 15%, 20% or 25% of the rhGAA is phosphorylated at the seventh N-glycosylation site. In some embodiments, less than 40%, 45%, 50%, 55%, 60% or 65% % of the rhGAA has any glycan at the seventh N-glycosylation site. In some embodiments, at least 30%, 35% or 40% of the rhGAA has a glycan at the seventh N-glycosylation site.

In various embodiments, the rhGAA has an average fucose content of 0-5 mol per mol of rhGAA, GlcNAc content of 10-30 mol per mol of rhGAA, galactose content of 5-20 mol per mol of rhGAA, mannose content of 10-40 mol per mol of rhGAA, M6P content of 2-8 mol per mol of rhGAA and sialic acid content of 2-8 mol per mol of rhGAA. In various embodiments, the rhGAA has an average fucose content of 2-3 mol per mol of rhGAA, GlcNAc content of 20-25 mol per mol of rhGAA, galactose content of 8-12 mol per mol of rhGAA, mannose content of 22-27 mol per mol of rhGAA, M6P content of 3-5 mol per mol of rhGAA and sialic acid content of 4-7 mol of rhGAA.

The recombinant human acid α-glucosidase is preferably produced by Chinese hamster ovary (CHO) cells, such as CHO cell line GA-ATB200 or ATB200-001-X5-14, or by a subculture or derivative of such a CHO cell culture. DNA constructs, which express allelic variants of acid α-glucosidase or other variant acid α-glucosidase amino acid sequences such as those that are at least 90%, 95% or 99% identical to SEQ ID NO: 1, may be constructed and expressed in CHO cells. These variant acid α-glucosidase amino acid sequences may contain deletions, substitutions and/or insertions relative to SEQ ID NO: 1, such as having 1, 2, 3, 4, 5, 6, 7, 8, 9, 10 or more deletions, substitutions and/or insertions to the amino acid sequence described by SEQ ID NO: 1. Those of skill in the art can select alternative vectors suitable for transforming CHO cells for production of such DNA constructs.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 90%, 95% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

In some embodiments, the recombinant human acid α-glucosidase having superior ability to target cation-independent mannose-6-phosphate receptors (CIMPR) and cellular lysosomes as well as glycosylation patterns that reduce its non-productive clearance in vivo can be produced using Chinese hamster ovary (CHO) cells. These cells can be induced to express recombinant human acid α-glucosidase with significantly higher levels of N-glycan units bearing one or more mannose-6-phosphate residues than conventional recombinant human acid α-glucosidase products such as alglucosidase alfa. The recombinant human acid α-glucosidase produced by these cells, for example, as exemplified by ATB200, has significantly more muscle cell-targeting mannose-6-phosphate (M6P) and bis-mannose-6-phosphate N-glycan residues than conventional acid α-glucosidase, such as Lumizyme®. Without being bound by theory, it is believed that this extensive glycosylation allows the ATB200 enzyme to be taken up more effectively into target cells, and therefore to be cleared from the circulation more efficiently than other recombinant human acid α-glucosidases, such as for example, alglucosidase alfa, which has a much lower M6P and bis-M6P content. ATB200 has been shown to efficiently bind to CIMPR and be efficiently taken up by skeletal muscle and cardiac muscle and to have a glycosylation pattern that provides a favorable pharmacokinetic profile and reduces non-productive clearance in vivo.

It is also contemplated that the extensive glycosylation of ATB200 can contribute to a reduction of the immunogenicity of ATB200 compared to, for example, alglucosidase alfa. As will be appreciated by those skilled in the art, glycosylation of proteins with conserved mammalian sugars generally enhances product solubility and diminishes product aggregation and immunogenicity. Glycosylation indirectly alters protein immunogenicity by minimizing protein aggregation as well as by shielding immunogenic protein epitopes from the immune system (Guidance for Industry—Immunogenicity Assessment for Therapeutic Protein Products, US Department of Health and Human Services, Food and Drug Administration, Center for Drug Evaluation and Research, Center for Biologics Evaluation and Research, August 2014). Therefore, in at least one embodiment, administration of the recombinant human acid α-glucosidase does not induce anti-drug antibodies. In at least one embodiment, administration of the recombinant human acid α-glucosidase induces a lower incidence of anti-drug antibodies in a subject than the level of anti-drug antibodies induced by administration of alglucosidase alfa.

As described in co-pending international patent application PCT/US2015/053252, cells such as CHO cells can be used to produce the rhGAA described therein, and this rhGAA can be used in the present invention. Examples of such a CHO cell line are GA-ATB200 or ATB200-001-X5-14, or a subculture thereof that produces a rhGAA composition as described therein. Such CHO cell lines may contain multiple copies of a gene, such as 5, 10, 15, or 20 or more copies, of a polynucleotide encoding GAA.

The high M6P and bis-M6P rhGAA, such as ATB200 rhGAA, can be produced by transforming CHO cells with a DNA construct that encodes GAA. While CHO cells have been previously used to make rhGAA, it was not appreciated that transformed CHO cells could be cultured and selected in a way that would produce rhGAA having a high content of M6P and bis-M6P glycans which target the CIMPR.

Surprisingly, it was found that it was possible to transform CHO cell lines, select transformants that produce rhGAA containing a high content of glycans bearing M6P or bis-M6P that target the CIMPR, and to stably express this high-M6P rhGAA. Thus, methods for making these CHO cell lines are also described in co-pending international patent application PCT/US2015/053252. This method involves transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of glycans bearing M6P or bis-M6P, and, optionally, selecting a CHO cell having N-glycans with high sialic acid content and/or having N-glycans with a low non-phosphorylated high mannose content. These CHO cell lines may be used to produce rhGAA and rhGAA compositions by culturing the CHO cell line and recovering said composition from the culture of CHO cells.

In one or more embodiments, the ATB200 is present in an amount ranging from about 5 to about 50 mg/mL. In further embodiments, the ATB200 is present in an amount ranging from about 5, 8, 10, or 12 to about 18, 20, 25, 30, 35, 40, 45 or 50 mg/mL. In some embodiments, the ATB200 is present in an amount of about 5, 6, 7, 8, 9, 10, 11, 12, 13, 14, 15, 16, 17, 18, 19, 20, 21, 22, 23, 24, 25, 26, 27, 28, 29 or 30 mg/mL. In further embodiments, the ATB200 is present in an amount of about 15 mg/mL.

pH and Buffer

The pH of the formulation may range from about 5.0 to about 7.0 or about 5.0 to about 6.0. In one or more embodiments, the pH ranges from about 5.5 to about 6.0. In some embodiments, the formulation has a pH of about 5.0, 5.1, 5.2, 5.3, 5.4, 5.5, 5.6, 5.7, 5.8, 5.9 or 6.0, 6.1, 6.2, 6.3, 6.4 or 6.5. Generally, the amounts of components as recited will yield a pH in the range of from about 5.0 to about 6.0. However, the pH may be adjusted to a target pH by using pH adjusters (i.e., alkalizing agents and acidifying agents), such as sodium hydroxide and/or hydrochloric acid.

The formulation also comprises a buffer that is selected from the group consisting of a citrate, a phosphate and combinations thereof. As used herein, "buffer" refers to a buffer solution containing a weak acid and its conjugate base that helps to prevent changes in pH. The citrate and/or phosphate may be a sodium citrate or sodium phosphate. Other salts include potassium and ammonium salts. In one or more embodiments, the buffer comprises a citrate. In further embodiments, the buffer comprises sodium citrate (e.g., a mixture of sodium citrate dehydrate and citric acid monohydrate). In one or more embodiments, buffer solutions comprising a citrate may comprise sodium citrate and citric acid. In some embodiments, both a citrate and phosphate buffer are present.

Excipients

The formulation also comprises at least one excipient. Some embodiments of the invention comprise excipients that aid with tonicity, act as a bulking agent or act as stabilizers. In one or more embodiments, the at least one excipient is selected from the group consisting of mannitol, polysorbate and combinations thereof.

In one or more embodiments, the excipient comprises an ingredient that can act as a tonicity modifier and/or bulking agent, particularly mannitol. Tonicity agents are components which help to ensure the formulation has an osmotic pressure similar to or the same as human blood. Bulking agents are ingredients which add mass to the formulations (e.g. lyophilized) and provide an adequate structure to the cake.

In one or more embodiments, the total amount of tonicity and/or bulking agent ranges in an amount of from about 10 to about 50 mg/mL. In further embodiments, the total amount of tonicity and/or bulking agent ranges in an amount of from about 10, 11, 12, 13, 14 or 15 to about 16, 20, 25, 30, 35, 40, 45 or 50 mg/mL. In some embodiments, the tonicity and/or bulking agent comprises mannitol. In one or more embodiments, the mannitol is present in an amount of from about 10 to about 50 mg/mL. In further embodiments, the mannitol is present in an amount of from about 10, 11, 12, 13, 14 or 15 to about 16, 20, 25, 30, 35, 40, 45 or 50 mg/mL. In yet further embodiments, the mannitol is present in an amount of about 10, 11, 12, 13, 14, 15, 16, 17, 18, 19 or 20 mg/mL. In some embodiments, mannitol is the only tonicity and/or bulking agent. Examples of other tonicity and/or bulking agents include, sodium chloride, sucrose, and trehalose.

In some embodiments, the excipient comprises an ingredient that can act a stabilizer, such as polysorbate 80. Stabilizers are compounds that can prevent or minimize the aggregate formation at the hydrophobic air-water interfacial surfaces. In some embodiments, the stabilizer is a surfactant. In one or more embodiments, the total amount of stabilizer ranges from about 0.1 to about 1.0 mg/mL. In further embodiments, the total amount of stabilizer ranges from about 0.1, 0.2, 0.3, 0.4 or 0.5 to about 0.5, 0.6, 0.7, 0.8 0.9 or 1.0 mg/mL. In yet further embodiments, the total amount of stabilizer is about 0.1, 0.2, 0.3, 0.4, 0.5, 0.6, 0.7, 0.8 0.9 or 1.0 mg/mL. In some embodiments, polysorbate 80 is the only stabilizer. Thus, in one or more embodiments, the polysorbate 80 ranges from about 0.1 to about 1.0 mg/mL. In further embodiments, the polysorbate 80 ranges from about 0.1, 0.2, 0.3, 0.4 or 0.5 to about 0.5, 0.6, 0.7, 0.8 0.9 or 1.0 mg/mL. In yet further embodiments, the polysorbate 80 is about 0.1, 0.2, 0.3, 0.4, 0.5, 0.6, 0.7, 0.8 0.9 or 1.0 mg/mL.

In one or more embodiments, it may be desirable to exclude certain compounds from the formulation. For example, in preparing a formulation for the treatment of given disease, it would be desirable to exclude certain compounds which would aggravate the underlying disease. As discussed above, individuals with Pompe disease have a decreased or absent ability to breakdown glycogen. Several commonly used excipients, such as sucrose, trehalose and glycine, may be converted into glucose in the body, which would in turn aggravate Pompe disease. Thus, in some embodiments, sucrose, trehalose and/or glycine is excluded from the formulation. Similarly, certain components may be excluded which are not best suited for the formulation given certain contexts. For example, in some embodiments, poloxamers may be excluded.

EXEMPLARY EMBODIMENTS

In one or more embodiments, the formulation comprises or consists essentially of:
(a) ATB200 (e.g., a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa);
(b) at least one buffer selected from the group consisting of a citrate, a phosphate and combinations thereof;
(c) at least one excipient selected from the group consisting of mannitol, polysorbate 80, and combinations thereof; and wherein the formulation has a pH of from about 5.0 to about 6.0 or 7.0.

In some embodiments, the formulation comprises or consists essentially of:
(a) ATB200 (e.g., a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa);
(b1) sodium citrate;
(b2) citric acid monohydrate;
(c1) mannitol;
(c2) polysorbate 80;
(d) water;
(e) optionally, an acidifying agent; and
(f) optionally, an alkalizing agent,
wherein the formulation has a pH of from about 5.0 to about 6.0 or 7.0. In further embodiments, the pH ranges from about 5.5 to about 6.0. In yet further embodiments, the pH is about 6.0.

In a specific embodiment, the formulation comprises
(a) ATB200 (e.g., a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa), present at a concentration of about 5-30 mg/mL or about 15 mg/mL;
(b) sodium citrate buffer, present at a concentration of about 10-100 mM or about 25 mM;
(c1) mannitol, present at a concentration of about 10-50 mg/mL, or about 20 mg/mL;
(c2) polysorbate 80, present at a concentration of about 0.1-1 mg/mL, or about 0.5 mg/mL; and
(d) water;
(e) optionally, an acidifying agent; and
(f) optionally, an alkalizing agent,
wherein the formulation has a pH of from about 5.0 to about 6.0 or 7.0. In further embodiments, the pH ranges from about 5.5 to about 6.0. In yet further embodiments, the pH is about 6.0.

Preparation of Formulation

Another aspect of the invention pertains to methods of preparing the formulations described herein. In one or more embodiments, the formulation can be prepared from the enzyme solution. This solution may be concentrated and buffer exchanged to the targeted concentration and buffers as necessary using methods known in the art. Additional components (e.g. excipients and pH adjusters) may then be added. The formulation can then be filtered and placed into a storage container and stored.

In one or more embodiments, the method of preparing any of the pharmaceutical formulations described herein comprises: adding the at least one buffer, at least one excipient and recombinant acid α-glucosidase to water to provide a solution; optionally adjusting the pH of the solution; and optionally adding additional water to the solution. In further embodiments, the method further comprises filtering the solution. In yet further embodiments, the method further comprises storing the solution.

An exemplary, non-limiting process for the production of a formulation as described herein follows below:

1. In a suitable manufacturing vessel, add approximately 85-90% of the batch volume of Water for Injection.
2. Add and dissolve the desired excipients and buffers (e.g., sodium citrate dihydrate, citric acid monohydrate, polysorbate 80, mannitol) and mix until dissolved.
3. Add the ATB200 drug substance and mix.
4. Adjust the pH to the targeted pH (e.g., 6±0.1) as necessary with adjusters (e.g.) hydrochloric acid or sodium hydroxide solution.
5. Add sufficient Water for Injection to final volume and mix.
6. Filter the solution through a sterile filter into a sterile receiver.
7. Aseptically fill the drug product solution into vials, and insert stoppers.
8. Cap all vials and store at 2°-8° C.

In one or more embodiments, the formulation as-prepared will be in liquid form. That is, the formulation comprises water. This liquid formulation may undergo lyophilization (freeze-drying) process to provide a cake or powder. Accordingly, another aspect of the invention pertains to a pharmaceutical composition comprising anyone of the formulations described above after lyophilization. The lyophilized mixture may comprise the ATB200, buffer selected from the group consisting of a citrate, a phosphate and combinations thereof, and at least one excipient selected from the group consisting of trehalose, mannitol, polysorbate 80, and combinations thereof. In some embodiments, other ingredients (e.g., other excipients) may be added to the lyophilized mixture. The pharmaceutical composition comprising the lyophilized formulation may be provided vial, which then can be stored, transported, reconstituted and/or administered to a patient.

Method of Treatment and Administration to Patient

Another aspect of the invention pertains to a method of treatment of Pompe disease and/or use of the formulations described herein for the treatment of Pompe disease. The formulation may be administered as-prepared, or after lyophilization and reconstitution. Thus, in one or more embodiments, the method comprises administering to a patient in need thereof any of the pharmaceutical formulations described above. In other embodiments, the method comprises reconstituting the lyophilized pharmaceutical composition and administering the reconstituted pharmaceutical composition to a patient in need thereof. In some embodiments, the reconstituted pharmaceutical composition has similar or the same makeup as the pharmaceutical formulation prior to lyophilization and/or as-prepared. In either case, the pharmaceutical formulation or reconstituted pharmaceutical composition may be diluted prior to administration to the patient. In further embodiments, the pharmaceutical formulation or reconstituted pharmaceutical composition is administered intravenously.

In one or more embodiments, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In other embodiments, pharmaceutical formulation or reconstituted pharmaceutical composition is administered by direct administration to a target tissue, such as to heart or skeletal muscle (e.g. intramuscular), or nervous system (e.g. direct injection into the brain; intraventricularly; intrathecally). More than one route can be used concurrently, if desired.

The pharmaceutical formulation or reconstituted composition is administered in a therapeutically effective amount (e.g. a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. In at least one embodiment, the recombinant human acid α-glucosidase is administered by intravenous infusion at a dose of about 1 mg/kg to about 100 mg/kg, such as about 5 mg/kg to about 30 mg/kg, typically about 5 mg/kg to about 20 mg/kg. In at least one embodiment, the recombinant human acid α-glucosidase is administered by intravenous infusion at a dose of about 5 mg/kg, about 10 mg/kg, about 15 mg/kg, about 20 mg/kg, about 25 mg/kg, about 30 mg/kg, about 35 mg/kg, about 40 mg/kg, about 50 mg/kg, about 50 mg/kg, about 60 mg/kg, about 70 mg/kg, about 80 mg/kg, about 90 mg/kg or about 100 mg/kg. In at least one embodiment, the recombinant human acid α-glucosidase is administered by intravenous infusion at a dose of about 20 mg/kg. The effective dose for a particular individual can be varied (e.g. increased or decreased) over time, depending on the needs of the individual. For example, in times of physical illness or stress, or if anti-acid α-glucosidase antibodies become present or increase, or if disease symptoms worsen, the amount can be increased.

The therapeutically effective amount of recombinant human acid α-glucosidase (or composition or medicament containing recombinant human acid α-glucosidase) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, recombinant human acid α-glucosidase is administered monthly, bimonthly; weekly; twice weekly; or daily. The administration interval for a single individual need not be a fixed interval, but can be varied over time, depending on the needs of the individual. For example, in times of physical illness or stress, if anti-recombinant human acid α-glucosidase antibodies become present or increase, or if disease symptoms worsen, the interval between doses can be decreased.

In one or more embodiments, the pharmaceutical formulation or reconstituted composition is co-administered with a pharmacological chaperone, such as oral administration of the chaperone and intravenous administration of the pharmaceutical formulation or reconstituted composition. In various embodiments, the pharmacological chaperone is miglustat. In at least one embodiment, the miglustat is administered at an oral dose of about 200 mg to about 400 mg, or at an oral dose of about 200 mg, about 250 mg, about 300 mg, about 350 mg or about 400 mg. In at least one embodiment, the miglustat is administered at an oral dose of about 233 mg to about 400 mg. In at least one embodiment, the miglustat is administered at an oral dose of about 250 to about 270 mg, or at an oral dose of about 250 mg, about 255 mg, about 260 mg, about 265 mg or about 270 mg. In at least one embodiment, the miglustat is administered as an oral dose of about 260 mg.

In at least one embodiment, the miglustat and the recombinant human acid α-glucosidase are administered simultaneously. In at least one embodiment, the miglustat and the recombinant human acid α-glucosidase are administered sequentially. In at least one embodiment, the miglustat is administered prior to administration of the recombinant human acid α-glucosidase. In at least one embodiment, the miglustat is administered less than three hours prior to administration of the recombinant human acid α-glucosidase. In at least one embodiment, the miglustat is administered about two hours prior to administration of the recombinant human acid α-glucosidase. In at least one embodiment, the miglustat is administered less than two hours prior to administration of the recombinant human acid α-glucosidase. In at least one embodiment, the miglustat is administered about 1.5 hours prior to administration of the recombinant human acid α-glucosidase. In at least one embodiment, the miglustat is administered about one hour prior to administration of the recombinant human acid α-glucosidase. In at least one embodiment, the miglustat is administered from about 50 minutes to about 70 minutes prior to administration of the recombinant human acid α-glucosidase. In at least one embodiment, the miglustat is administered from about 55 minutes to about 65 minutes prior to administration of the recombinant human acid α-glucosidase. In at least one embodiment, the miglustat is administered about 30 minutes prior to administration of the recombinant human acid α-glucosidase. In at least one embodiment, the miglustat is administered from about 25 minutes to about 35 minutes prior to administration of the recombinant human acid α-glucosidase. In at least one embodiment, the miglustat is administered from about 27 minutes to about 33 minutes prior to administration of the recombinant human acid α-glucosidase.

Kit

Another aspect of the invention pertains to kits comprising the pharmaceutical formulations described herein (including after lyophilization). In one or more embodiments, the kit comprises a container (e.g., vial, tube, bag, etc.) comprising the pharmaceutical formulations (either before or after lyophilization) and instructions for reconstitution, dilution and administration.

EXAMPLES

Enzyme Example 1: Limitations of Existing Myozyme® and Lumizyme® rhGAA Products

To evaluate the ability of the rhGAA in Myozyme® and Lumizyme®, the only currently approved treatments for Pompe disease, these rhGAA preparations were injected onto a CIMPR column (which binds rhGAA having M6P groups) and subsequently eluted with a free M6 gradient. Fractions were collected in 96-well plate and GAA activity assayed by 4MU-α-glucose substrate. The relative amounts of bound and unbound rhGAA were determined based on GAA activity and reported as the fraction of total enzyme.

Figure 3A:
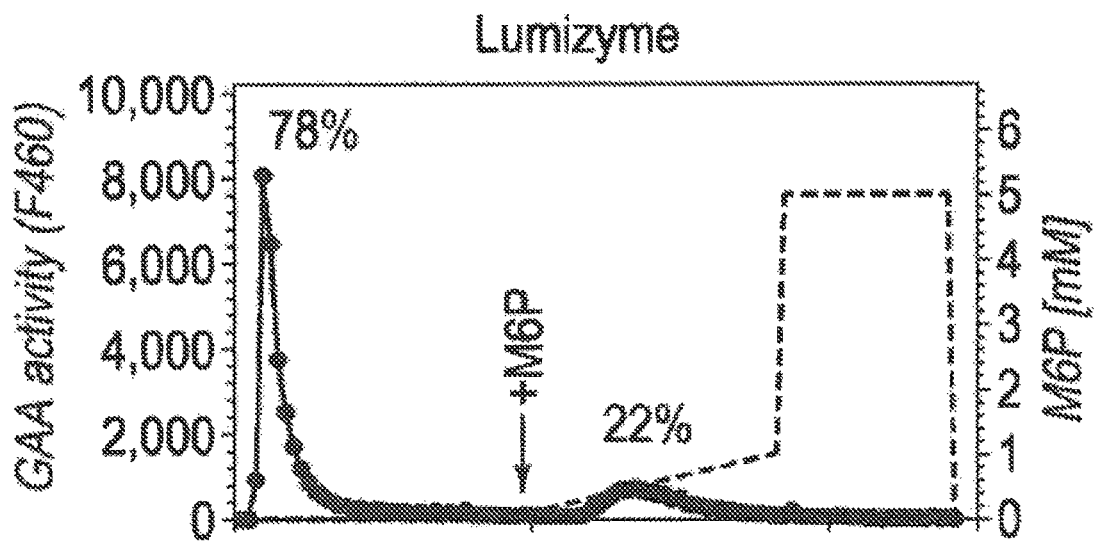
FIGS. 3A and 3B, respectively, are graphs showing the results of CIMPR affinity chromatography of Lumizyme® and Myozyme®. The dashed lines refer to the M6P elution gradient. Elution with M6P displaces GAA molecules bound via an M6P containing glycan to CIMPR.
Figure 3B:
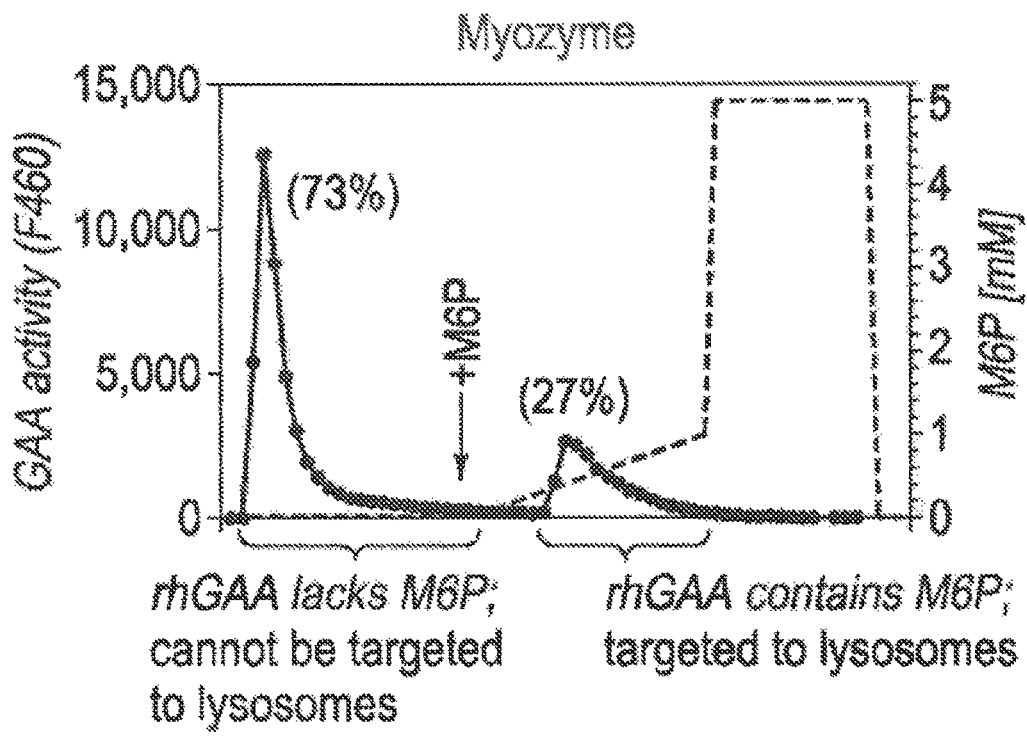

FIGS. 3A-3B show the problems associated with conventional ERTs (Myozyme® and Lumizyme®): 73% of the rhGAA in Myozyme® (FIG. 3B) and 78% of the rhGAA in Lumizyme® (FIG. 3A) did not bind to the CIMPR, see the left-most peaks in each figure. Only 27% of the rhGAA in Myozyme® and 22% of the rhGAA in Lumizyme® contained M6P that can productive to target it to the CIMPR on muscle cells.

An effective dose of Myozyme® and Lumizyme® corresponds to the amount of rhGAA containing M6P which targets the CIMPR on muscle cells. However, most of the rhGAA in these two conventional products does not target the CIMPR receptor on target muscle cells. The administration of a conventional rhGAA where most of the rhGAA is not targeted to muscle cells increases the risk of allergic reaction or induction of immunity to the non-targeted rhGAA.

Figure 4:
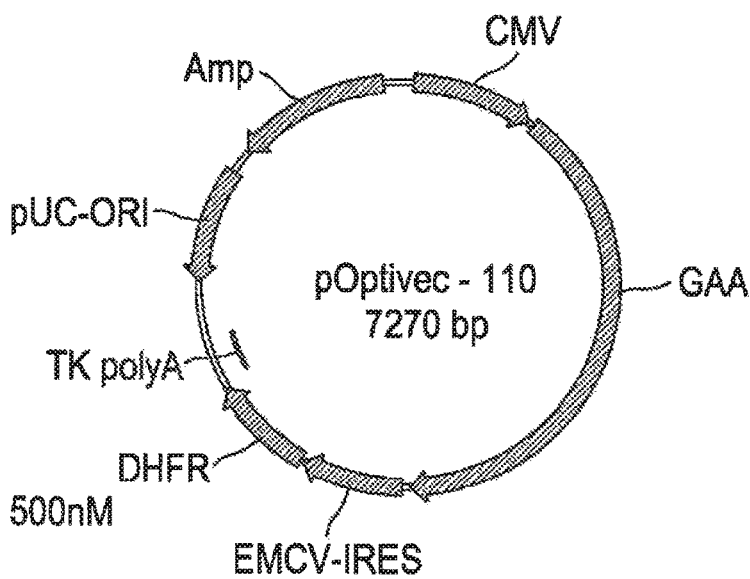
FIG. 4 shows a DNA construct for transforming CHO cells with DNA encoding rhGAA. CHO cells were transformed with a DNA construct encoding rhGAA.
Figure 5A:
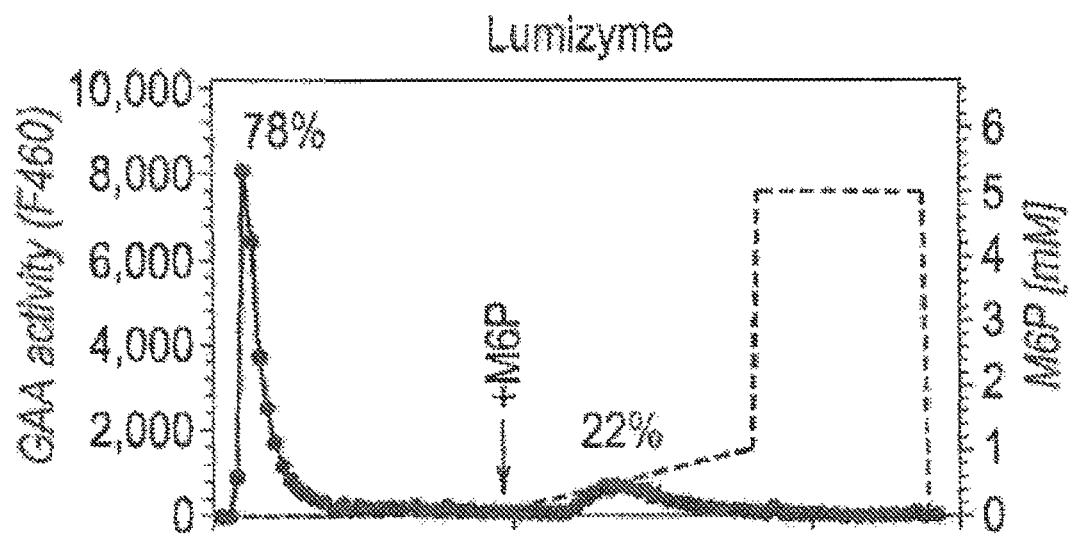
FIGS. 5A and 5B, respectively, are graphs showing the results of CIMPR affinity chromatography of Myozyme® and ATB200 rhGAA. As apparent from FIG. 5B, about 70% of the rhGAA in ATB200 rhGAA contained M6P.
Figure 5B:
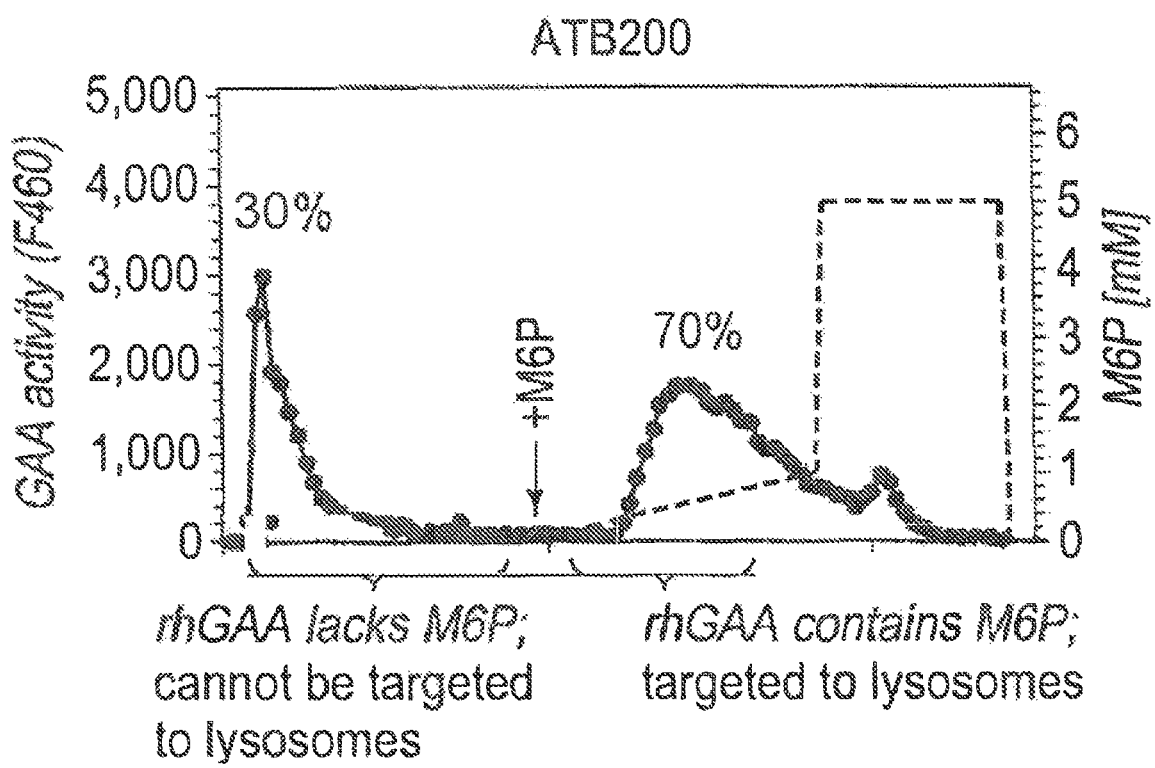

Enzyme Example 2: Preparation of Cho Cells Producing AtB200 rhGAA Having a High Content of Mono- or Bis-M6P-Bearing N-Glycans CHO cells were transfected with DNA that expresses rhGAA followed by selection of transformants producing rhGAA. A DNA construct for transforming CHO cells with DNA encoding rhGAA is shown in FIG. 4. CHO cells were transfected with DNA that expresses rhGAA followed by selection of transformants producing rhGAA.

After transfection, DG44 CHO (DHFR-) cells containing a stably integrated GAA gene were selected with hypoxanthine/thymidine deficient (-HT) medium. Amplification of GAA expression in these cells was induced by methotrexate treatment (MTX, 500 nM). Cell pools that expressed high amounts of GAA were identified by GAA enzyme activity assays and were used to establish individual clones producing rhGAA. Individual clones were generated on semisolid media plates, picked by ClonePix system, and were transferred to 24-deep well plates. The individual clones were assayed for GAA enzyme activity to identify clones expressing a high level of GAA. Conditioned media for determining GAA activity used a 4-MU-α-Glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB-200, expressing rhGAA with enhanced mono-M6P or bis-M6P N-glycans were isolated using this procedure.

Enzyme Example 3: Capturing and Purification of ATB200 rhGAA

Figure 6:
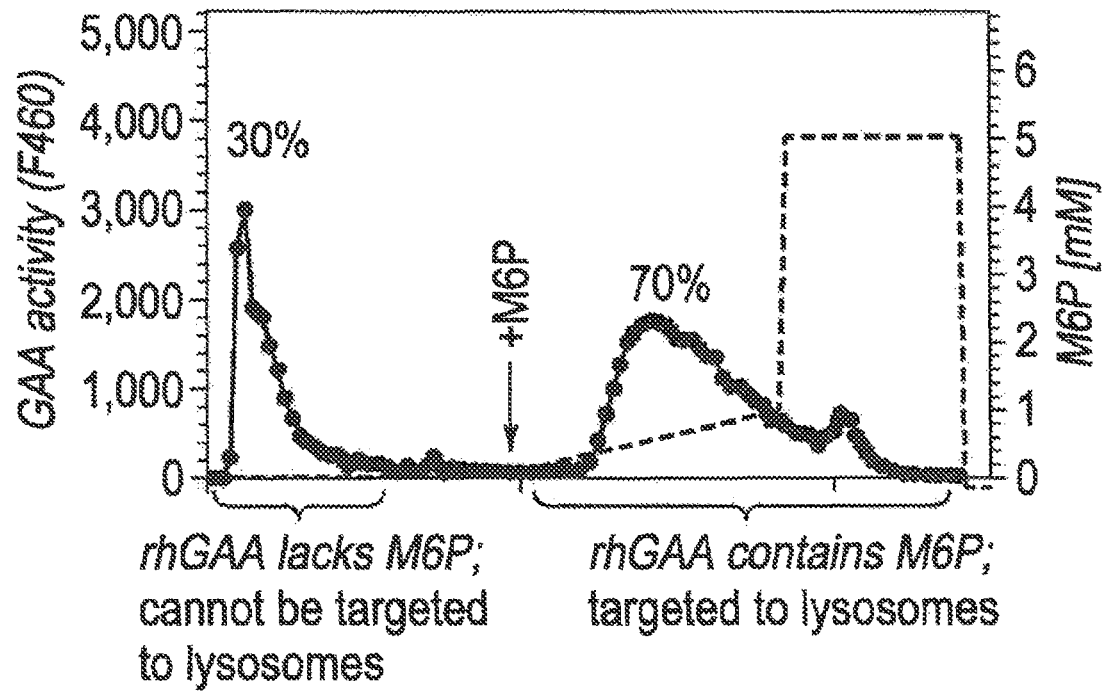
FIG. 6 is a graph showing the results of CIMPR affinity chromatography of ATB200 rhGAA with and without capture on an anion exchange (AEX) column.
Figure 6:
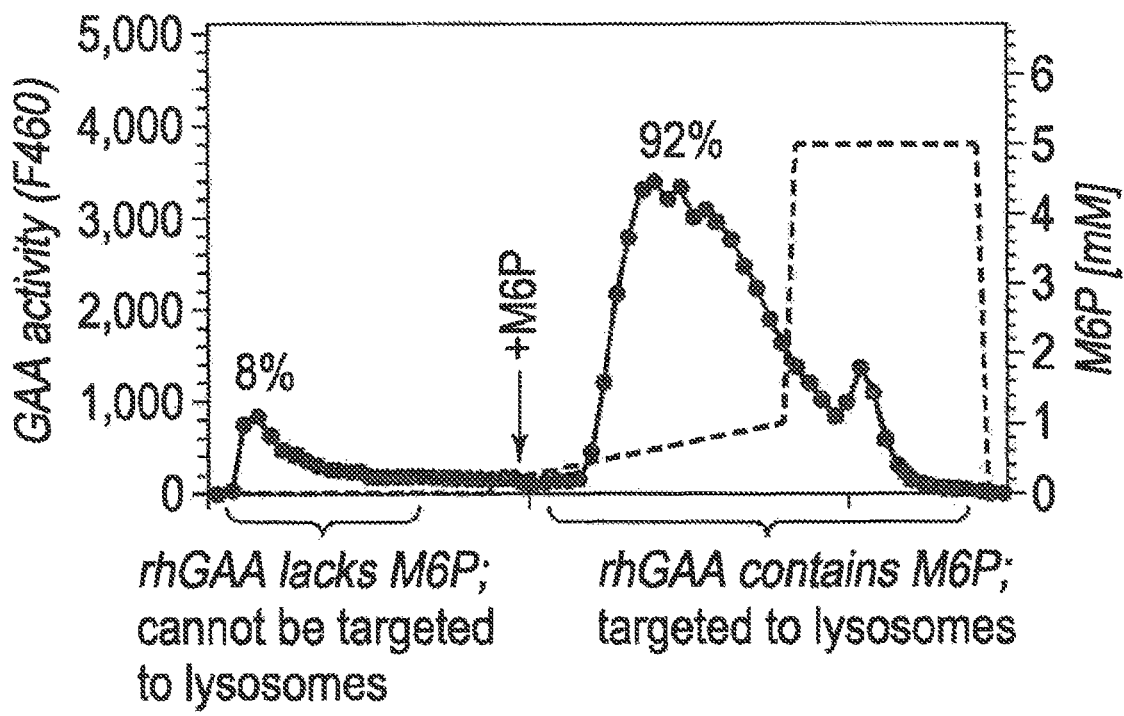

Multiple batches of the rhGAA according to the invention were produced in shake flasks and in perfusion bioreactors using CHO cell line GA-ATB-200 and CIMPR binding was measured. Similar CIMPR receptor binding (~70%) to that shown in FIG. 5B and FIG. 6 was observed for purified ATB200 rhGAA from different production batches indicating that ATB200 rhGAA can be consistently produced. As shown by FIGS. 3A-3B and 5A-5B, Myozyme® and Lumizyme® rhGAAs exhibited significantly less CIMPR binding than ATB200 rhGAA.

Enzyme Example 4: Analytical Comparison of ATB200 to Lumizyme®

Figure 7:
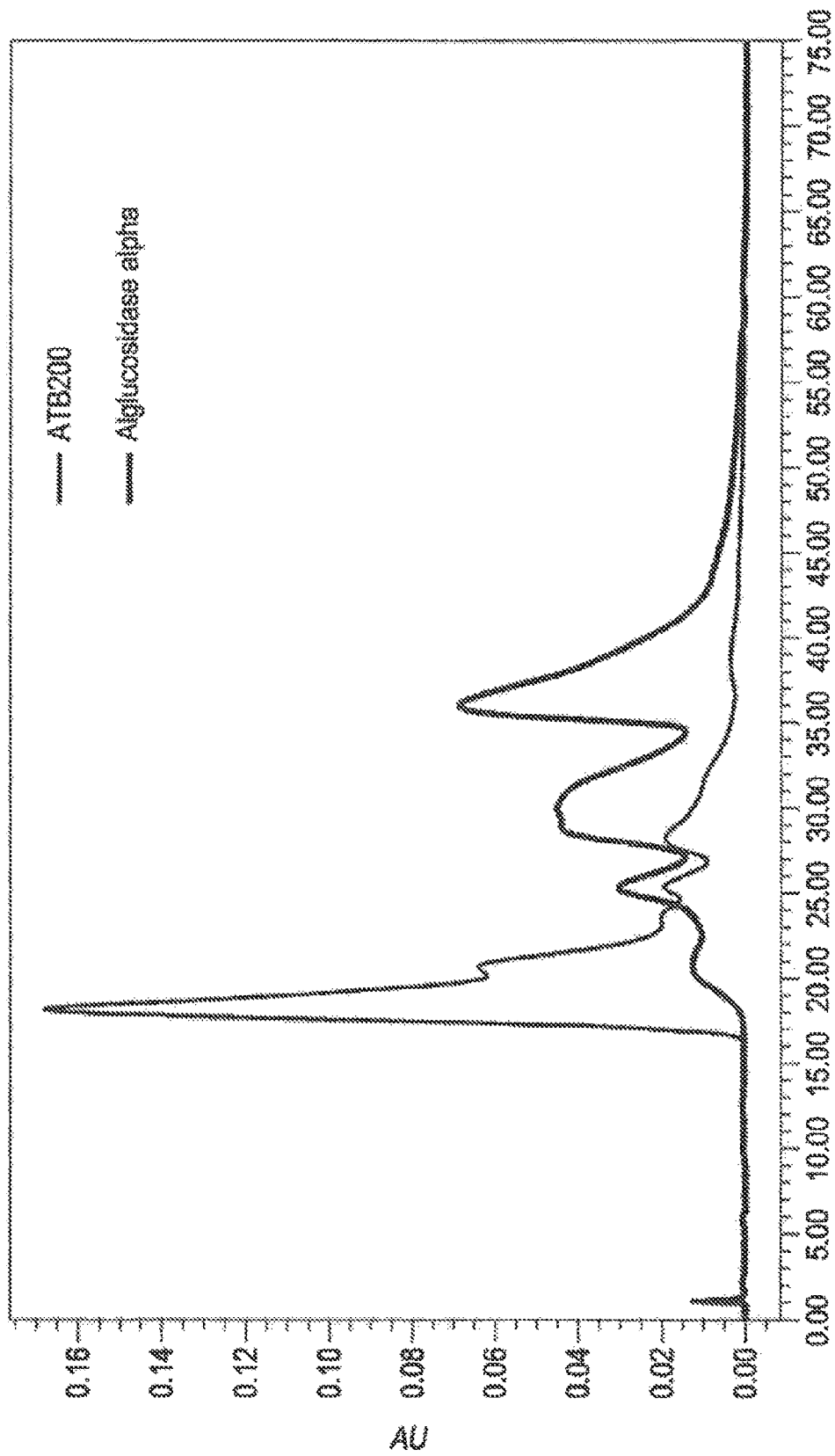
FIG. 7 is a graph showing Polywax elution profiles of Lumizyme® and ATB200 rhGAAs.

Weak anion exchange ("WAX") liquid chromatography was used to fractionate ATB200 rhGAA according to terminal phosphate. Elution profiles were generated by eluting the ERT with increasing amount of salt. The profiles were monitored by UV (A280 nm). ATB200 rhGAA was obtained from CHO cells and purified. Lumizyme® was obtained from a commercial source. Lumizyme® exhibited a high peak on the left of its elution profile. ATB200 rhGAA exhibited four prominent peaks eluting to the right of Lumizyme® (FIG. 7). This confirms that ATB200 rhGAA was phosphorylated to a greater extent than Lumizyme® since this evaluation is by terminal charge rather than CIMPR affinity.

Enzyme Example 5: Oligosaccharide Characterization of ATB200 rhGAA

Figures 10A, 10B:
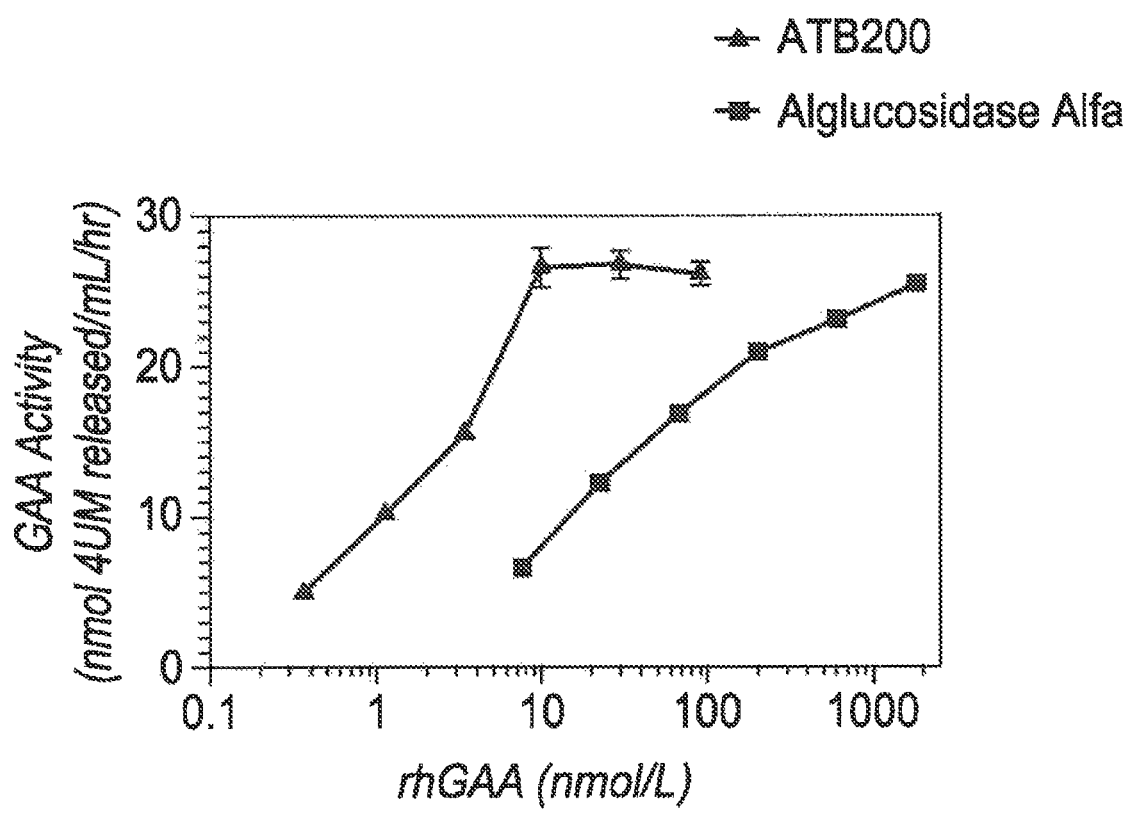
FIG. 10A is a graph comparing the CIMPR binding affinity of ATB200 rhGAA (left trace) with that of Lumizyme® (right trace).
FIG. 10B is a table comparing the Bis-M6P content of Lumizyme® and ATB200 rhGAA.

Purified ATB200 rhGAA and Lumizyme® glycans were evaluated by MALDI-TOF to determine the individual glycan structures found on each ERT (FIG. 8). ATB200 samples were found to contain lower amounts of non-phosphorylated high-mannose type N-glycans than Lumizyme®. The higher content of M6P glycans in ATB200 than in Lumizyme®, targets ATB200 rhGAA to muscle cells more effectively. The high percentage of mono-phosphorylated and bis-phosphorylated structures determined by MALDI agree with the CIMPR profiles which illustrated significantly greater binding of ATB200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB200 rhGAA directly correlated with high-affinity binding to CIMPR in M6P receptor plate binding assays (KD about 2-4 nM) (FIG. 10A).

ATB200 rhGAA was also analyzed for site-specific N-glycan profiles using two different LC-MS/MS analytical techniques. In the first analysis, the protein was denatured, reduced, alkylated and digested prior to LC-MS/MS analysis. During protein denaturation and reduction, 200 µg of protein sample, 5 µL 1 mol/L tris-HCl (final concentration 50 mM), 75 µL 8 mol/L guanidine HCl (final concentration 6 M), 1 µL 0.5 mol/L EDTA (final concentration 5 mM), 2 µL 1 mol/L DTT (final concentration 20 mM) and Milli-Q® water were added to a 1.5 mL tube to provide a total volume of 100 µL. The sample was mixed and incubated at 56° C. for 30 minutes in a dry bath. During alkylation, the denatured and reduced protein sample was mixed with 5 µL 1 mol/L iodoacetamide (IAM, final concentration 50 mM), then incubated at 10-30° C. in the dark for 30 minutes. After alkylation, 400 µL of precooled acetone was added to the sample and the mixture was frozen at −80° C. refrigeration for 4 hours. The sample was then centrifuged for 5 min at 13000 rpm at 4° C. and the supernatant was removed. 400 µL of precooled acetone was added to the pellets, which was then centrifuged for 5 min at 13000 rpm at 4° C. and the supernatant was removed. The sample was then air dried on ice in the dark to remove acetone residue. 40 µL of 8M urea and 160 µL of 100 mM $NH_4HCO_3$ were added to the sample to dissolve the protein. During trypsin digestion, 50 µg of the protein was then added with trypsin digestion buffer to a final volume of 100 µL, and 5 µL 0.5 mg/mL trypsin (protein to enzyme ratio of 20/1 w/w) was added. The solution was mixed well and incubated overnight (16±2 hours) at 37° C. 2.5 µL 20% TFA (final concentration 0.5%) was added to quench the reaction. The sample was then analyzed using the Thermo Scientific Orbitrap Velos Pro' Mass Spectrometer.

In the second LC-MS/MS analysis, the ATB200 sample was prepared according to a similar denaturation, reduction, alkylation and digestion procedure, except that iodoacetic acid (IAA) was used as the alkylation reagent instead of IAM, and then analyzed using the Thermo Scientific Orbitrap Fusion Lumos Tribid™ Mass Spectrometer.

The results of the first and second analyses are shown in FIGS. 9A-9H. In FIGS. 9A-9H, the results of the first analysis are represented by left bar (dark grey) and the results from the second analysis are represented by the right bar (light grey). In FIGS. 9B-9G, the symbol nomenclature for glycan representation is in accordance with Varki, A., Cummings, R. D., Esko J. D., et al., *Essentials of Glycobiology*, 2nd edition (2009).

Figure 9A:
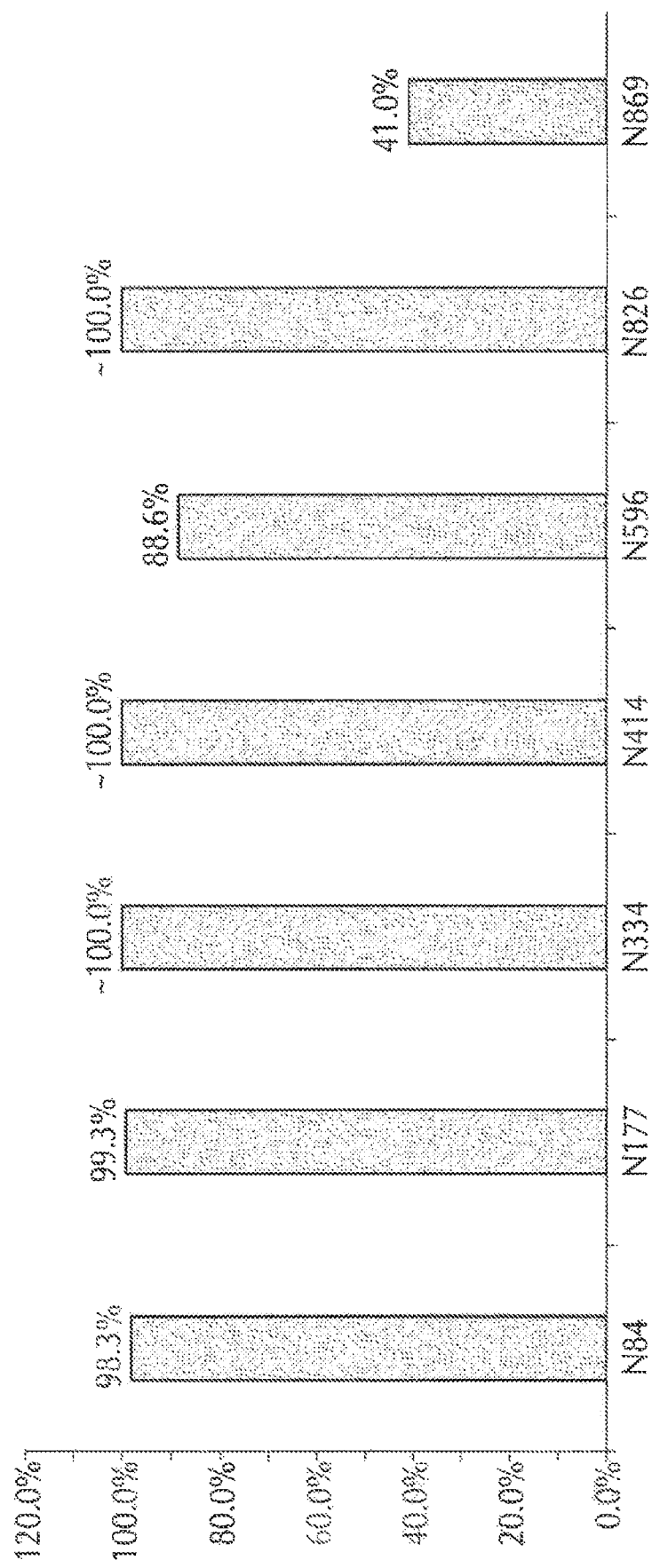
FIGS. 9A-9H show the results of a site-specific N-glycosylation analysis of ATB200 rhGAA.

As can be seen from FIGS. 9A-9G, the two analyses provided similar results, although there was some variation between the results. This variation can be due to a number of factors, including the instrument used and the completeness of N-glycan analysis. For example, if some species of phosphorylated glycans were not identified and/or not quantified, then the total number of phosphorylated glycans may be underrepresented, and the percentage of rhGAA bearing the phosphorylated glycans at that site may be underrepresented. As another example, if some species of non-phosphorylated glycans were not identified and/or not quantified, then the total number of non-phosphorylated glycans may be underrepresented, and the percentage of rhGAA bearing the phosphorylated glycans at that site may be overrepresented. FIG. 9A shows the N-glycosylation site occupancy of ATB200. As can be seen from FIG. 9A, the first, second, third, fourth, fifth and sixth N-glycosylation sites are mostly occupied, with both analyses detecting over 90% and up to about 100% of the ATB200 enzyme having a glycan detected at each potential site. However, the seventh potential N-glycosylation site is glycosylated about half of the time.

Figure 9B:
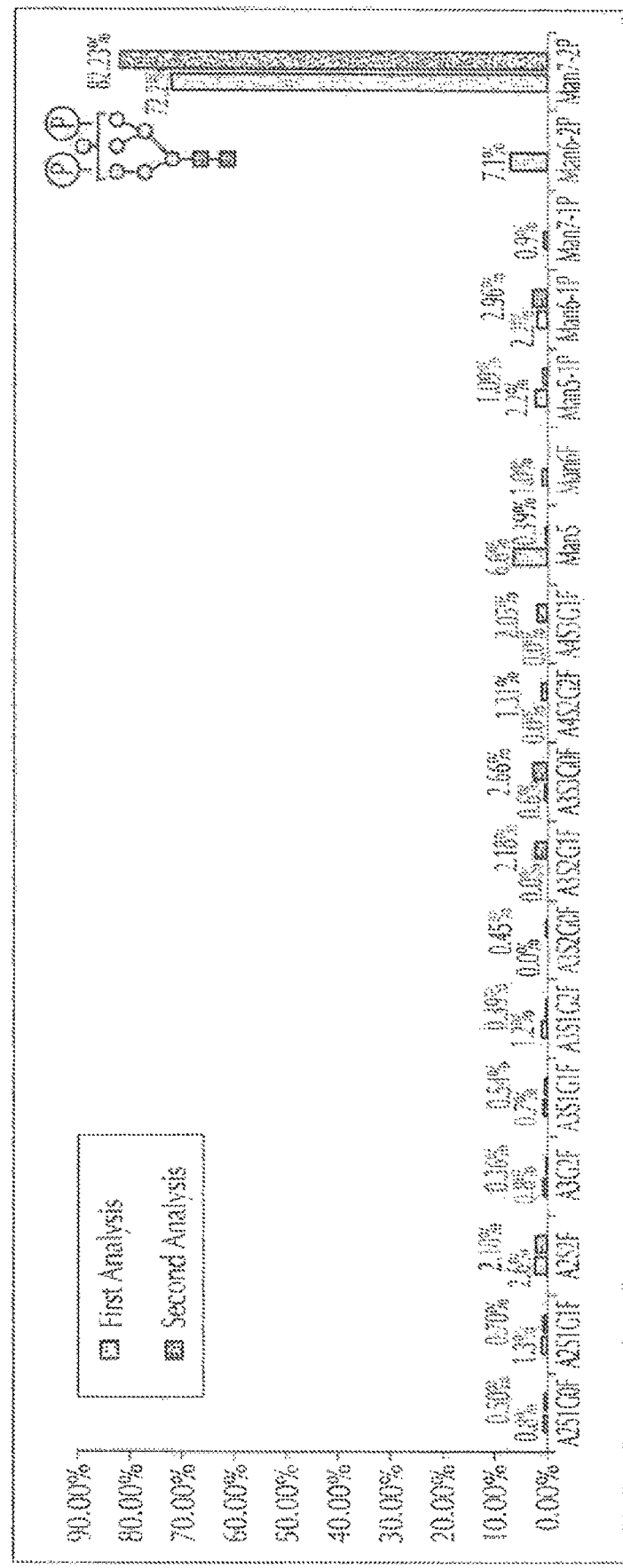

FIG. 9B shows the N-glycosylation profile of the first site, N84. As can be seen from FIG. 9B, the major glycan species is bis-M6P glycans. Both the first and second analyses detected over 75% of the ATB200 had a bis-M6P glycan at the first site.

Figure 9C:
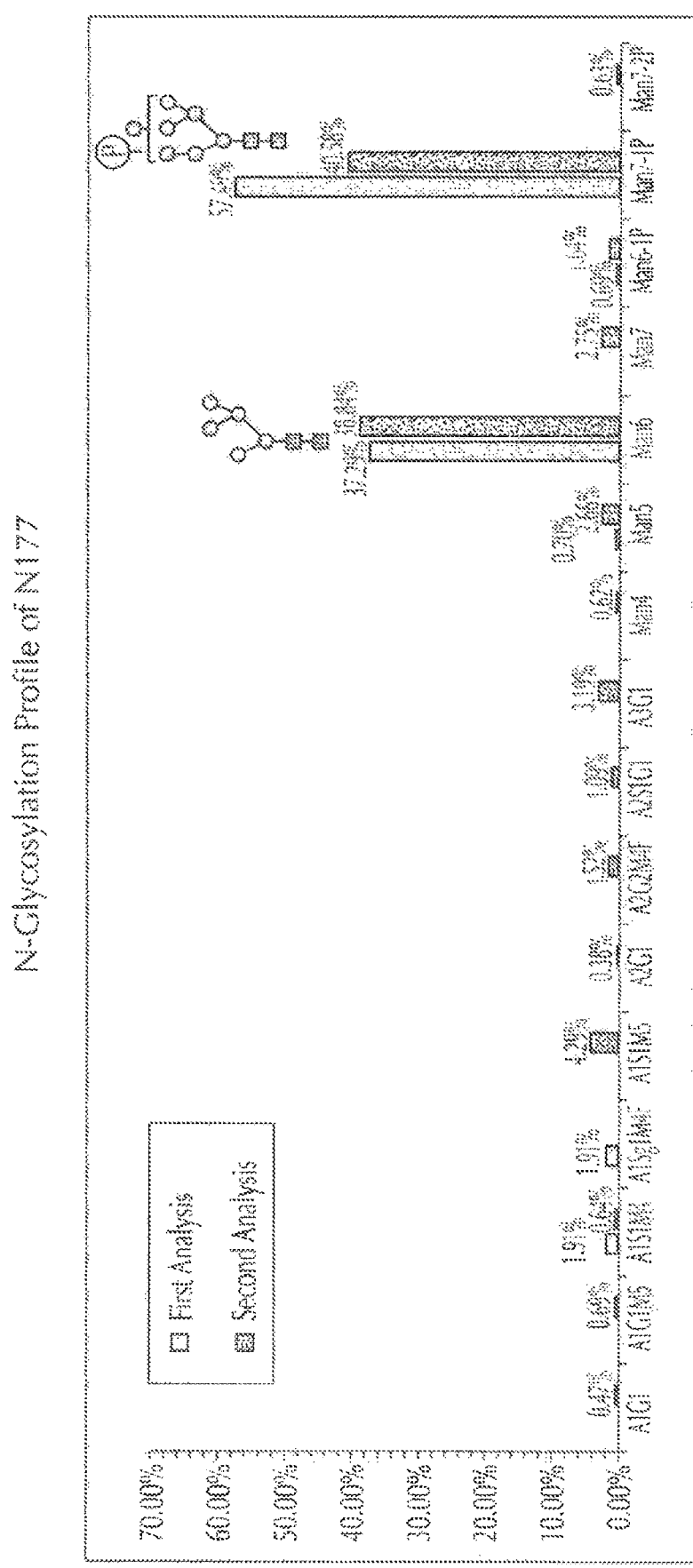

FIG. 9C shows the N-glycosylation profile of the second site, N177. As can be seen from FIG. 9C, the major glycan species are mono-M6P glycans and non-phosphorylated high mannose glycans. Both the first and second analyses detected over 40% of the ATB200 had a mono-M6P glycan at the second site.

Figure 9D:
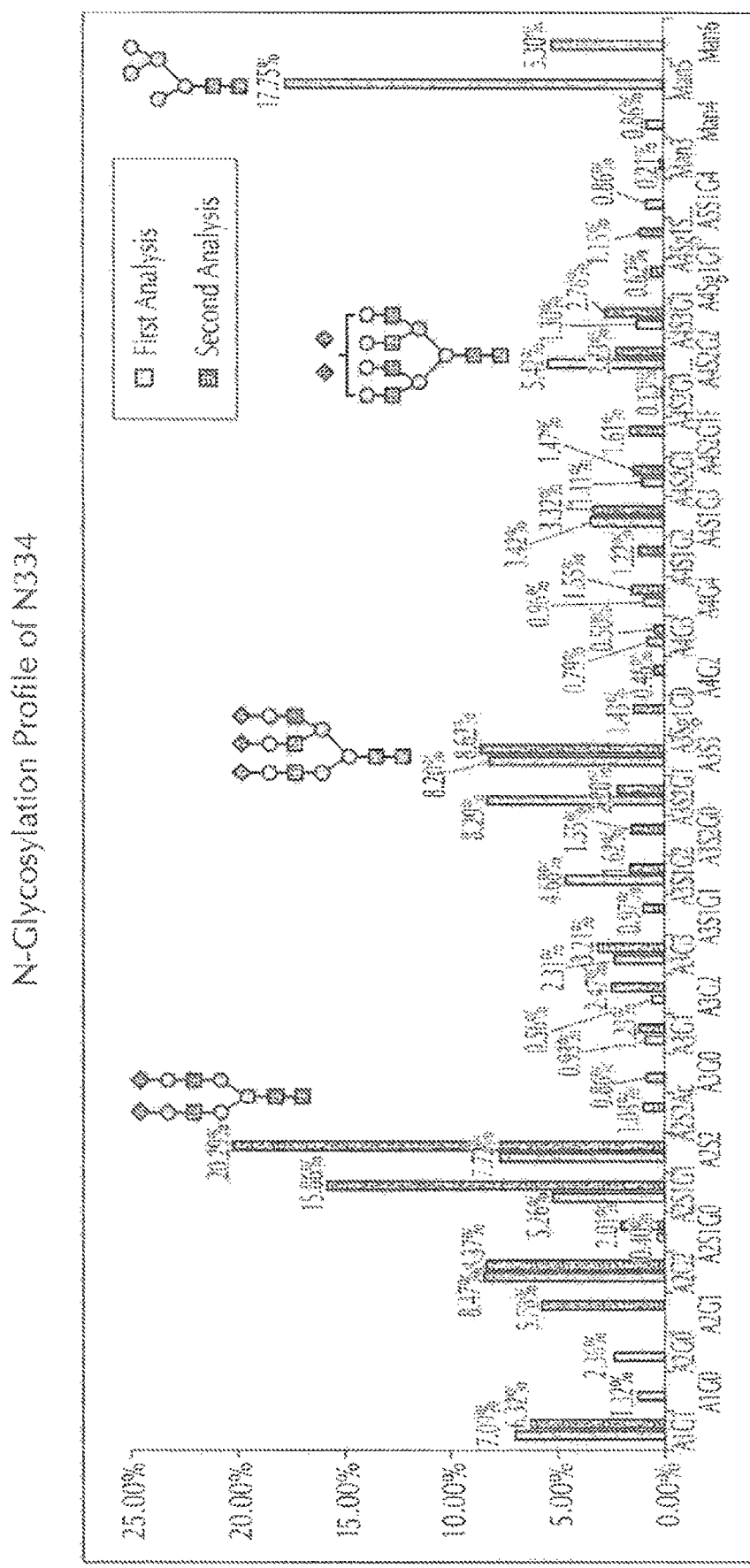

FIG. 9D shows the N-glycosylation profile of the third site, N334. As can be seen from FIG. 9D, the major glycan species are non-phosphorylated high mannose glycans, di-, tri-, and tetra-antennary complex glycans, and hybrid glycans. Both the first and second analyses detected over 20% of the ATB200 had a sialic acid residue at the third site.

Figure 9E:
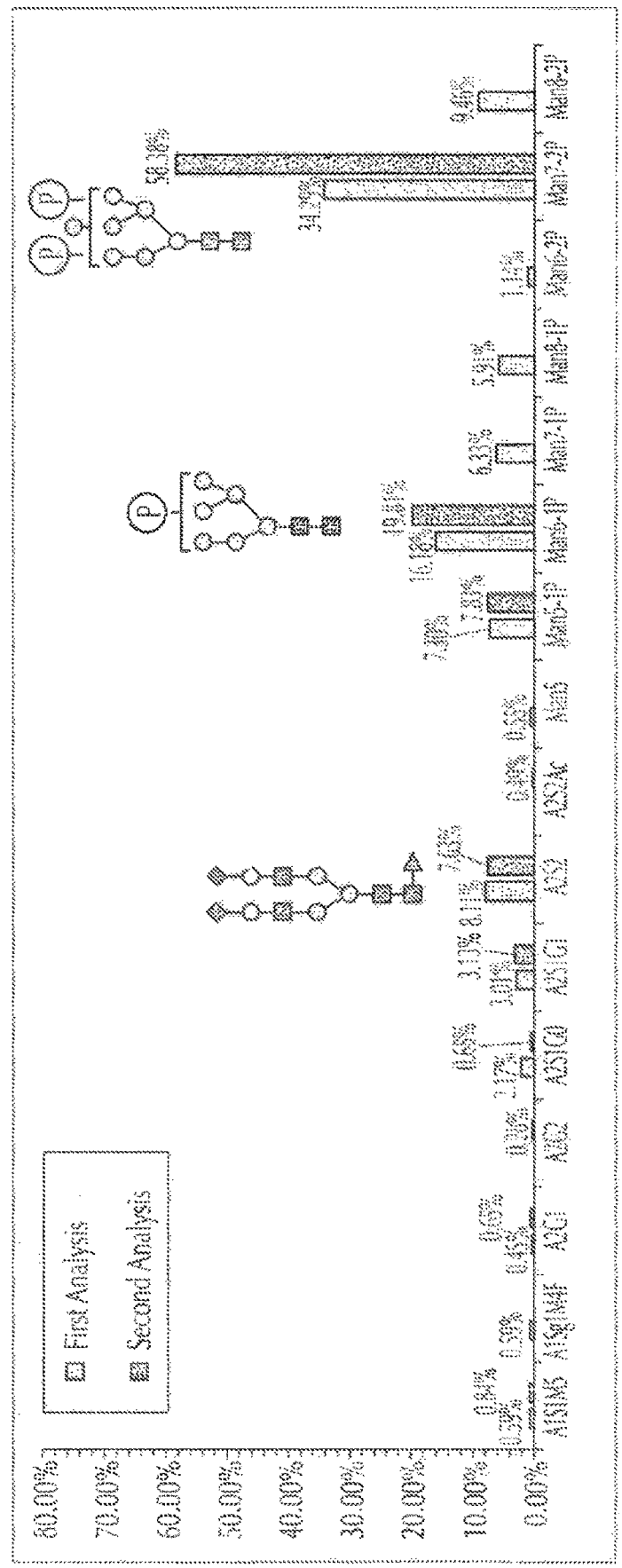

FIG. 9E shows the N-glycosylation profile of the fourth site, N414. As can be seen from FIG. 9E, the major glycan species are bis-M6P and mono-MGP glycans. Both the first and second analyses detected over 40% of the ATB200 had a bis-M6P glycan at the fourth site. Both the first and second analyses also detected over 25% of the ATB200 had a mono-M6P glycan at the fourth site.

Figure 9F:
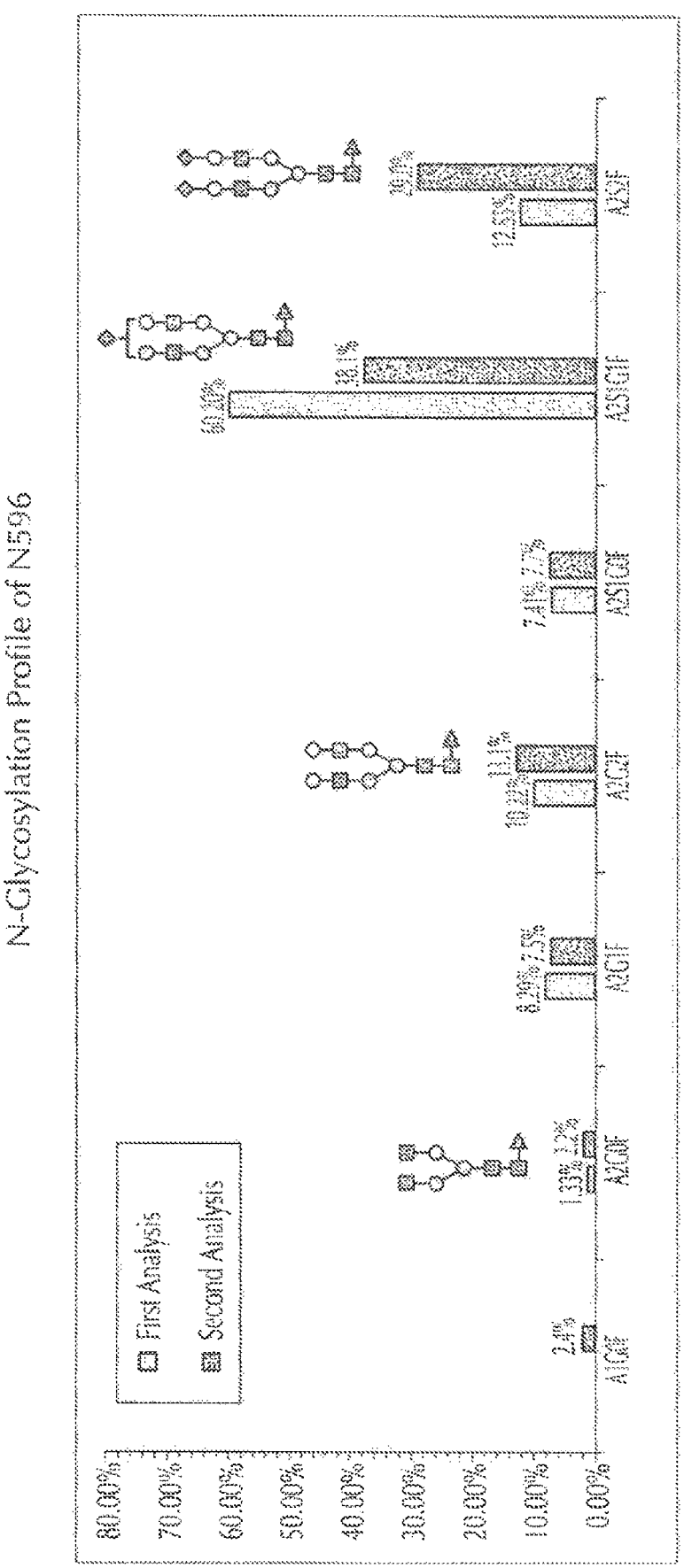

FIG. 9F shows the N-glycosylation profile of the fifth site, N596. As can be seen from FIG. 9F, the major glycan species are fucosylated di-antennary complex glycans. Both the first and second analyses detected over 70% of the ATB200 had a sialic acid residue at the fifth site.

Figure 9G:
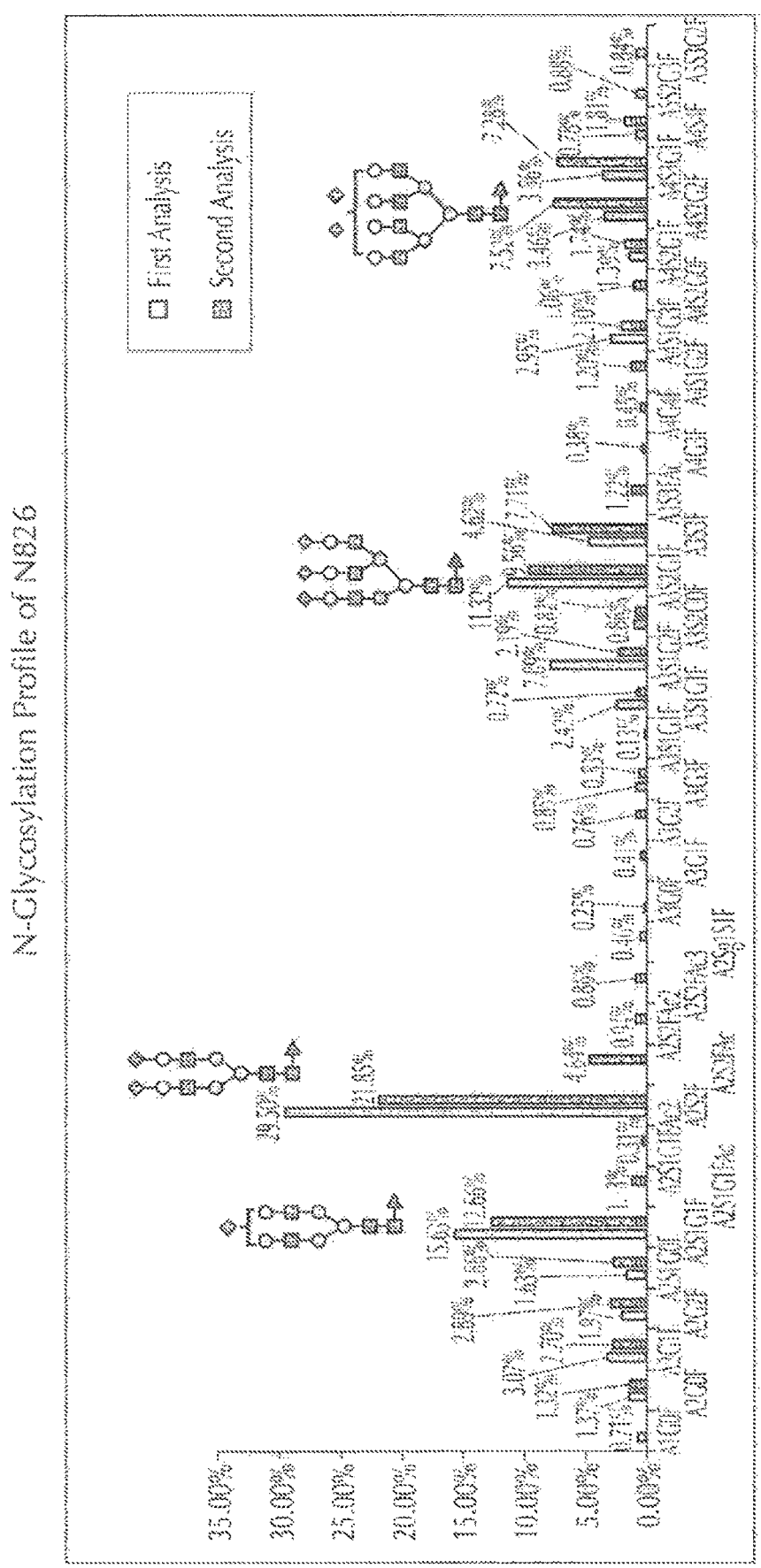

FIG. 9G shows the N-glycosylation profile of the sixth site, N826. As can be seen from FIG. 9G, the major glycan species are di-, tri-, and tetra-antennary complex glycans. Both the first and second analyses detected over 80% of the ATB200 had a sialic acid residue at the sixth site.

An analysis of the glycosylation at the seventh site, N869, showed approximately 40% glycosylation, with the most common glycans being A4S3S3GF (12%), A5S3G2F (10%), A4S2G2F (8%) and A6S3G3F (8%).

Figure 9H:
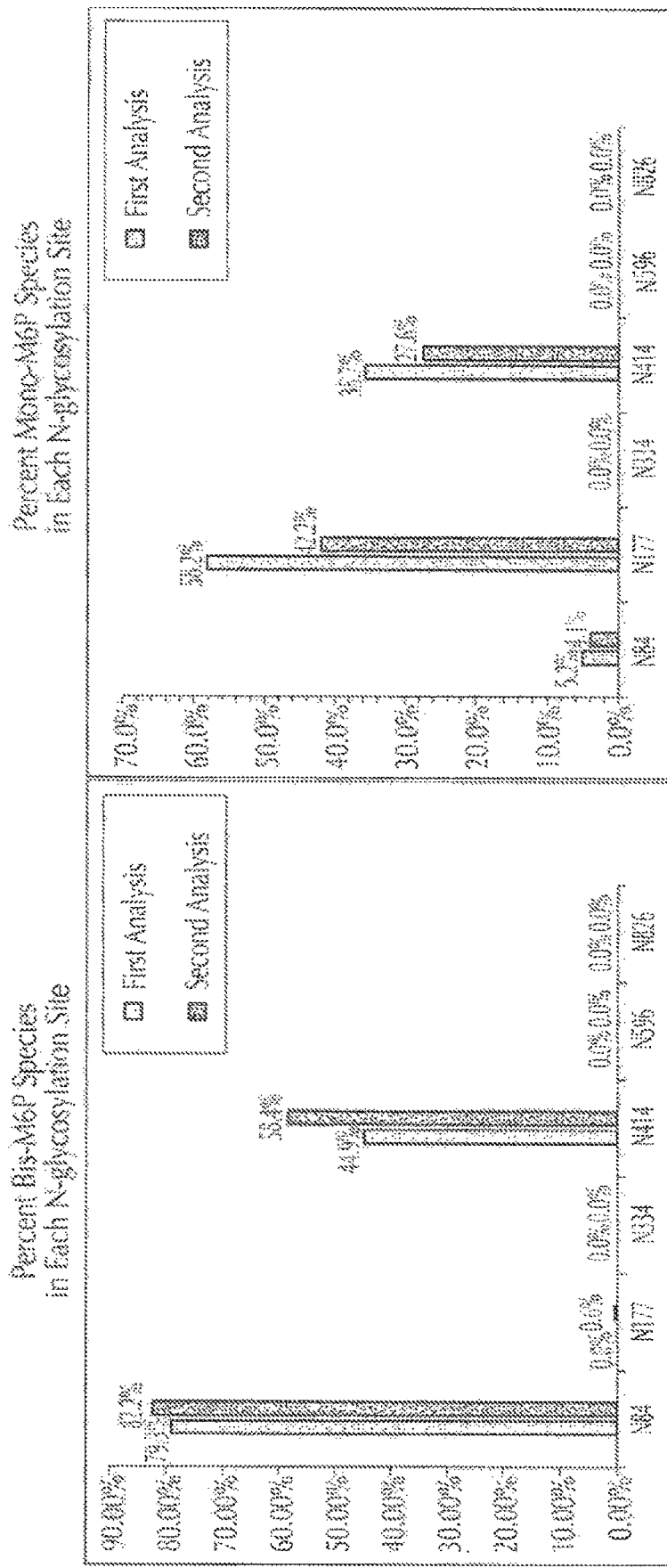

FIG. 9H shows a summary of the phosphorylation at each of the seven potential N-glycosylation sites. As can be seen from FIG. 9H, both the first and second analyses detected high phosphorylation levels at the first, second and fourth sites. Both analyses detected over 80% of the ATB200 was mono- or di-phosphorylated at the first site, over 40% of the ATB200 was mon-phosphorylated at the second site, and over 80% of the ATB200 was mono- or di-phosphorylated at the fourth site.

Another glycan analysis of ATB200 was performed according to a hydrophilic interaction liquid chromatography-fluorescent detection-mass spectrometry (HILIC-FLD-MS) method.

The results of HILIC-FLD-MS analysis are provided in Table A below. In Table A, the first number in the three-digit number indicates the number of branches in the glycan, the second number indicates the number of core fucose units and the third number indicates the number of terminal sialic acid units. Using this nomenclature, "303" represents a tri-antennary glycan (the first 3) with 0 core fucose (the 2nd 0) and 3 terminal sialic acids (the last 3), "212" represents a bi-antennary glycan with 1 core fucose and 2 terminal sialic acids, "404" represents a tetra-antennary glycan with 0 core fucose and 4 terminal sialic acids, etc.

TABLE A

| FLD Peak Number | MS Peak Number | RT (min) | Glycan Structure | % Peak Area |
|---|---|---|---|---|
| 1 | 1 | | BisP_Man 8 | 2.83% |
| 2 | 2 | 13.41 | BisP_Man 7 | 17.58% |
| | 3 | 14.30 | BisP_Man 6 | 1.02% |
| 3 | 4 | 20.89 | MonoP_Man 6 | 2.34% |
| 4 | 5 | 21.65 | MonoP_Man 5 | 1.16% |
| 5 | 6 | 23.51 | MonoP_Man 8 | 1.28% |
| 6 | 7 | 24.33 | MonoP_Man 7 | 4.35% |
| 7 | 8 | 25.61 | MonoP_Man 7_(+)GlcNAc | 0.50% |
| 8 | 9 | 28.76 | MonoP_hMan6_101 | 0.48% |
| 9 | 10 | 30.54 | MonoP_Man 6_(+)GlcNAc | 0.68% |
| 10 | 11 | 33.50 | Man 6 | 3.97% |
| | 12 | 33.65 | 303 | 0.74% |
| 11 | 13 | 34.97 | Man 7 | 0.20% |
| 12 | 14 | 35.64 | 403 | 0.39% |
| 13 | 15 | 36.61 | 302 | 0.36% |
| 14 | 16 | 38.07 | 302 | 0.61% |
| 15 | 17 | 38.53 | Man 5 | 1.85% |
| 16 | 18 | 39.57 | 302 | 0.48% |
| | 19 | 39.78 | hMan 5_101 | 0.42% |
| | 20 | 40.05 | hMan 5_100_(-)Gal | 0.30% |
| 17 | 21 | 40.77 | 301_(-)Gal | 0.52% |
| | 22 | 40.58 | 301 | 0.50% |
| 18 | 23 | 41.47 | 300_(-)Gal | 0.80% |
| 19 | 24 | 42.17 | 301_(-)Gal | 0.11% |
| | 25 | 42.13 | 301 | 0.58% |
| 20 | 26 | 42.89 | 301_(-)Gal | 0.07% |
| | 27 | 42.79 | 301 | 0.80% |
| 21 | 28 | 43.41 | 300 | 0.85% |
| | 29 | 43.28 | 101 | 0.39% |
| 22 | 30 | 43.94 | 202 | 0.63% |
| 23 | 31 | 44.45 | 401 | 0.39% |
| 24 | 32 | 45.04 | MonoP_hMan6_111 | 0.36% |
| 25 | 33 | 45.69 | MonoP_hMan6_111 | 1.45% |
| | 34 | 45.90 | 100 | 0.23% |
| | 35 | 45.90 | 400 | 0.19% |
| 26 | 36 | 46.87 | 201 | 0.49% |
| | 37 | 47.15 | 202 | 0.34% |
| 27 | 38 | 48.19 | 414 | 0.37% |
| 28 | 39 | 48.94 | 202 | 1.97% |
| 29 | 40 | 50.79 | MonoP_Man 6_110_(-)Gal | 1.31% |
| | 41 | 51.37 | 414 | 0.62% |
| 30 | 42 | 52.22 | 313 | 0.74% |
| | 43 | 52.42 | 201_(-)Gal | 0.46% |
| | 44 | 52.42 | 201 | 1.18% |
| | 45 | 53.11 | hMan6_111 | 0.20% |
| 31 | 46 | 53.83 | 200_(-)Gal | 0.80% |
| | 47 | 54.23 | 201 | 1.27% |
| | 48 | 54.75 | 413 | 0.30% |
| 32 | 49 | 55.47 | 200 | 1.30% |
| 33 | 50 | 57.45, 58.34 | 414_(+)GlcNAcGal | 0.14% |
| | 51 | 56.62, 56.91, 57.99 | 413 | 0.94% |
| | 52 | 56.11, 57.26, 57.99 | 312 | 0.98% |
| 34 | 53 | 60.19 | 413 | 0.33% |
| | 54 | 59.39 | 413_(+)GlcNAcGal | 0.42% |
| | 55 | 59.80 | 312 | 0.52% |
| | 56 | 59.49 | 412 | 0.18% |
| 35 | 57 | 60.75 | 413 | 0.78% |
| | 58 | 60.89 | 413_(+)GlcNAcGal | 0.07% |
| 36 | 59 | 61.79 | 413 | 0.20% |
| | 60 | 61.75 | 312 | 0.16% |
| | 61 | 62.12 | 412 | 0.64% |
| 37 | 62 | 63.87 | 311 | 0.73% |
| | 63 | 63.18, 64.32 | 412 | 0.29% |
| | 64 | 63.84 | 413_(+)GlcNAcGal | 0.45% |
| | 65 | 63.5, 64.36 | 311_(-)Gal | 0.42% |
| 38 | 66 | 65.73, 66.20 | 311 | 0.68% |
| | 67 | 65.85, 66.49 | 412 | 0.72% |
| | 68 | 65.91 | 310_(-)Gal | 0.28% |
| 39 | 69 | 67.37 | 212 | 1.42% |
| | 70 | 67.57 | 310 | 0.34% |
| 40 | 71 | 68.67 | 412_(+)GlcNAcGal | 0.24% |
| | 72 | 68.36 | 412 | 0.53% |
| 41 | 73 | 68.36 | 412_(+)GlcNAcGal | 0.17% |
| | 74 | 69.03 | 412 | 0.35% |
| | 75 | 69.30 | 413_(+)2(GlcNAcGal) | 0.16% |
| 42 | 76 | 70.66 | 412_(+)GlcNAcGal | 0.73% |
| 43 | 77 | 71.74 | 211 | 1.09% |
| | 78 | 71.23 | 211_(-)Gal | 0.19% |
| 44 | 79 | 72.46 | 212 | 3.66% |
| 45 | 80 | 74.82 | 221_(-)Gal(+)GalNAc | 0.38% |
| | 81 | 74.43, 74.96 | 411_(+)GlcNAcGal | 0.66% |
| 46 | 82 | 75.92 | 410 | 0.42% |
| 47 | 83 | 76.73, 77.87 | 211_(-)Gal | 1.24% |
| | 84 | 77.23 | 211 | 3.64% |
| 48 | 85 | 79.05 | 211 | 1.52% |
| | 86 | 79.38 | 210_(-)2Gal | 0.45% |
| 49 | 87 | 80.11 | 210_(-)Gal | 1.58% |
| 50 | 88 | 81.15 | 210 | 2.41% |
| 51 | 89 | 84.22-87.15 | 311 | 1.26% |
| 52 | 90 | 95.35 | Mono_Acetyl_NANA_212 | 0.99% |
| 53 | 91 | 96.23 | Mono_Acetyl_NANA_211 | 0.76% |
| 54 | 92 | 97.37 | Bis_Acetyl_NANA_212 | 0.42% |

Based on this HILIC-FLD-MS analysis, the ATB200 tested is expected to have an average fucose content of 2-3 mol per mol of ATB200, GlcNAc content of 20-25 mol per mol of ATB200, galactose content of 8-12 mol per mol of ATB200, mannose content of 22-27 mol per mol of ATB200, M6P content of 3-5 mol per mol of ATB200 and sialic acid content of 4-7 mol of ATB200.

Enzyme Example 6: Characterization of CIMPR Affinity of ATB200

In addition to having a greater percentage of rhGAA that can bind to the CIMPR, it is important to understand the quality of that interaction. Lumizyme® and ATB200 rhGAA receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown by FIG. 10A, ATB200 rhGAA bound to CIMPR significantly better than Lumizyme®.

FIG. 10B shows the relative content of bis-M6P glycans in Lumizyme®, a conventional rhGAA, and ATB200 according to the invention. For Lumizyme® there is on average only 10% of molecules have a bis-phosphorylated glycan. Contrast this with ATB200 where on average every rhGAA molecule has at least one bis-phosphorylated glycan.

Enzyme Example 7: ATB200 RhGAA was More Efficiently Internalized by Fibroblast than Lumizyme®

The relative cellular uptake of ATB200 and Lumizyme® rhGAA were compared using normal and Pompe fibroblast cell lines. Comparisons involved 5-100 nM of ATB200 rhGAA according to the invention with 10-500 nM conventional rhGAA Lumizyme®. After 16-hr incubation, external rhGAA was inactivated with TRIS base and cells were washed 3-times with PBS prior to harvest. Internalized GAA measured by 4MU-$\alpha$-Glucoside hydrolysis and was graphed relative to total cellular protein and the results appear in FIGS. 11A-11B.

ATB200 rhGAA was also shown to be efficiently internalized into cells (FIGS. 11A and 11B), respectively, show that ATB200 rhGAA is internalized into both normal and Pompe fibroblast cells and that it is internalized to a greater degree than conventional Lumizyme® rhGAA. ATB200 rhGAA saturates cellular receptors at about 20 nM, while about 250 nM of Lumizyme® is needed. The uptake efficiency constant ($K_{uptake}$) extrapolated from these results is 2-3 nm for ATB200 and 56 nM for Lumizyme® as shown by FIG. 11C. These results suggest that ATB200 rhGAA is a well-targeted treatment for Pompe disease.

Enzyme Example 8: Glycogen Reduction in Gaa-Knockout Mice

Figure 12A:
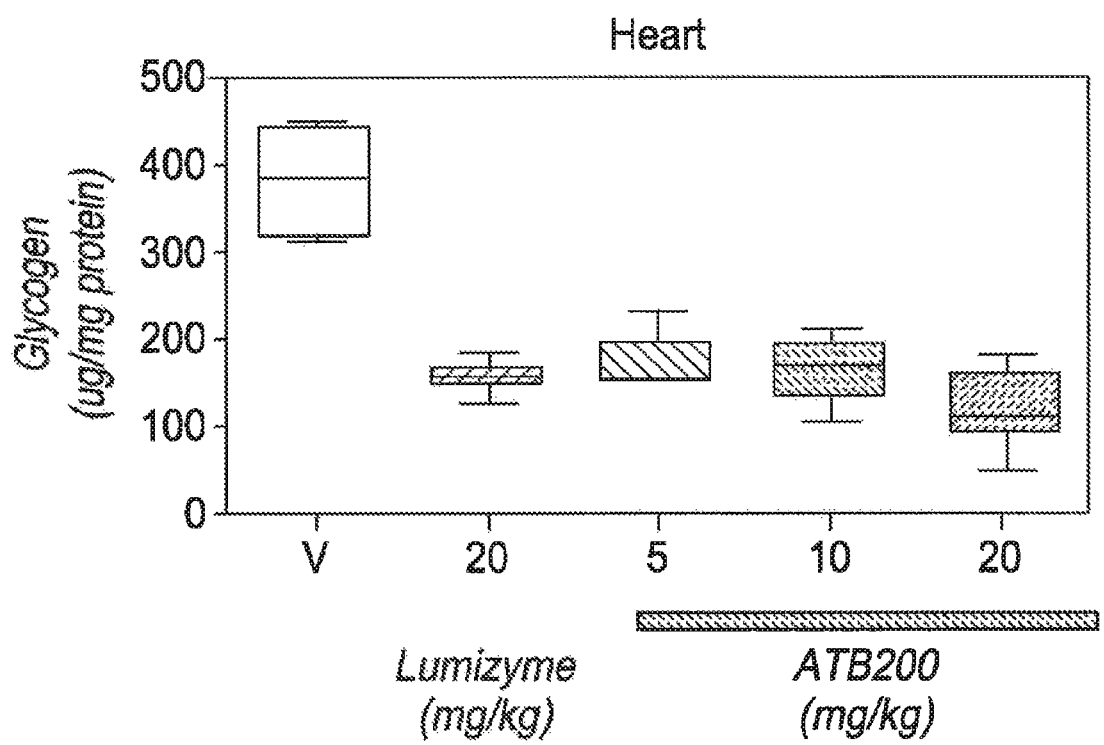
FIG. 12A is a graph showing the amount of glycogen relative to dose of recombinant human acid α-glucosidase in mouse heart muscle after contact with vehicle (negative control), with 20 mg/ml alglucosidase alfa (Lumizyme®), or with 5, 10 or 20 mg/kg ATB200.
Figure 12B:
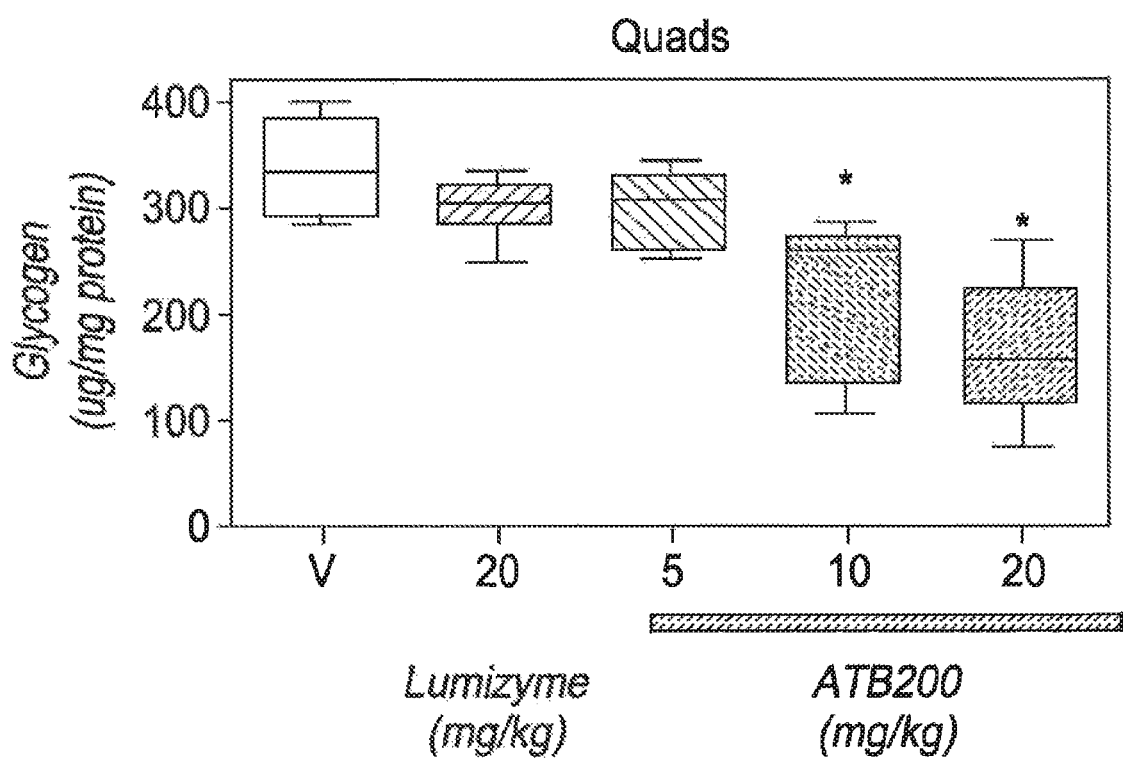
FIG. 12B is a graph showing the amount of glycogen relative to dose of recombinant human acid α-glucosidase in mouse quadriceps muscle after contact with vehicle (negative control), with 20 mg/ml alglucosidase alfa (Lumizyme®), or with 5, 10 or 20 mg/kg ATB200.
Figures 12C, 13:
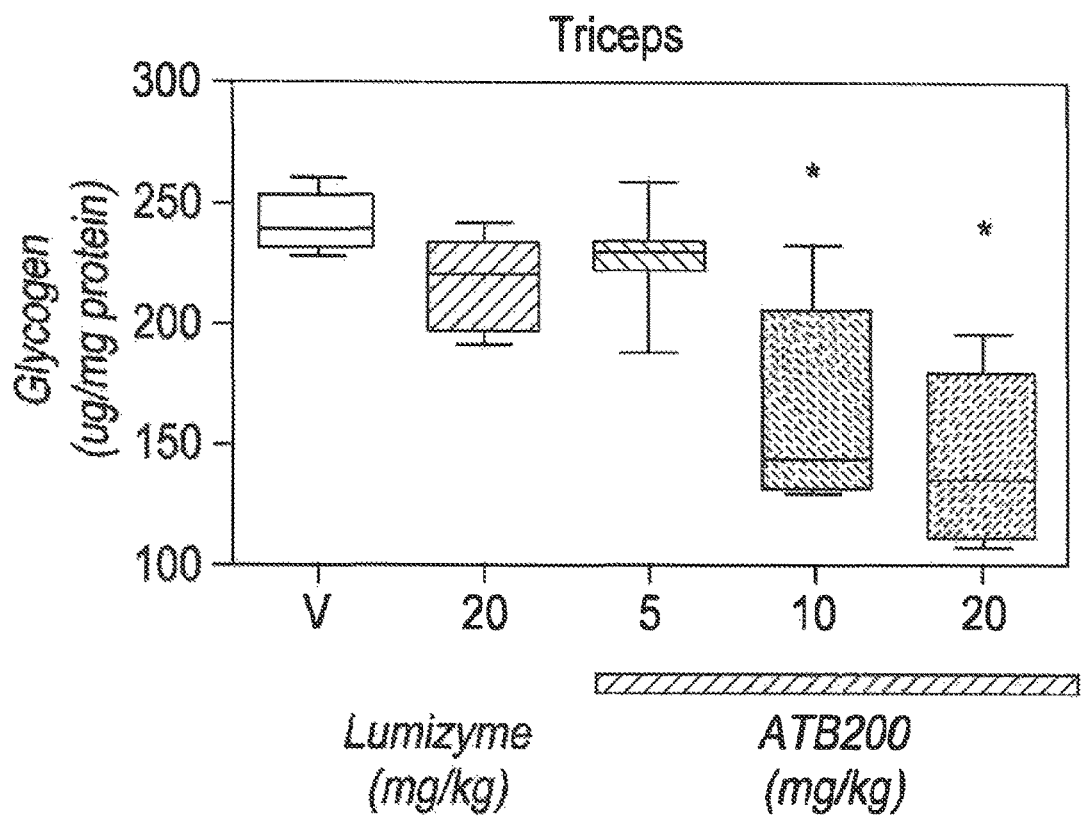
FIG. 12C is a graph showing the amount of glycogen relative to dose of recombinant human acid α-glucosidase in mouse triceps muscle after contact with vehicle (negative control), with 20 mg/ml alglucosidase alfa (Lumizyme®), or with 5, 10 or 20 mg/kg ATB200.
FIG. 13 is a table showing that the combination of ATB200 rhGAA and chaperone miglustat provided significantly better glycogen clearance in GAA knock-out mice than treatments with either Lumizyme® or ATB200 rhGAAs without the miglustat chaperone.

FIGS. 12A to 12C show the effects of administering alglucosidase alfa (Lumizyme®) and ATB200 on glycogen clearance in Gaa knockout mice. Animals were given two IV bolus administrations (every other week); tissues were harvested two weeks after the last dose and analyzed for acid $\alpha$-glucosidase activity and glycogen content.

As seen from FIGS. 12A to 12C, ATB200 was found to deplete tissue glycogen in acid $\alpha$-glucosidase (Gaa) knockout mice in a dose-dependent fashion. The 20 mg/kg dose of ATB200 consistently removed a greater proportion of stored glycogen in Gaa knockout mice than the 5 and 10 mg/kg dose levels. However, as seen in FIGS. 12A to 12C, ATB200 administered at 5 mg/kg showed a similar reduction of glycogen in mouse heart and skeletal muscles (quadriceps and triceps) to Lumizyme® administered at 20 mg/kg, while ATB200 dosed at 10 and 20 mg/kg showed significantly better reduction of glycogen levels in skeletal muscles than Lumizyme®.

Figure 15:
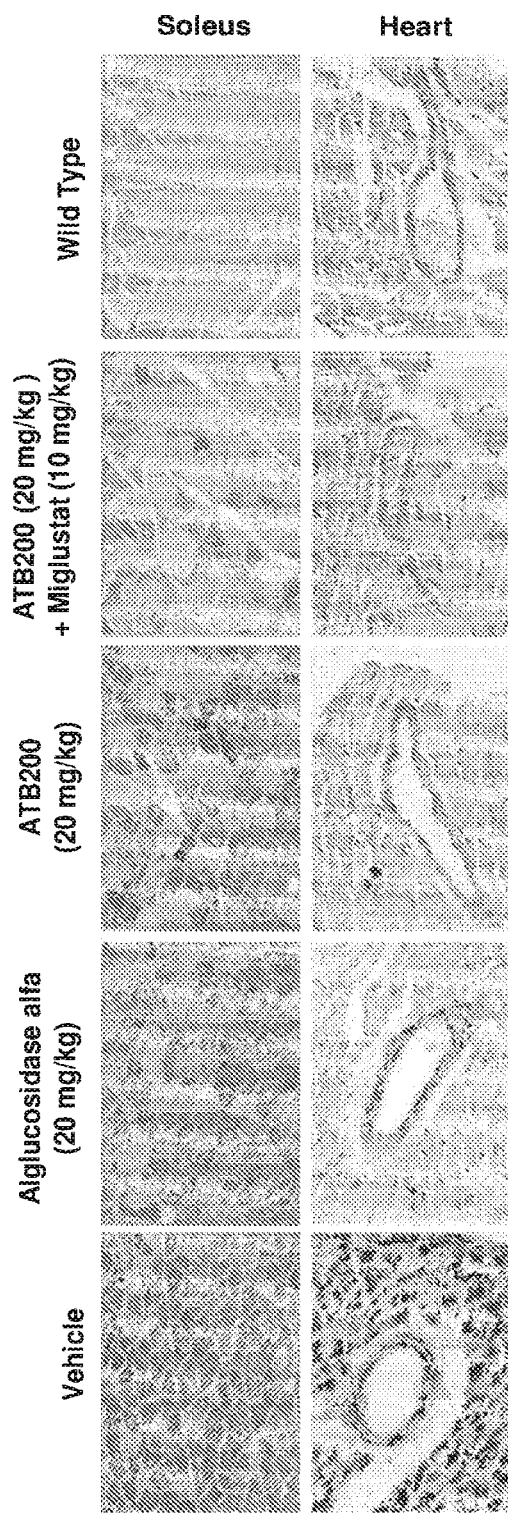
FIG. 15 is a series of electron micrographs of heart and soleus muscle from wild-type and Gaa-knockout mice treated with vehicle, alglucosidase alfa and ATB200 in the presence and absence of miglustat, showing glycogen levels by staining with periodic acid—Schiff reagent (PAS).

FIG. 15 shows the effects of administering alglucosidase alfa (Lumizyme®) and ATB200 on glycogen clearance in Gaa knockout mice. Twelve week old GAA KO mice treated with Lumizyme® or ATB200, 20 mg/kg IV every other week 4 injections. Tissues were collected 14 days after last enzyme dose for glycogen measurement. FIG. 13 shows the relative reduction of glycogen in quadriceps and triceps skeletal muscle, with ATB200 providing a greater reduction of glycogen than Lumizyme®.

Enzyme Example 9: Muscle Physiology and Morphology in Gaa-Knockout Mice

Gaa knockout mice were given two IV bolus administrations of recombinant human acid $\alpha$-glucosidase (alglucosidase alfa or ATB200) at 20 mg/kg every other week. Control mice were treated with vehicle alone. Soleus, quadriceps and diaphragm tissue is harvested two weeks after the last dose of recombinant human acid $\alpha$-glucosidase. Soleus and diaphragm tissue were analyzed for glycogen levels, by staining with periodic acid—Schiff reagent (PAS), and for lysosome proliferation, by measuring levels of the lysosome-associated membrane protein (LAMP1) marker, which is upregulated in Pompe disease. Semi-thin sections of quadriceps muscle embedded in epoxy resin (Epon) were stained with methylene blue and observed by electron microscopy (1000×) to determine the extent of the presence of vacuoles. Quadriceps muscle samples were analyzed immunohistochemically to determine levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

In a similar study, Gaa knockout mice were given four IV bolus administrations of recombinant human acid $\alpha$-glucosidase (alglucosidase alfa or ATB200) at 20 mg/kg every other week. Control mice were treated with vehicle alone. Cardiac muscle tissue was harvested two weeks after the last dose of recombinant human acid $\alpha$-glucosidase and analyzed for glycogen levels, by staining with periodic acid—Schiff reagent (PAS), and for lysosome proliferation, by measuring levels of LAMP1.

Figure 14:
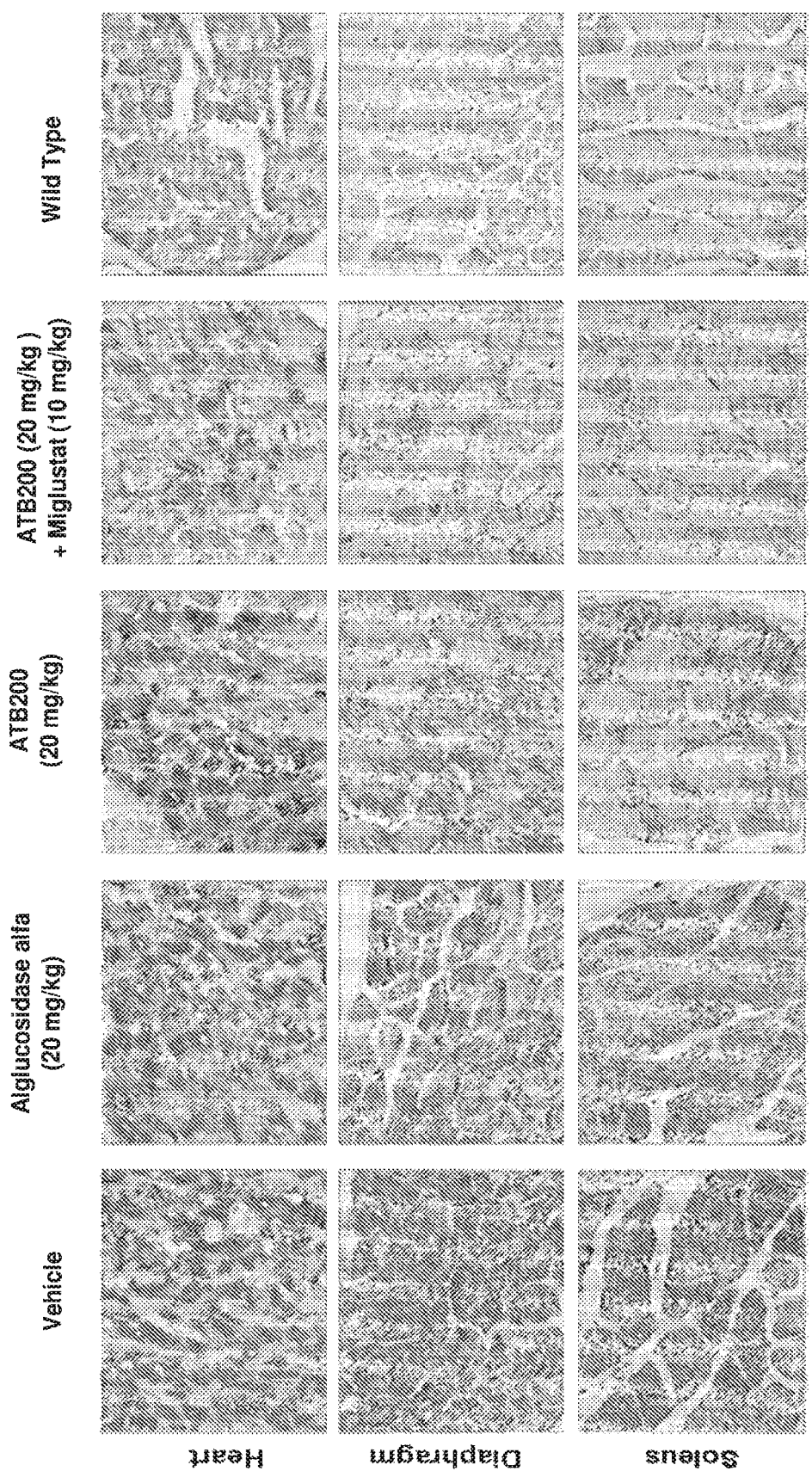
FIG. 14 is a series of electron micrographs of heart, diaphragm and soleus muscle from wild-type and Gaa-knockout mice treated with vehicle, alglucosidase alfa and ATB200 in the presence and absence of miglustat, showing levels of lysosome associated membrane protein (LAMP-1).

As seen in FIG. 14, administration of ATB200 showed a reduction in lysosome proliferation in heart, diaphragm and skeletal muscle (soleus) tissue compared to conventional treatment with alglucosidase alfa. In addition, as seen in FIG. 15, administration of ATB200 showed a reduction in punctate glycogen levels in heart and skeletal muscle (soleus) tissue compared to conventional treatment with alglucosidase alfa.

Figure 16:
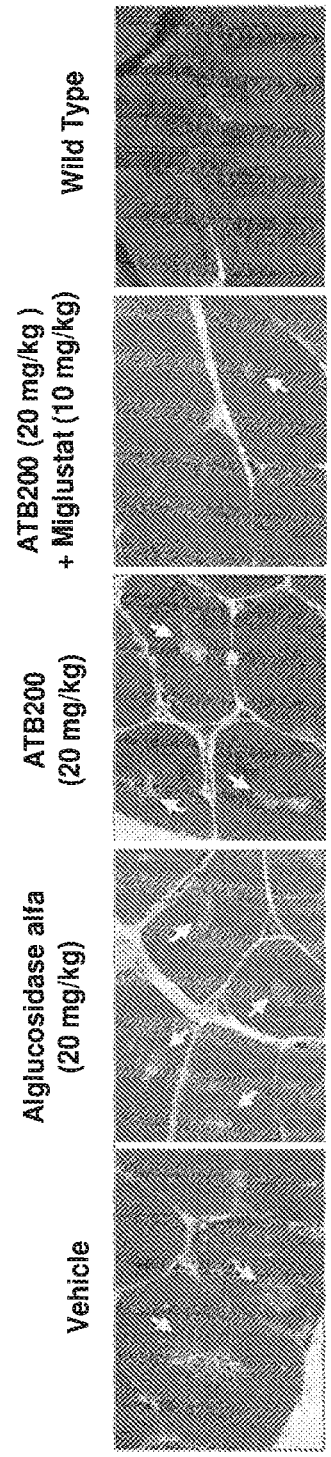
FIG. 16 is a series of electron micrographs (1000×) of quadriceps muscle from wild-type and Gaa-knockout mice treated with vehicle, alglucosidase alfa and ATB200 in the presence and absence of miglustat, stained with methylene blue to show vacuoles (indicated by arrows).
Figure 17:
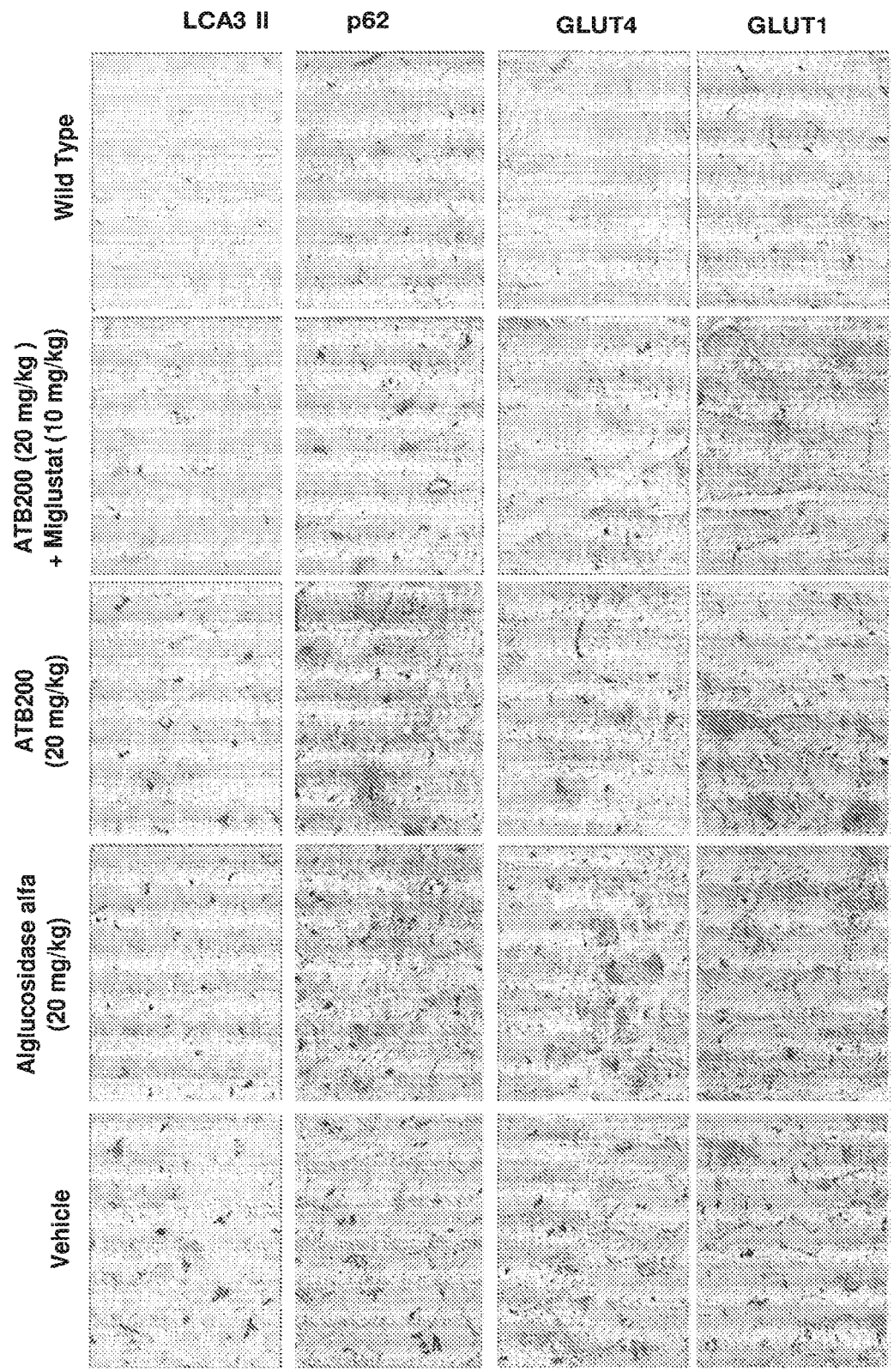
FIG. 17 is a series of electron micrographs (40×) of quadriceps muscle from wild-type and Gaa-knockout mice treated with vehicle, alglucosidase alfa and ATB200 in the presence and absence of miglustat, showing levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

As well, as seen in FIG. 16, ATB200 significantly reduced the number of vacuoles in muscle fiber in the quadriceps of Gaa knockout mice compared to untreated mice and mice treated with alglucosidase alfa. As seen in FIG. 17, levels of both LC3 II and p62 are increased in Gaa knockout mice compared to wild type mice. In addition, levels of the insulin-dependent glucose transporter GLUT4 and the insulin-independent glucose transporter GLUT1 are increased in Gaa knockout mice compared to wild type mice. The elevated GLUT4 and GLUT1 levels associated with acid $\alpha$-glucosidase deficiency can contribute to increased glucose uptake into muscle fibers and increased glycogen synthesis both basally and after food intake.

Enzyme Example 10: Muscle Function in Gaa-Knockout Mice

Figure 18A:
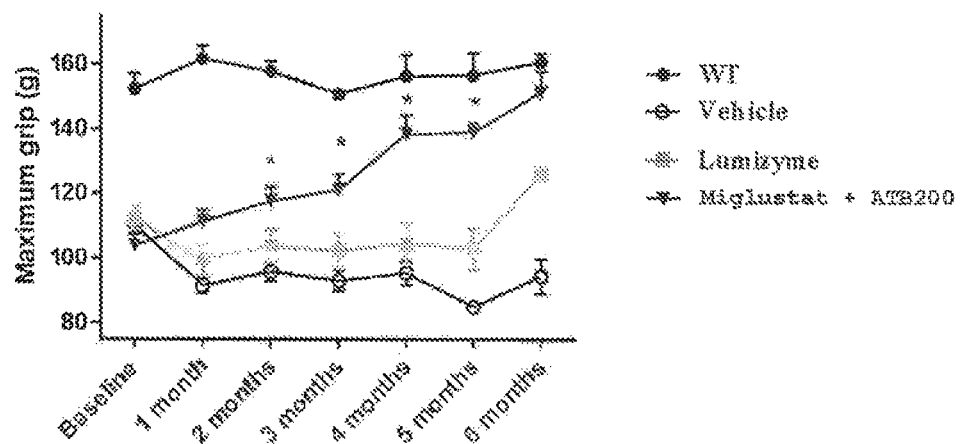
FIGS. 18A and 18B are graphs showing wire hand and grip strength muscle data for wild-type and Gaa-knockout mice treated with vehicle, alglucosidase alfa and ATB200 in the presence of miglustat.
Figure 18B:
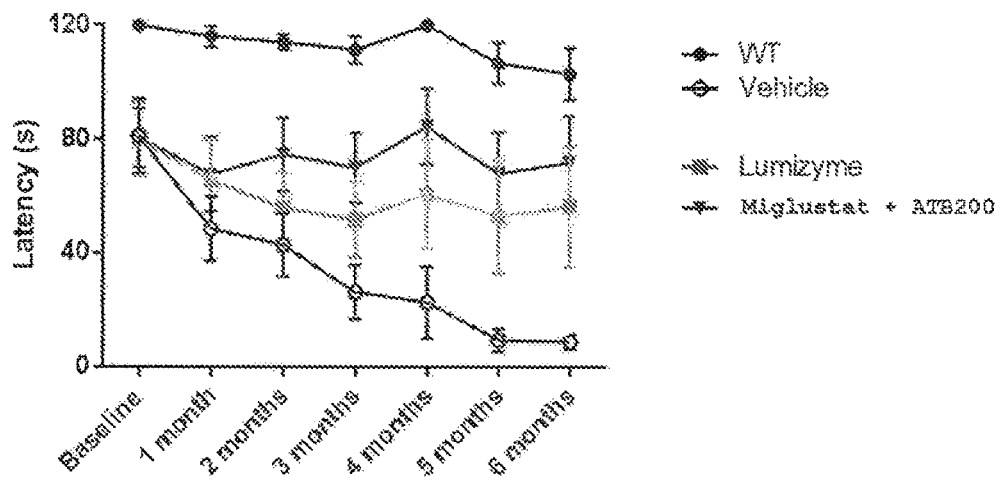
Figure 19A:
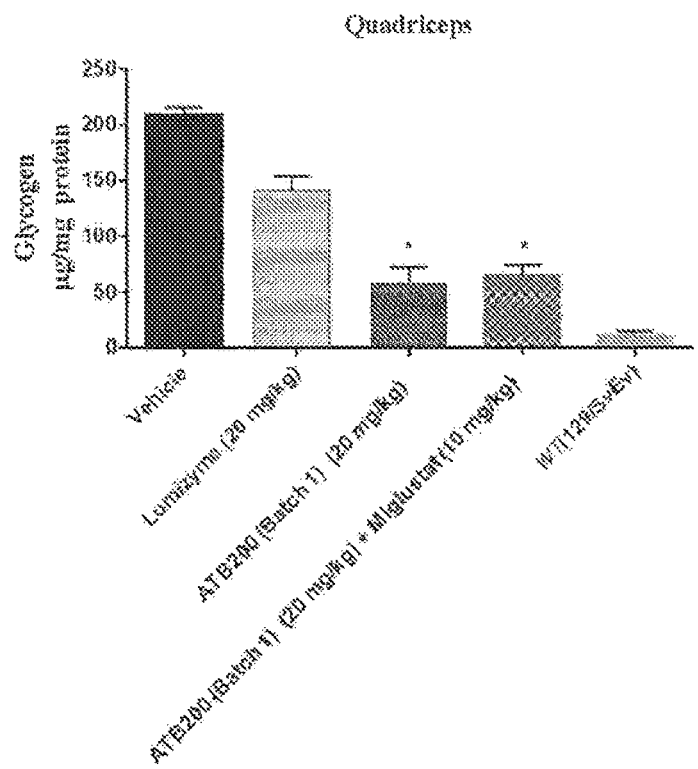
FIGS. 19A-19G are graphs showing glycogen levels in quadriceps, triceps and heart cells from wild-type and Gaa-knockout mice treated with vehicle, alglucosidase alfa and ATB200 in the presence and absence of miglustat.
Figure 19B:
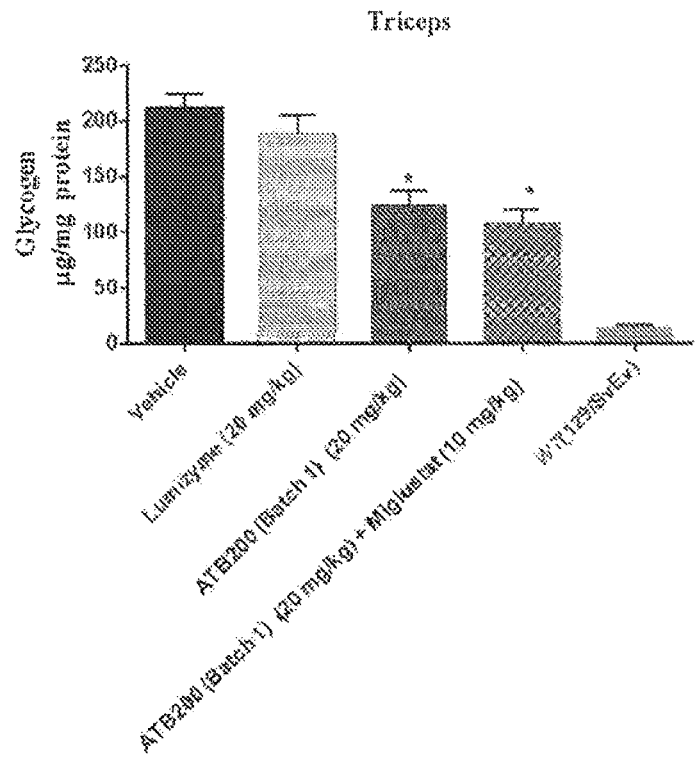
Figure 19C:
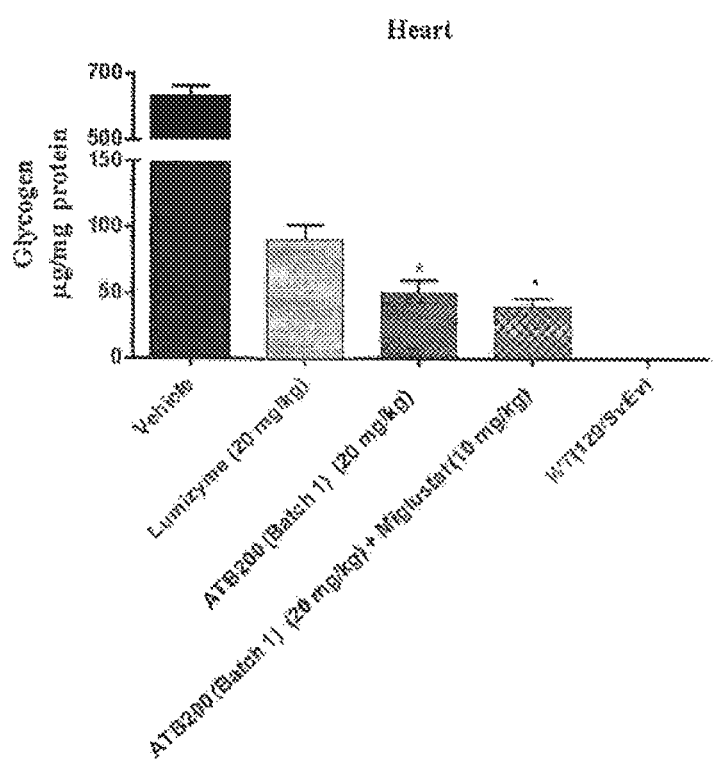
Figure 19D:
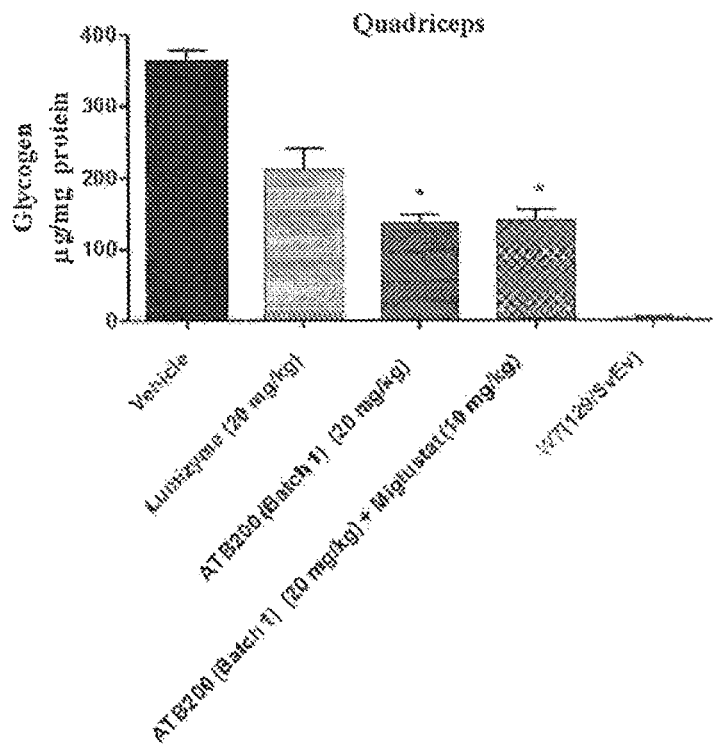
Figure 19E:
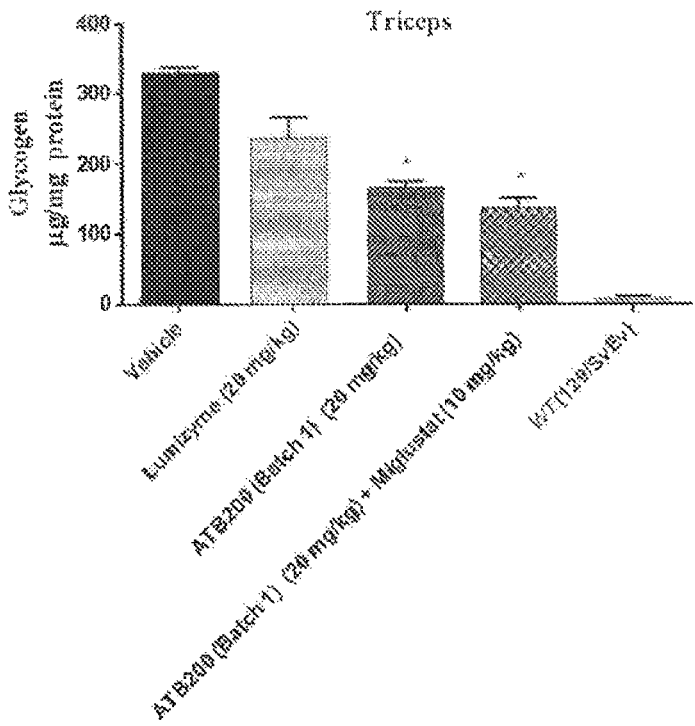
Figure 19F:
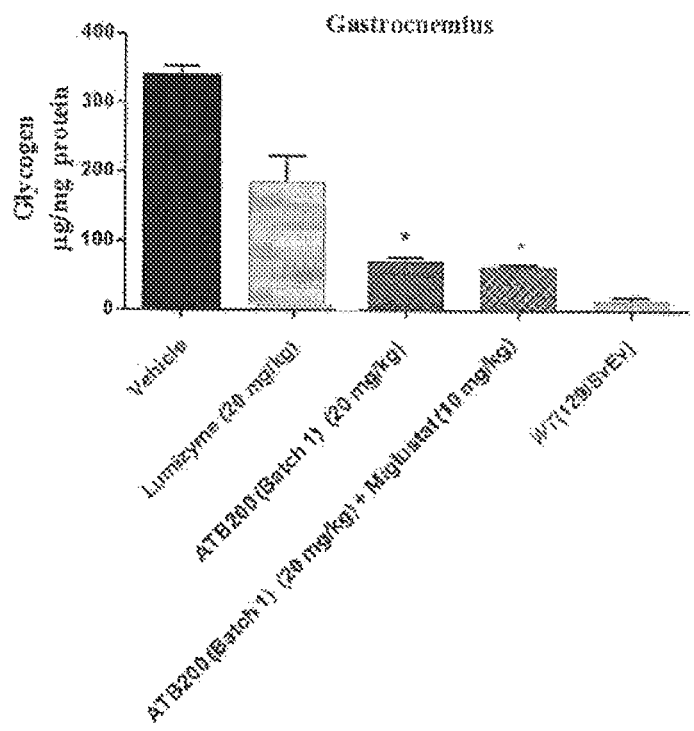
Figure 19G:
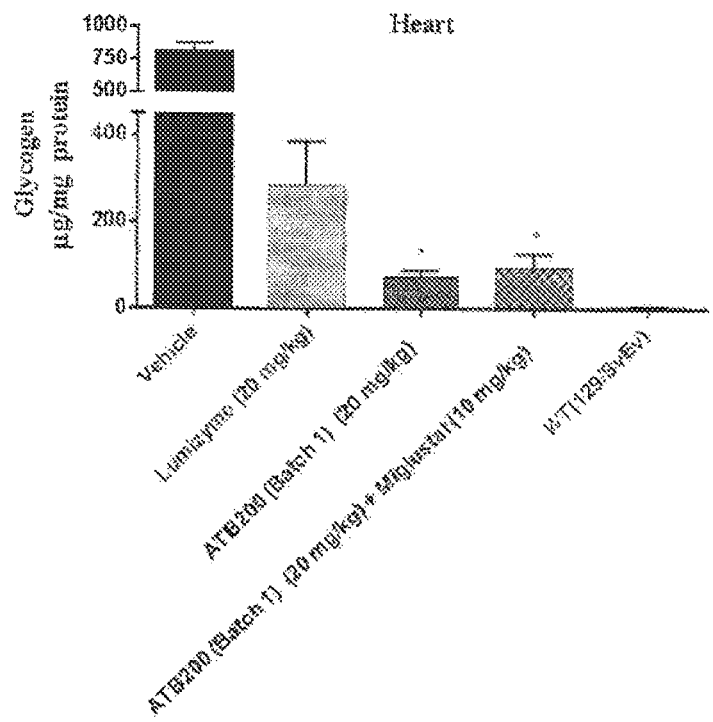

In longer-term studies of 12 biweekly administrations, 20 mg/kg ATB200 plus 10 mg/kg miglustat progressively increased functional muscle strength in Gaa KO mice from baseline as measured by both grip strength and wire hang tests (FIGS. 18A-18B). Alglucosidase alfa (Lumizyme®)-treated mice receiving the same ERT dose (20 mg/kg) were observed to decline under identical conditions throughout most of the study (FIGS. 18A-18B). As with the shorter-term study, ATB200/miglustat had substantially better glycogen clearance after 3 months (FIGS. 19A-19C) and 6 months (FIGS. 19D-19G) of treatment than alglucosidase alfa. ATB200/miglustat also reduced autophagy and intracellular accumulation of LAMP1 and dysferlin after 3 months of treatment (FIG. 20) compared to alglucosidase alfa. In FIG. 18A, * indicates statistically significant compared to Lumizyme® alone ($p<0.05$, 2-sided t-test). In FIGS. 19A-19G, * indicates statistically significant compared to Lumizyme® alone ($p<0.05$, multiple comparison using Dunnett's method under one-way ANOVA analysis).

Taken together, these data indicate that ATB200/miglustat was efficiently targeted to muscles to reverse cellular dysfunction and improve muscle function. Importantly, the apparent improvements in muscle architecture and reduced autophagy and intracellular accumulation of LAMP1 and dysferlin may be good surrogates for improved muscle physiology that correlate with improvements in functional muscle strength. These results suggest that monitoring autophagy and these key muscle proteins may be a rational, practical method to assess the effectiveness therapeutic treatments for Pompe disease in Gaa KO mice that may prove to be useful biomarkers from muscle biopsies in clinical studies.

Figure 20:
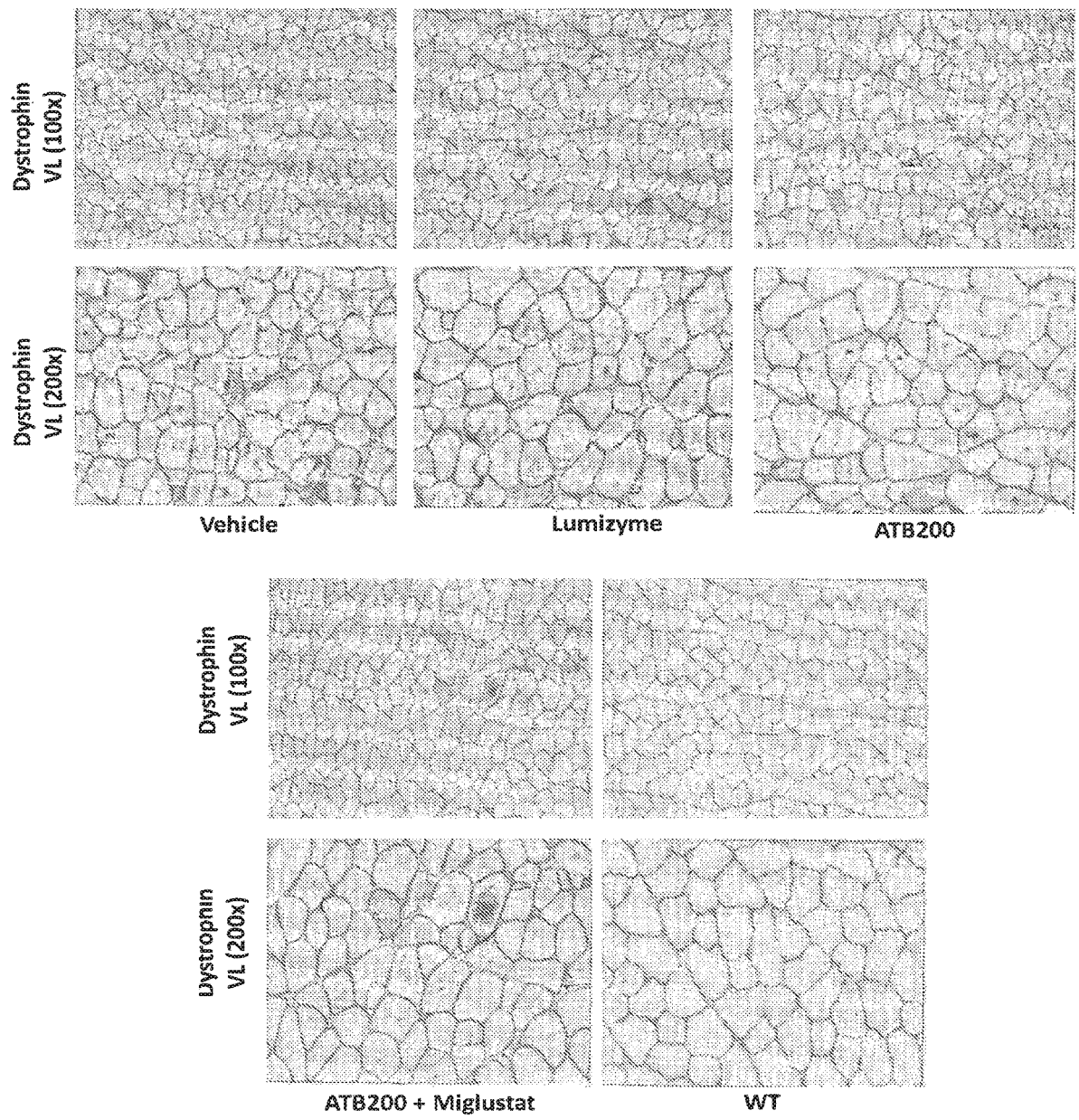
FIG. 20 is a series of photomicrographs (100× and 200×) of muscle fibers of vastus lateralis (VL) from wild-type and Gaa-knockout mice treated with vehicle, alglucosidase alfa and ATB200 in the presence and absence of miglustat, showing dystrophin signals.

FIG. 20 shows that 6 months of ATB200 administration with or without miglustat lowered intracellular accumulation of dystrophin in Gaa KO mice. There was a greater reduction for dystrophin accumulation for ATB200±miglustat than with Lumizyme®.

Formulation Example 1: pH and Buffer

Analytical Methods for Formulation Examples

Analyses of the examples described herein with respect to appearance, pH, protein concentration, etc. were carried out according to the below methods, unless otherwise specified.

Appearance

The appearance of samples, including clarity, color, and visible particles, were examined under black and white background using YB-2 lightbox.

pH

Sample pH was measured with a SevenMulti™ pH Meter.

Protein Concentration

Protein concentration was determined by UV280 readings using a NanoDrop™ 2000 spectrophotometer. All measurements were repeated twice with 2.5 µL sample each time and an average was taken.

Size Exclusion High Performance Liquid Chromatography (SEC-HPLC)

For the pH and buffer, freeze-thaw, and excipient examples, separation of protein monomers and its high molecular weight species and fragments was performed using a TSKgel® G3000 SWXL column (Tosoh Bioscience, 7.8×300 mm, 5 µm, 25° C.) on an Agilent 1260 HPLC system. The mobile phase consisted of 50 mM sodium phosphate, 100 mM sodium chloride and 20 mM sodium citrate (pH 6.0±0.2). The chromatographic system employed a flow rate of 1.0 ml/min, 50-µL, injection volume (typically 1 mg/mL), and 20-min run time with an isocratic gradient. Signals were detected by a UV detector at 280 nm (Reference: 360 nm).

In the PS80 example, separation of protein monomers and its high molecular weight species and fragments was performed using a BioSep™-SEC-s3000 column (Phenomenex, 7.8×300 mm, 5 µm, 25° C.) on an Agilent 1260 HPLC system. The mobile phase consisted of 50 mM sodium phosphate and 100 mM sodium chloride (pH 6.2±0.2). The chromatographic system employed a flow rate of 1.15 ml/min, 50-µL, injection volume (typically 1 mg/mL), and 25-min run time with a isocratic gradient. Signals were detected by a UV detector at 280 nm.

SDS-PAGE (Non-Reduced)

The reportable values are the purity and molecular weight of protein in non-reducing SDS-PAGE. Samples were denatured non-reduced in the presence of excessive SDS to attain a uniform negative charge. In an applied electric field (165V), these SDS-coated species were separated based on their apparent molecular weight through polyacrylamide gel. The separated bands were detected by Coomassie Blue staining.

4-MUG Enzyme Activity

10 µl of sample was diluted and hydrolyzed (by GAA, 37° C. for 60 min) to generate fluorescent product 4-MU. 125 µl of 1 M glycine or 0.1 M NaOH was added in to stop the reaction.

A series of 4-MU standards were analyzed with samples to generate a standard calibration curve based on fluorescence signal. The conversion of RFU to 4-MU amount was achieved by a software mediated comparison to a standard curve, which was regressed according to 4 parameter logistic regression model. Then GAA enzyme activity (nmol 4-MU released/hr/ml GAA) in sample was calculated based on the 4-MU standard curve.

4-MUG Enzymatic Concentration

10 µl of sample and GAA reference standard were diluted and hydrolyzed (by GAA, 37° C. for 60 min) to generate fluorescent product 4-MU. 125 µl of 1 M NaOH was added in to stop the reaction.

A series of GAA reference standards were analyzed with samples to generate a standard calibration curve based on fluorescence signal. The conversion of RFU to 4-MU amount was achieved by a software mediated comparison to a standard curve, which was regressed according to 4 parameter logistic regression model. Then GAA enzyme concentration (nmol 4-MU released/hr/ml GAA) in the sample was calculated based on the GAA standard curve.

Dynamic Light Scattering (DLS)

A micropipette was used to transfer an aliquot of 40 µL of undiluted sample to a 40 µL disposable cuvette. Triplicate measurements were performed for each sample.

Particles: HIAC

200 µl of each sample was diluted into 2000 µl with a filtered reference buffer. The sample was tested three times and 450 µl was used for each test. Average number of particles of each size, 1µm, 3 µm, 5 µm, 10 µm, and 25 µm per ml, were reported.

MicroCal Differential Scanning Calorimetry (DSC)

The capillary cell differential scanning calorimetry (DSC) is utilized to measure the thermal stability of proteins by detecting the difference in the amount of heat required to increase the temperature of a sample and reference as a function of temperature. Specifically, it is used to measure the thermal transition midpoint (Tm), which is an indicator of the relative stability of protein in solution.

Samples were diluted to about 1 mg/mL with reference buffer. An aliquot of 400 μL of reference buffer was added into each odd-numbered well of a 96-well plate while an aliquot of 400 μL of each sample was added into the corresponding even-numbered well. The scanning temperature ranges from 10° C. to 110° C.

Modulated Differential Scanning Calorimetry (mDSC)

The glass transition (Tg') temperature and eutectic temperature (Te) were tested using Netzsch Differential Scan calorimeter (DSC 204 F1). 15 μL of sample was loaded into loading disc for testing. Firstly, the temperature was decreased from 20° C. to −60° C. at the rate of 10° C./min, and the Te value was obtained from the cooling curve during this step. Secondly, the temperature was increased from −60° C. to 40° C. at the rate of 10° C./min, and the Tg' value was analyzed from the heating curve.

M6P

M6P was released from sample by hydrolysis (4 M TFA, 100° C., 4 h) and dried by centrifugal vacuum evaporator. The dried M6P and reference standard were suspended in purified water prior to analysis. A CarboPac PA10 BioLC™ Analytical column (4 mm×250 mm, 3.5 μm, 100 Å, 30° C.) and a CarboPac PA10 BioLCGuard column (4 mm×50 mm, 3.5 μm, 100 Å, 30° C.) were used. The mobile phase consisted of phase A (100 mM NaOH) and phase B (1 M NaOAc, 100 mM NaOH). The chromatographic system employed a flow rate of 1 ml/min, 25-μL, injection volume, and 30-min run time with a gradient. Signals were detected by a pulsed amperometric detection. The M6P content in sample was calculated based on the standard curve.

Sialic Acid

The sialic acids were released from drug molecules by hydrolysis (2 M HAc, 80° C., 2 h), and then labeling all samples and mixed standard solution with DMB (50° C., 17±0.5 h in dark) prior to be separated using a Zorbax Eclipse Plus C18 column (Agilent, 4.6 mm×100 mm, 3.5 μm, 45° C.) on Agilent 1260 HPLC system. The mobile phase consisted of phase A (9% ACN, 7% MeOH) and phase B (100% ACN). The chromatographic system employed a flow rate of 0.5 ml/min, 20 injection volume, and 20 min run time with a gradient. Signals were detected by a fluorescence detector (λex=373 nm, λem=448 nm). Neu5Gc and Neu5Ac content in sample were calculated based on a standard curve.

Ten buffer formulations were prepared having a pH ranging from 4.0 to 8.0, containing 25 mM Sodium Phosphate or 25 mM Sodium Citrate, with or without 50 mM NaCl, as shown in Table 1. The ATB200 4-MUG enzymatic concentration was 1 mg/mL.

TABLE 1

Formulation Compositions:

| Sample | Buffer | NaCl | pH |
|---|---|---|---|
| P40 | 25 mM Sodium Phosphate | 50 mM | 4.0* |
| P50 | | | 5.0 |
| P60 | | | 6.0 |
| P70 | | | 7.0 |
| P80 | | | 8.0 |
| P60 without NaCl | 25 mM Sodium Phosphate | None | 6.0 |

TABLE 1-continued

Formulation Compositions:

| Sample | Buffer | NaCl | pH |
|---|---|---|---|
| C50 | 25 mM Sodium Citrate | 50 mM | 5.0 |
| C55 | | | 5.5 |
| C60 | | | 6.0 |
| C65 | | | 6.5 |

*HCl was used to adjust the pH to 4.0.

Sample Preparation

The material used in the pH and buffer evaluation study is as described in Table 2 below.

TABLE 2

Raw Material Information of pH and Buffer Evaluation Study:

| Conc., mg/ml | | | Enzyme | SDS- | Sialic Acid, | M6P, | |
|---|---|---|---|---|---|---|---|
| UV280 | Enzyme Conc. | SEC, % | activity, U/L | PAGE, % | mol/mol protein | mol/mol protein | CHO, ppm |
| 3.6** | 1.72 | 98.9 | 9094.2 | 99.7 | 5.37 | 3.1 | 422 |

* The buffer of this ATB200 enzyme solution is 50 mM sodium phosphate (pH 6.2), 50 mM NaCl, 2% mannitol
**The extinction coefficient was 1.51 AU*mL*mg$^{-1}$*cm$^{-1}$ 25 mM Sodium Phosphate buffer containing 50 mM NaCl at pH 4.0 (P40), 5.0 (P50), 6.0 (P60), 7.0 (P70), and 8.0 (P80), 25 mM Sodium Phosphate buffer at pH 6.0 (P60 without NaCl), and 25 mM Sodium Citrate buffer containing 50 mM NaCl at pH 5.0 (C50), 5.5 (C55), 6.0 (C60) and 6.5 (C65) were prepared. For pH 4.0, HCl was used to adjust the pH in the Sodium Phosphate buffer (pH 4.0).

The ATB200 enzyme solution was concentrated firstly using ultra-filtration centrifugal devices under the condition of 15° C. and 3500 rpm for 40 min. After that, concentrated enzyme solution was buffer-exchanged into the three different buffers described above by two rounds of ultra-filtration at 15° C. and 3500 rpm for 50 min and 55 min. Buffer-exchanged enzyme solutions were subsequently analyzed for protein concentration and 4-MUG enzyme concentration.

Finally, appropriate volume of each buffer was added to adjust the final ATB200 enzyme concentration to 1.0 mg/mL. The final ATB200 concentration was confirmed by both UV_A280 absorbance and 4-MUG enzyme concentration.

The solutions were aseptically filtered with 0.22-μm polyethersulfone (PES) filter.

Each formulation was aseptically filled into 2-mL glass vials in a bio-safety hood with the filling volume of 500 μL~1000 μL according to the sample amount requirement of analytical tests. Vials were stoppered and then crimp-over-sealed immediately after filling.

Sample Testing

Vials of each formulation were stored at 5° C. and 40° C. for up to 8 weeks, and agitated at 25° C. at 100 rpm on an orbital shaker for up to 5 days (See Table 3). The formulations were sampled initially (T0), 5 days (5D), 2 weeks (2W), 4 weeks (4W) and 8 weeks (8W), as described in Table 3, for the tests of appearance, pH, UV concentration, 4-MUG enzymatic concentration, SEC, HIAC, DLS, 4-MUG enzyme activity, and DSC.

TABLE 3

Study Parameters in ATB200 pH and Buffer Evaluation Study:

| Storage Conditions | T0 | 5 D | 2 W | 4 W | 8 W |
|---|---|---|---|---|---|
| 5° C. | X, Y | — | X | X | X, Z |
| 40° C. |  | — | X | X | X |
| Agitation, ~100 rpm, 25° C. |  | X | — | — | — |

X: Appearance, pH, UV Concentration, 4-MUG Enzymatic Concentration, SEC, HIAC*, DLS, 4-MUG Enzyme activity
Y: DSC
*: HIAC was only tested for T 0 samples and agitation samples Results
Thermal Stability Results—MicroCal DSC
The results of the thermal stability measurements are shown below in Table 4:

TABLE 4

| Sample | Tm onset (° C.) | TM1 (° C.) |
|---|---|---|
| P40 | 56.34 | 66.25 |
| P50 | 63.49 | 73.42 |
| P60 | 60.47 | 72.05 |
| P70 | 47.55 | 64.09 |
| P80 | 37.21 | 47.72 |
| P60 without NaCl | 61.22 | 72.25 |
| C50 | 62.66 | 72.60 |
| C55 | 62.89 | 73.39 |
| C60 | 59.26 | 70.83 |
| C65 | 53.45 | 67.24 |

Higher $Tm_{onset}$ indicates better thermal stability of the protein in the particular formulation. Accordingly, the formulations exhibiting the highest thermal stability were P50, C55, C50, P60 without NaCl, P60 and C60. These results indicate that ATB200 enzyme has better thermal stability in weak acidic buffer than in basic condition.

Appearance—Agitation
The results of the appearance of the agitation study are shown below in Table 5:

TABLE 5

| Sample | T0 | Agitation, 100 rpm, 25° C., 5 days |
|---|---|---|
| P40 | Colorless, clear, free of visible particles | Colorless, clear, tiny visible particles |
| P50 |  | Colorless, clear, very tiny visible particles |
| P60 |  | Colorless, clear, very tiny visible particles |
| P70 |  | Colorless, clear, tiny visible particles |
| P80 |  | Colorless, clear, visible particles |
| P60 without NaCl |  | Colorless, clear, free of visible particles |
| C50 |  | Colorless, clear, free of visible particles |
| C55 |  | Colorless, clear, free of visible particles |
| C60 |  | Colorless, clear, free of visible particles |
| C65 |  | Colorless, clear, free of visible particles |

As can be seen from the table, after 5-day agitation, P60 without NaCl, C50, C55, C60, and C65 maintained colorless, clear, and free of visible particles, but visible particles were observed in P40, P50, P60, P70, and P80. This data shows that sodium citrate buffer stabilized the formulation better than sodium phosphate buffer after agitation.

pH
The results of the pH measurements are shown below in Table 6:

TABLE 6

| | pH | | | | | | | |
|---|---|---|---|---|---|---|---|---|
| | | 5° C. | | | 40° C. | | | Agitation, 100 rpm, 25° C., 5 days |
| Sample | T0 | 2 W | 4 W | 8 W | 2 W | 4 W | 8 W | |
| P40 | 4.293 | 4.233 | 4.273 | 4.380 | 4.618 | 4.537 | 4.606 | 4.296 |
| P50 | 5.051 | 5.008 | 5.011 | 4.936 | 5.070 | 4.998 | 5.044 | 5.002 |
| P60 | 6.053 | 6.025 | 5.927 | 5.927 | 6.030 | 5.911 | 5.949 | 6.017 |
| P70 | 7.093 | 7.043 | 6.999 | 6.941 | 7.037 | 7.024 | 7.014 | 7.027 |
| P80 | 7.864 | 7.823 | 7.749 | 7.767 | 7.834 | 7.834 | 7.767 | 7.883 |
| P60 without NaCl | 6.091 | 6.040 | 5.927 | 5.736 | 6.049 | 5.852 | 5.862 | 6.028 |
| C50 | 5.069 | 5.034 | 4.986 | 4.971 | 5.030 | 4.997 | 5.016 | 5.011 |
| C55 | 5.564 | 5.524 | 5.486 | 5.501 | 5.517 | 5.459 | 5.501 | 5.517 |
| C60 | 6.071 | 6.044 | 6.020 | 5.983 | 6.038 | 6.038 | 5.998 | 6.035 |
| C65 | 6.566 | 6.551 | 6.526 | 6.422 | 6.562 | 6.513 | 6.516 | 6.544 |

As seen from the data, both phosphate and citrate buffers with 50 mM NaCl ranged from pH 5.0 to 6.5 were able to maintain designated pH throughout. During buffer exchange, concentration adjustment, 8-week storage at 5° C. and 40° C., and agitation, there was no significant change in the pH of the samples.

By contrast, pH decreased in P60 without NaCl after 8-week storage at both 5° C. and 40° C., and pH increased in P40 after buffer exchange and 8-week storage at both temperatures. However, agitation did not lead to any change of pH in both P40 and P60 without NaCl.

Protein Concentration
The results of the protein concentration measurements are shown below in Table 7:

TABLE 7

| | UV Concentration, mg/mL | | | | | | | | |
|---|---|---|---|---|---|---|---|---|---|
| | | 5° C | | | 40° C | | | | Agitation, 100 rpm, 25° C., 5 days |
| Sample | T0 | 2 W | 4 W | 8 W | 2 W | 4 W | 8 W | 8 W* | |
| P40 | 1.72 | 1.75 | 1.72 | 1.71 | 1.88 | 1.70 | 1.69 | 1.50 | 1.73 |
| P50 | 1.74 | 1.80 | 1.81 | 1.81 | 1.91 | 1.99 | 1.98 | 1.56 | 1.80 |
| P60 | 1.90 | 1.92 | 1.88 | 1.87 | 1.96 | 2.10 | 2.04 | 1.31 | 1.87 |
| P70 | 1.79 | 1.76 | 1.75 | 1.73 | 1.83 | 1.75 | 1.72 | 1.66 | 1.74 |

TABLE 7-continued

| | | UV Concentration, mg/mL | | | | | | | |
|---|---|---|---|---|---|---|---|---|---|
| | | | 5° C | | | 40° C | | | Agitation, 100 rpm, 25° |
| Sample | T0 | 2 W | 4 W | 8 W | 2 W | 4 W | 8 W | 8 W* | C., 5 days |
| P80 | 2.20 | 2.25 | 2.21 | 2.20 | 2.25 | 2.21 | 2.23 | 2.19 | 2.25 |
| P60 without NaCl | 1.82 | 1.85 | 1.82 | 1.81 | 1.87 | 1.90 | 1.92 | 1.58 | 1.86 |
| C50 | 1.83 | 1.80 | 1.81 | 1.81 | 1.80 | 1.76 | 1.72 | 1.71 | 1.80 |
| C55 | 1.84 | 1.83 | 1.83 | 1.84 | 1.89 | 1.85 | 1.79 | 1.54 | 1.82 |
| C60 | 2.00 | 1.98 | 1.97 | 1.97 | 2.08 | 2.21 | 2.14 | 1.19 | 1.96 |
| C65 | 2.03 | 2.05 | 1.98 | 2.00 | 2.17 | 2.19 | 2.39 | 1.26 | 2.06 |

8-week storage at 5° C. and agitation for 5 days did not affect the protein concentration. No significant variation was observed among all formulations.

By contrast, during storage at 40° C., protein concentration slightly increased in P50, P60, P60 without NaCl, C60, and C65, slightly decreased in C50, and maintained in P40, P70, P80, C55. Because of the formation of visible particles in 40° C. samples, 40° C./8-week samples were re-tested after centrifugation at 12000 rpm for 1 minute. The results showed a drop in protein concentration after centrifugation in the samples containing particles, which indicated that the particles present in the samples had an impact on the adsorption at 280 nm.

4-MUG Enzymatic Concentration

The results of the 4-MUG enzymatic concentration measurements are shown below in Table 8:

TABLE 8

| | | 4-MUG Enzymatic Concentration, mg/mL | | | | | | |
|---|---|---|---|---|---|---|---|---|
| Sample | | 5° C. | | | 40° C. | | | Agitation, 100 rpm, 25° |
| Name | T0 | 2 W | 4 W | 8 W | 2 W | 4 W | 8 W | C., 5 days |
| P40 | 0.86 | 0.91 | 0.91 | 0.76 | 0.34 | 0.16 | 0.04 | 1.02 |
| P50 | 0.92 | 1.08 | 1.08 | 1.05 | 0.78 | 0.62 | 0.33 | 1.12 |
| P60 | 0.89 | 1.10 | 1.13 | 1.13 | 0.92 | 0.87 | 0.58 | 1.14 |
| P70 | 0.82 | 0.93 | 0.92 | 0.86 | 0.00 | 0.00 | 0.00 | 1.00 |
| P80 | 0.27 | 0.00 | 0.00 | 0.00 | 0.00 | BQL | NA | 0.00 |
| P60 without NaCl | 0.87 | 1.10 | 1.06 | 1.05 | 1.01 | 0.98 | 0.73 | 1.09 |
| C50 | 0.87 | 1.04 | 1.06 | 1.05 | 0.89 | 0.68 | 0.33 | 1.14 |
| C55 | 0.90 | 1.15 | 1.11 | 1.09 | 1.03 | 0.96 | 0.63 | 1.13 |
| C60 | 1.02 | 1.22 | 1.33 | 1.23 | 1.08 | 0.92 | 0.53 | 1.26 |
| C65 | 1.02 | 1.23 | 1.29 | 1.28 | 0.15 | 0.01 | 0.00 | 1.29 |

After buffer exchange, the 4-MUG enzymatic concentration of P80 dropped to 0.27 mg/mL immediately. This indicated that pH 8.0 affected the enzyme activity significantly. After 2-week storage at both 5° C. and 40° C., the enzymatic concentration dropped to zero. Except for P80, after 8-week storage at 5° C., the enzymatic concentrations of most formulations were stable and dropped a little in P40.

By contrast, 40° C. storage affected the enzymatic concentration obviously. After 2 weeks, the enzymatic concentration was gone in P70, dramatically dropped in P40 and C65, and decreased obviously in P50. After 4 weeks, the enzymatic concentration continued to decrease. Finally, after 8 weeks, the enzymatic concentrations were close to zero in P40 and C65, dropped to 0.33 mg/mL in pH 5.0 buffers (P50 and C50) and to 0.5~0.7 mg/mL in pH 5.5~6.0 buffers (P60, P60 without NaCl, C55, and C60). Among them, P60 without NaCl had a highest enzymatic concentration (0.73 mg/mL) finally. The results indicate that the enzyme concentration was most preserved with respect to 4-MUG enzymatic concentration in the range of pH 5.5~6.0, but there was no significant difference between sodium phosphate buffer and sodium citrate buffer.

During the agitation study, except P80, the enzymatic concentration did not significantly change.

4-MUG Enzyme Activity

The results of the 4-MUG enzyme activity measurements are shown below in Table 9:

TABLE 9

| | | 4-MUG Enzyme Activity, U/L | | | | | | |
|---|---|---|---|---|---|---|---|---|
| Sample | | 5° C. | | | 40° C. | | | Agitation, 100 rpm, 25° |
| Name | T0 | 2 W | 4 W | 8 W | 2 W | 4 W | 8 W | C., 5 days |
| P40 | 4703.4 | 5092.7 | 4153.7 | 3697.2 | 1822.3 | 712.2 | 211.5 | 5439.9 |
| P50 | 5043.8 | 6021.5 | 4947.8 | 5101.4 | 4344.4 | 2836.9 | 1561.7 | 5953.8 |
| P60 | 4915.3 | 6133.7 | 5193.7 | 5487.5 | 5170.4 | 4002.9 | 2790.4 | 6087.0 |
| P70 | 4481.1 | 5233.1 | 4211.5 | 4195.4 | 0.2 | 0.4 | 0.0 | 5360.5 |

TABLE 9-continued

4-MUG Enzyme Activity, U/L

| Sample Name | T0 | 5° C. 2 W | 4 W | 8 W | 40° C. 2 W | 4 W | 8 W | Agitation, 100 rpm, 25° C., 5 days |
|---|---|---|---|---|---|---|---|---|
| P80 | 1402.6 | 1.8 | 1.6 | 0.7 | 0.2 | BQL | 0.0 | 0.6 |
| P60 without NaCl | 4763.7 | 6130.1 | 4862.1 | 5120.0 | 5662.4 | 4476.0 | 3549.7 | 5799.6 |
| C50 | 4772.4 | 5811.8 | 4850.7 | 5110.8 | 4964.9 | 3121.6 | 1544.8 | 6057.4 |
| C55 | 4957.3 | 6450.1 | 5091.7 | 5321.7 | 5740.9 | 4411.9 | 3054.1 | 6036.5 |
| C60 | 5641.1 | 6829.9 | 6061.0 | 5999.2 | 6026.4 | 4243.2 | 2563.3 | 6662.8 |
| C65 | 5639.3 | 6848.2 | 5892.8 | 6238.7 | 761.6 | 65.5 | 3.4 | 6827.8 |

The 4-MUG enzyme activity change trend paralleled that of 4-MUG enzymatic concentration.

P80 showed worst stability in 4-MUG enzyme activity under the testing conditions. The enzyme activity of P80 had around 70% decrease after buffer exchange. Later on, the enzyme activity was almost totally lost after 2-week storage at 5° C. and 40° C. The basic condition significantly affected the enzyme activity.

After 8-week storage at 5° C., the enzyme activity of PS80 almost completely lost; 20% of decrease was found in P40; no significant change was observed in other formulations.

By contrast, 40° C. storage led to obvious decrease in the enzyme activity in all formulations. After 2 weeks, the enzyme activity almost completely lost in P70, dramatically decreased in P40 and C65, and obviously dropped in P50. The enzyme activity continued to decrease in different degree from 2 weeks to 4 weeks. At the end of the study, the enzyme activity almost completely lost in C65, dropped to 211.5 U/L in P40 to ~1550 U/L in P50 and C50, and to 2500~3000 U/L in C60, P60, and C55. Among the formulations, P60 without NaCl kept the highest activity of 3549.7 U/L.

Based on the testing results of 4-MUG enzyme activity, the enzyme was most stabilized at a pH in the range of pH 5.5~6.0, but no distinction was seen between sodium phosphate buffer and sodium citrate buffer.

Purity: SEC-HPLC

The results of the SEC measurements are shown below in Table 10:

TABLE 10

| Sample Name | SEC | T0 | 5° C. 2 W | 4 W | 8 W | 40° C. 2 W | 4 W | 8 W | Agitation, 100 rpm, 25° C., 5 days |
|---|---|---|---|---|---|---|---|---|---|
| P40 | Monomer % | 94.0 | 89.1 | 81.9 | 74.3 | 41.2 | 18.7 | 7.1 | 90.8 |
|  | HMW % | 1.3 | 1.6 | 2.4 | 2.4 | ND | ND | ND | 0.7 |
|  | LMW % | 4.7 | 9.4 | 15.7 | 23.4 | 58.8 | 81.3 | 93.0 | 8.5 |
| P50 | Monomer % | 99.3 | 98.1 | 95.4 | 92.8 | 81.1 | 66.1 | 42.0 | 96.6 |
|  | HMW % | 0.4 | 0.4 | 0.7 | 1.4 | 0.2 | ND | 0.1 | 0.6 |
|  | LMW % | 0.4 | 1.6 | 4.0 | 5.9 | 18.6 | 33.9 | 57.9 | 2.8 |
| P60 | Monomer % | 98.7 | 97.7 | 96.8 | 96.2 | 96.1 | 92.4 | 80.8 | 96.8 |
|  | HMW % | 0.8 | 0.9 | 1.2 | 1.9 | 2.1 | 0.6 | 2.7 | 1.1 |
|  | LMW % | 0.5 | 1.4 | 2.0 | 2.0 | 1.8 | 7.0 | 16.5 | 2.1 |
| P70 | Monomer % | 97.7 | 94.6 | 92.4 | 87.0 | 0.5 | ND | 0.1 | 93.5 |
|  | HMW % | 1.8 | 3.3 | 5.4 | 11.0 | 96.9 | 96.4 | 96.7 | 4.1 |
|  | LMW % | 0.5 | 2.1 | 2.3 | 1.9 | 2.7 | 3.6 | 3.2 | 2.4 |
| P80 | Monomer % | 44.9 | 35.3 | 34.4 | 26.7 | ND | ND | 0.2 | 15.2 |
|  | HMW % | 54.5 | 63.0 | 61.4 | 69.3 | 97.3 | 97.2 | 96.5 | 83.7 |
|  | LMW % | 0.6 | 1.7 | 4.2 | 4.0 | 2.7 | 2.8 | 3.3 | 1.1 |
| P60 without NaCl | Monomer % | 96.6 | 98.0 | 97.0 | 96.8 | 94.95 | 92.4 | 83.6 | 95.6 |
|  | HMW % | 0.5 | 0.5 | 1.0 | 1.2 | 1.44 | 0.7 | 3.0 | 1.0 |
|  | LMW % | 2.9 | 1.5 | 2.0 | 2.0 | 3.62 | 7.0 | 13.5 | 3.4 |
| C50 | Monomer % | 98.3 | 99.5 | 95.6 | 93.0 | 96.3 | 62.3 | 32.3 | 92.1 |
|  | HMW % | 0.2 | 0.2 | 0.4 | 0.2 | 2.0 | 0.1 | ND | 0.4 |
|  | LMW % | 1.5 | 0.4 | 4.0 | 6.8 | 1.7 | 37.6 | 67.7 | 7.6 |
| C55 | Monomer % | 98.5 | 99.4 | 99.3 | 95.9 | 94.81 | 88.52 | 68.5 | 92.6 |
|  | HMW % | 0.3 | 0.2 | 0.2 | 1.4 | 0.29 | 0.19 | 0.2 | 0.3 |
|  | LMW % | 1.3 | 0.4 | 0.5 | 2.7 | 4.9 | 11.3 | 31.3 | 7.1 |
| C60 | Monomer % | 98.7 | 99.2 | 97.8 | 97.6 | 98.0 | 95.8 | 77.5 | 92.8 |
|  | HMW % | 0.3 | 0.3 | 0.8 | 1.1 | 1.1 | 1.0 | 5.5 | 0.8 |
|  | LMW % | 1.0 | 0.6 | 1.4 | 1.3 | 0.9 | 3.2 | 17.0 | 6.4 |
| C65 | Monomer % | 98.8 | 98.9 | 97.6 | 97.9 | 22.4 | 10.0 | ND | 91.4 |
|  | HMW % | 0.4 | 0.5 | 1.2 | 1.9 | 76.7 | 86.1 | 86.8 | 4.4 |
|  | LMW % | 0.8 | 0.6 | 1.2 | 0.3 | 1.0 | 3.9 | 13.2 | 4.2 |

After buffer exchange, the SEC purity of some of the formulations decreased significantly comparing to the starting material (SEC monomer: 98.9%). In P80, the SEC purity dropped to 44.9%, and 54.5% of aggregates formed; in P40, there was a 4.9% decrease on monomer percentage compared to the before-exchange DS, with more LMW fragments formed than HMW molecule (4.7% VS 1.3%); in P70, a slight decrease (1.2%) in monomer percentage was found, corresponding to an increase in aggregates; in P60 without NaCl, there was a 2.3% decrease in monomer percentage.

After 8-week 5° C. storage, the SEC purity of formulations P60, P60 without NaCl, and C65 maintained well but the SEC purity of the other formulations significantly decreased compared to T0. In P40, the SEC purity dropped dramatically to 74.3% (T0: 94.0%), and 23.4% of LMW fragments formed; in P50 and C50, there were a slight decrease (5~7%) in the monomer and an increase (5~7%) in LMW fragments. In P80, an 18.2% decrease was found which was mainly transferred to aggregation (14.8%). So as in P70, there was a 10.7% decrease in monomer and 9.2% increase in HMW fragments. In C55, there was a slight change in monomer, HMW and LMW percentage.

40° C. storage led to dramatic monomer percentage change in all formulations. In P70 and P80, the SEC monomer dropped to 0~0.5% after 2 weeks and in C65 there was 22.4% left, and they mostly turned to aggregates after 8 weeks. In P40, P50 and C50, there was a significant drop (5090%) in monomer, attributed mostly to formation of LMW fragments. In P60, P60 without NaCl, and C60, after 8 weeks the SEC monomer percentage decreased to 80.8%, 83.6% and 77.5%, respectively.

The SEC results indicated that pH 6.0 performed best for ATB200 stability, and no significant difference was found between sodium phosphate buffer and sodium citrate buffer. Furthermore, absence of sodium chloride in the formulations did not impact ATB200 stability.

During agitation study, SEC purity decreased slightly in P60 and P60 without NaCl. In P40, P50, P70, P80, C50, C60 and C65, there was an obvious decrease in the monomer percent.

Polydispersity: DLS

The results of the DLS measurements are shown below in Table 11:

TABLE 11

| Study Condition | Sample | Z-Ave d · nm | PdI | Pk 1 Mean Int d · nm | Pk2 Mean Int d · nm | Pk 3 Mean Int d · nm | Pk 1 Area Int Percent | Pk 2 Area Int Percent | Peak 3 Area Int Percent |
|---|---|---|---|---|---|---|---|---|---|
| T0 | P40 | 10.9 | 0.183 | 11.8 | 4080 | 0 | 96.9 | 3.1 | 0 |
|  | P50 | 10.7 | 0.181 | 11.4 | 4248 | 0 | 96.9 | 3.1 | 0 |
|  | P60 | 10.2 | 0.186 | 10.9 | 4199 | 0 | 96.6 | 3.4 | 0 |
|  | P70 | 9.6 | 0.144 | 11.2 | 0 | 0 | 100 | 0 | 0 |
|  | P80 | 12.6 | 0.150 | 14.1 | 4421 | 0 | 98.8 | 1.2 | 0 |
|  | P60 without NaCl | 10.5 | 0.223 | 10.7 | 3952 | 0 | 93.8 | 6.2 | 0 |
|  | C50 | 10.3 | 0.133 | 11.4 | 0 | 0 | 100 | 0 | 0 |
|  | C55 | 9.9 | 0.129 | 11.1 | 0 | 0 | 100 | 0 | 0 |
|  | C60 | 9.7 | 0.114 | 11.0 | 0 | 0 | 100 | 0 | 0 |
|  | C65 | 9.7 | 0.103 | 10.7 | 0 | 0 | 100 | 0 | 0 |
| 5° C., 2 W | P40 | 12.8 | 0.260 | 13.3 | 437 | 0 | 89.6 | 10.4 | 0 |
|  | P50 | 11.8 | 0.266 | 11.7 | 500.7 | 0 | 88.3 | 11.7 | 0 |
|  | P60 | 9.9 | 0.161 | 10.7 | 4352 | 0 | 97.8 | 2.2 | 0 |
|  | P70 | 10.0 | 0.137 | 10.9 | 4560 | 0 | 98.9 | 1.1 | 0 |
|  | P80 | 13.2 | 0.100 | 14.7 | 0 | 0 | 100 | 0 | 0 |
|  | P60 without NaCl | 7562.0 | 1.000 | 4099.0 | 0 | 0 | 100 | 0 | 0 |
|  | C50 | 11.0 | 0.219 | 11.7 | 3459 | 0 | 94.1 | 5.9 | 0 |
|  | C55 | 10.1 | 0.152 | 11.2 | 4409 | 0 | 98.7 | 1.3 | 0 |
|  | C60 | 3506.0 | 0.271 | 3745.0 | 9.144 | 0 | 93.6 | 6.4 | 0 |
|  | C65 | 355.5 | 1.000 | 4194.0 | 11.08 | 0 | 74.6 | 25.4 | 0 |
| 5° C., 4 W | P40 | 12.2 | 0.220 | 13.4 | 2891 | 0 | 94.3 | 5.7 | 0 |
|  | P50 | 11.8 | 0.255 | 12.0 | 1059 | 0 | 89.8 | 10.2 | 0 |
|  | P60 | 9.9 | 0.126 | 11.1 | 0 | 0 | 100 | 0 | 0 |
|  | P70 | 9.9 | 0.087 | 10.8 | 0 | 0 | 100 | 0 | 0 |
|  | P80 | 13.5 | 0.176 | 14.7 | 4442 | 0 | 97.5 | 2.5 | 0 |
|  | P60 without NaCl | 9.6 | 0.102 | 10.6 | 0 | 0 | 100 | 0 | 0 |
|  | C50 | 11.3 | 0.229 | 11.9 | 2913 | 0 | 92.9 | 7.1 | 0 |
|  | C55 | 10.5 | 0.205 | 11.2 | 4067 | 0 | 95.6 | 4.4 | 0 |
|  | C60 | 9.9 | 0.116 | 11.1 | 0 | 0 | 100 | 0 | 0 |
|  | C65 | 10.7 | 0.208 | 12.5 | 4042 | 0 | 97.4 | 2.6 | 0 |
| 5° C., 8 W | P40 | 15.1 | 0.329 | 13.7 | 116.8 | 0 | 77.6 | 22.4 | 0 |
|  | P50 | 14.1 | 0.335 | 14.0 | 113.7 | 0 | 79.2 | 20.8 | 0 |
|  | P60 | 10.1 | 0.148 | 11.0 | 4395 | 0 | 98.3 | 1.7 | 0 |
|  | P70 | 10.5 | 0.152 | 11.6 | 4397 | 0 | 98.4 | 1.6 | 0 |
|  | P80 | 13.6 | 0.121 | 15.4 | 0 | 0 | 100 | 0 | 0 |
|  | P60 without NaCl | 10.3 | 0.187 | 11.0 | 4055 | 0 | 96.3 | 3.7 | 0 |
|  | C50 | 11.8 | 0.281 | 12.3 | 486.6 | 0 | 88.4 | 11.6 | 0 |
|  | C55 | 11.8 | 0.265 | 12.3 | 583.3 | 0 | 89.6 | 10.4 | 0 |
|  | C60 | 11.8 | 0.261 | 12.2 | 3465 | 0 | 91.7 | 8.3 | 0 |
|  | C65 | 9.7 | 0.105 | 10.8 | 0 | 0 | 100 | 0 | 0 |

TABLE 11-continued

| Study Condition | Sample | Z-Ave d·nm | PdI | Pk 1 Mean Int d·nm | Pk2 Mean Int d·nm | Pk 3 Mean Int d·nm | Pk 1 Area Int Percent | Pk 2 Area Int Percent | Peak 3 Area Int Percent |
|---|---|---|---|---|---|---|---|---|---|
| 40° C., 2 W | P40 | 1768 | 0.316 | 2017 | 5272 | 0 | 96.7 | 3.3 | 0 |
| | P50 | 8330 | 0.418 | 7.2 | 0 | 0 | 100 | 0 | 0 |
| | P60 | 1318 | 0.952 | 741.5 | 5393 | 132.8 | 63.3 | 18.6 | 18.2 |
| | P70 | 66.72 | 0.627 | 39.52 | 4508 | 0 | 69.4 | 30.6 | 0 |
| | P80 | 2963 | 0.733 | 4504 | 33.27 | 0 | 87.8 | 12.2 | 0 |
| | P60 without NaCl | 106.2 | 0.744 | 143 | 2912 | 9.298 | 71.5 | 21 | 7.5 |
| | C50 | 5874 | 1 | 4325 | 5.199 | 0 | 94.9 | 5.1 | 0 |
| | C55 | 30.84 | 0.721 | 704.9 | 9.816 | 0 | 59.1 | 40.9 | 0 |
| | C60 | 2574 | 1 | 168.9 | 5444 | 0 | 57.1 | 42.9 | 0 |
| | C65 | 96.59 | 0.31 | 124.4 | 4622 | 0 | 96.6 | 3.4 | 0 |
| 40° C., 4 W | P40 | 2116 | 0.249 | 2178 | 5236 | 0 | 94.9 | 5.1 | 0 |
| | P50 | 1894 | 0.251 | 2385 | 0 | 0 | 100 | 0 | 0 |
| | P60 | 644.6 | 0.708 | 2879 | 475.1 | 79.89 | 58.8 | 34.1 | 7.1 |
| | P70 | 34.21 | 0.122 | 39.44 | 0 | 0 | 100 | 0 | 0 |
| | P80 | 22.64 | 0.096 | 25.18 | 0 | 0 | 100 | 0 | 0 |
| | P60 without NaCl | 239.5 | 0.53 | 394.6 | 4499 | 0 | 95 | 5 | 0 |
| | C50 | 173.1 | 0.758 | 9.513 | 1373 | 5098 | 45.1 | 44.9 | 10 |
| | C55 | 561.3 | 1 | 1932 | 187.7 | 9.455 | 69.1 | 14 | 9.3 |
| | C60 | 419.3 | 0.706 | 1941 | 244.8 | 68.83 | 61.6 | 34.1 | 4.3 |
| | C65 | 138.3 | 0.248 | 192.7 | 25.24 | 0 | 98.6 | 1.4 | 0 |
| 40° C., 8 W | P40 | 1177 | 0.419 | 1512 | 9.926 | 4.277 | 93.4 | 5 | 1.6 |
| | P50 | 1381 | 0.672 | 1723 | 9.313 | 0 | 92.7 | 7.3 | 0 |
| | P60 | 283 | 0.587 | 1028 | 191.9 | 37.93 | 62.2 | 34.9 | 2.9 |
| | P70 | 36.85 | 0.135 | 43.2 | 0 | 0 | 100 | 0 | 0 |
| | P80 | 23.2 | 0.114 | 26.46 | 0 | 0 | 100 | 0 | 0 |
| | P60 without NaCl | 3215 | 0.445 | 1103 | 0 | 0 | 100 | 0 | 0 |
| | C50 | 2118 | 0.184 | 2711 | 5.565 | 0 | 92.1 | 7.9 | 0 |
| | C55 | 145.3 | 1 | 801.3 | 153.6 | 10.1 | 59.8 | 23 | 14 |
| | C60 | 462.7 | 0.918 | 912.6 | 175.8 | 4998 | 54 | 30.9 | 15.1 |
| | C65 | 196.2 | 0.309 | 279.6 | 45.86 | 5177 | 92.1 | 6.9 | 1 |
| Agitation, 100 rpm, 25° C., 5 D | P40 | 13.0 | 0.331 | 11.8 | 190.8 | 0 | 80.1 | 19.9 | 0 |
| | P50 | 11.8 | 0.290 | 11.3 | 267.5 | 0 | 85.2 | 14.8 | 0 |
| | P60 | 10.1 | 0.165 | 11.0 | 4383 | 0 | 97.9 | 2.1 | 0 |
| | P70 | 10.1 | 0.136 | 11.4 | 0 | 0 | 100 | 0 | 0 |
| | P80 | 51.6 | 0.657 | 21.1 | 3805 | 0 | 55.6 | 44.4 | 0 |
| | P60 without NaCl | 9.7 | 0.118 | 10.8 | 0 | 0 | 100 | 0 | 0 |
| | C50 | 12.7 | 0.319 | 11.8 | 355.7 | 0 | 82.6 | 17.4 | 0 |
| | C55 | 9.8 | 0.140 | 10.9 | 4434 | 0 | 99 | 1 | 0 |
| | C60 | 10.1 | 0.174 | 11.0 | 4397 | 0 | 97.8 | 2.2 | 0 |
| | C65 | 9.6 | 0.084 | 10.5 | 0 | 0 | 100 | 0 | 0 |

DLS data reflected the hydrodynamic radius of protein molecules and polydispersity of particles. Opalescence was observed in some samples, so DLS was used to analyze the sub-visible particles. The DLS result was generally consistent with the indication from appearance.

During 8-week 5° C. storage, both the hydrodynamic radius of protein molecules and polydispersity index (PDI) were stable and comparable in P60, P70, P80, P60 without NaCl and C60. The hydrodynamic radius turned from around 10 nm to a few hundred nm in all other five formulations, especially in P40 after 8 weeks.

During 8-week 40° C. storage, there was a dramatic change in the hydrodynamic radius and PDI in all formulations. However, due to the complex profiles of the aggregates, it is difficult to compare those formulations based on the result.

In the agitation study, the hydrodynamic radius and PDI of P80 had dramatic increase; in P40, P50 and C50, the hydrodynamic radius and PDI had slight increase; in P60, P70, P60 without NaCl, C55, C60, and C65, no significant change were observed.

According to all above DLS data, P60, P70, P60 without NaCl, C55, C60, and C65 were better than P40, P50, P80, and C50.

Particles: HIAC

The results of the HIAC measurements of the agitation study are shown below in Table 12:

TABLE 12

| | | Differential Counts/mL | |
|---|---|---|---|
| Sample | Particle Size (μm) | T0 | Agitation, 100 rpm, 25° C., 5 days |
| P40 | ≥5 | 1704 | 2593 |
| | ≥10 | 97 | 163 |
| | ≥25 | 8 | 0 |
| P50 | ≥5 | 4600 | 7378 |
| | ≥10 | 600 | 815 |
| | ≥25 | 15 | 0 |

TABLE 12-continued

| Sample | Particle Size (μm) | Differential Counts/mL | |
|---|---|---|---|
| | | T0 | Agitation, 100 rpm, 25° C., 5 days |
| P60 | ≥5 | 1052 | 1245 |
| | ≥10 | 112 | 134 |
| | ≥25 | 0 | 0 |
| P70 | ≥5 | 171 | 2860 |
| | ≥10 | 15 | 341 |
| | ≥25 | 0 | 8 |
| P80 | ≥5 | 15830 | 15104 |
| | ≥10 | 5786 | 4104 |
| | ≥25 | 630 | 341 |
| P60 without NaCl | ≥5 | 289 | 149 |
| | ≥10 | 52 | 23 |
| | ≥25 | 0 | 0 |
| C50 | ≥5 | 200 | 200 |
| | ≥10 | 23 | 15 |
| | ≥25 | 0 | 0 |
| C55 | ≥5 | 223 | 319 |
| | ≥10 | 23 | 23 |
| | ≥25 | 0 | 0 |
| C60 | ≥5 | 408 | 497 |
| | ≥10 | 15 | 23 |
| | ≥25 | 0 | 0 |
| C65 | ≥5 | 445 | 512 |
| | ≥10 | 8 | 0 |
| | ≥25 | 0 | 0 |

During the agitation study, P70 had a significant increase in the particle number after agitating at 25° C. for 5 days, and all other formulations had comparable particle numbers.

SUMMARY

Overall, P60 and C60 stood out as most stable formulations compared to the others. Therefore, it was concluded that ATB200 was most stable in a range of 5.0-6.0. However, no distinction could be made between phosphate and citrate buffer. In addition, the absence of sodium chloride in the formulation didn't show significant impact on ATB200 stability.

Formulation Example 2: Freeze-Thaw

Three formulations were evaluated for stability during the freeze-thaw process. The three formulations are summarized below in Table 13 below. The target concentration of ATB200 enzyme was 5 mg/mL.

TABLE 13

| Sample | Buffer | pH | NaCl |
|---|---|---|---|
| P60 | 25 mM Phosphate | 6.0 | 50 mM |
| C60 | 25 mM Citrate | | |
| CP60 | 25 mM Phosphate-Citrate buffer | | |

Sample Preparation

The ATB200 DS was buffer exchanged into the 3 formulation buffers using dialysis cassette (20000 MWCO). Dialyses were performed at 5° C. with a gentle stirring, each using three buffer changes, once every 6~10 hours.

After each dialysis, appropriate volume of formulation buffer was added to adjust the final UV concentration to 5 mg/mL. The solutions were then aseptically filtered with 0.22-μm PES filter. Each formulation was then aseptically filled into 2-mL glass vials in a bio-safety hood with the filling volume of 500 μL~1000 μL according to the sample amount requirement of analytical tests. Vials were stoppered and then crimp-oversealed immediately after filling.

Before freeze-thaw vials were taken for each formulation and the remaining sample vials were subjected to the designed freeze-thaw cycles. After-freeze-thaw sample vials were taken at pre-defined sampling points.

Sample Testing

Three freeze-thaw processes were tested, as listed below:

Process 1: uncontrolled freezing and thawing. Samples were frozen in a −80° C. freezer and thawed in a 25° C. chamber.

Process 2: controlled freezing and uncontrolled thawing. Samples were placed in a Frosty container and frozen in a −80° C. freezer. The Frosty container used isopropanol to achieve controlled freezing rate at 1° C./min. The Frosty container was placed in a 25° C. chamber to thaw the samples. The rate of temperature increase was approximately 1° C./min.

Process 3: controlled freezing and thawing. A lyophilizer was used to freeze and thaw the samples. The lowest sample temperature achieved during freezing was −47° C. The sample temperature was brought up to 25° C. The rate of temperature change for both freezing and thawing was controlled at about 0.5° C./min. Results were confirmed by repeating the experiment.

Five or three freeze-thaw cycles were performed using each process. The following tests were performed for the samples before and after freeze-thaw: Appearance, concentration (UV & Enzymatic) and SEC-HPLC. A summary of the testing parameters follows below in Table 14:

TABLE 14

| Equipment and Condition | Freezing rate and time | Heating rate and time | T0 | 1 cycle F/T | 3 cycles F/T | 5 cycles F/T |
|---|---|---|---|---|---|---|
| Refrigerator, −80° C. to 25° C. | ND, 40~60 min | ND, 40~60 min | X | X | X | X |
| Nalgene Mr. Frosty Cryo 1° C. Freezing Container, −80° C. to 25° C. | 1° C./min, 100~120 min | ~1° C./min, 100~120 min | | X | X | X |
| Lyophilizer, −47° C. to 25° C. | 0.5° C./min, ~164 min | 0.5° C./min, ~164 min | X | X | X* |

X: Appearance, Concentration (UV & Enzymatic), Enzyme activity, SEC

*: This experiment was repeated, 3 FT cycles for the first experiment and 5 FT cycles for the second experiment.

Results
Appearance—1$^{st}$ Round
The results of the first round of appearance measurements are shown below in Tables 15A and 15B:

TABLE 15A

| Sample Name | Refrigerator | | | |
|---|---|---|---|---|
| | T0 | 1 FT | 3 FT | 5 FT |
| P60 C60 CP60 | Colorless, slightly opalescent, free of visible particles | Colorless, slightly opalescent, little amount of visible particles | Colorless, slightly opalescent, more visible particles than 1 FT | Colorless, slightly opalescent, large amount of visible particles |

TABLE 15B

| Sample Name | Lyophilizer | | Mr. Frosty Container | | |
|---|---|---|---|---|---|
| | 1 FT | 3 FT | 1 FT | 3 FT | 5 FT |
| P60 C60 CP60 | Colorless, slightly opalescent, free of visible particles | Colorless, slightly opalescent, little amount of visible particles | Colorless, slightly opalescent, little amount of visible particles | Colorless, slightly opalescent, more visible particles than 1 FT | Colorless, slightly opalescent, large amount of visible particles |

At T0 (before freeze-thaw), all formulations appeared to be colorless, slightly opalescent, and free of visible particles, using corresponding formulation buffers as a reference.

After 5 cycles of quick freeze-thaw (process 1), all formulations appeared to contain more visible particles compared to their T0. CP60 contained fewest particles among the three after 5 FT.

After 5 cycles of slow freeze-thaw (process 2), all formulations appeared to contain more visible particles than T0, whereas less than the ones treated by process 1. Fewer particles were observed in CP60 samples after 5 FT cycles than in P60 and C60 samples after 1 FT cycle.

After 3 cycles of slow freeze-thaw (process 3), all formulations appeared to have more visible particles than T0. There was no difference among the three formulations.

Appearance—2$^{nd}$ Round
The results of the second round of appearance measurements are shown below in Tables 16:

TABLE 16

| Sample | Refrigerator | | | |
|---|---|---|---|---|
| | T0 | 1 FT | 3 FT | 5 FT |
| P60 C60 | Colorless, slightly opalescent, few visible | Colorless, slightly opalescent, little | Colorless, slightly opalescent, more visible | Colorless, opalescent, large amount of visible protein particles |

TABLE 16-continued

| Sample | Refrigerator | | | |
|---|---|---|---|---|
| | T0 | 1 FT | 3 FT | 5 FT |
| CP60 | particles | amount of visible particles (more than T0) | particles | Colorless, slightly opalescent, little amount of visible particles (compare to 3 FT) |
| Buffers (P60, C60, and CP60) | Colorless, clear, free of visible particles | | | |

In 2nd round of slow freeze-thaw study (process 3), more FT cycles were carried out than the first round. There were large number of visible particles appeared in P60 after 5 FT compared to T0, whereas small number of particles were observed both in C60 and CP60.

4-MUG Enzymatic Concentration and Activity
The results of the 4-MUG enzymatic concentration and activity measurements are shown below in Table 17 (processes 1-2 and first round of process 3) and Table 18 (second round of process 3):

TABLE 17

| | T0 | | Refrigerator 5 FT | | Mr. Frosty Container 5 FT | | Lyophilizer 5 FT | |
|---|---|---|---|---|---|---|---|---|
| Sample Name | Conc., mg./ml | Activity, U/L | Conc., mg./ml | Activity, U/L | Conc., mg./ml | Activity, U/L | Conc., mg./ml | Activity, U/L |
| P60 | 3.33 | 18711.6 | 3.09 | 17338.9 | 3.23 | 18145.9 | 2.77 | 15840.0 |
| C60 | 3.45 | 19353.9 | 3.27 | 18335.3 | 3.35 | 18803.1 | 3.37 | 19565.6 |
| CP60 | 3.32 | 18659.8 | 3.34 | 18748.2 | 3.23 | 18106.9 | 3.01 | 17349.1 |

TABLE 18

| | Lyophilizer | | | | | | | |
|---|---|---|---|---|---|---|---|---|
| | T0 | | 1 FT | | 3 FT | | 5 FT | |
| Sample Name | Conc., mg./ml | Activity, U/L | Conc., mg./ml | Activity, U/L | Conc., mg./ml | Activity, U/L | Conc., mg./ml | Activity, U/L |
| P60 | 3.09 | 17252.8 | 2.51 | 13954.9 | 1.45 | 7925.3 | 0.96 | 4973.7 |
| C60 | 2.98 | 16608.8 | 3.36 | 18816.8 | 3.06 | 16931.2 | 3.80 | 20606.3 |
| CP60 | 2.97 | 16561.6 | 2.93 | 16375.3 | 2.76 | 15261.8 | 0.99 | 5157.5 |

After 5 cycles of quick freeze-thaw (process 1), a slight decrease in 4-MUG enzymatic concentration was observed in P60 when compared to the T0 sample, while no significant difference in C60 and CP60 was observed.

After 5 cycles of slow freeze-thaw using a Frosty container (process 2), no significant difference was observed compared to T0 samples, in any of the 3 formulations.

After 3 cycles of slow freeze-thaw using a lyophilizer (process 3), there was distinct enzymatic concentration decrease in both P60 and CP60, but no significant change in C60, when compared to T0. The freeze-thaw with process 3 was repeated with 5 cycles and same trend was observed. Enzymatic concentration of P60 samples dropped 18.8% after 1 cycle of F/T, and became worse after 3 cycles (decreased by 53.1%) and 5 cycles (decreased by 68.9%). In CP60, enzymatic concentration started to drop after 3 cycles, and finally decreased to the same level as P60 after 5 cycles. In C60, there was almost no change after 5 cycles of slow freeze-thaw.

The 4-MUG enzymatic concentration results showed that the freezing/heating rate, number of F/T cycles and buffer type might impact ATB200 stability. The citrate buffer system (C60) provided good stabilizing effect regardless of the freeze-thaw process used.

The 4-MUG enzyme activity change trend was the same as the 4-MUG enzymatic concentration.

During quick freeze-thaw study (process 1), a slight decrease in enzyme activity happened in P60 after 5 cycles, no significant change was observed in C60 and CP60.

No distinct change was observed in any sample during slow freeze-thaw study with 1° C./min temperature change (process 2).

In the slow freeze-thaw study with a lyophilizer (process 3), the enzyme activity in P60 had an obvious decrease and in CP60 had a slight decrease. However, there was almost no change in C60. During the 2nd round of process 3 slow freeze-thaw study, the enzyme activity of P60 decreased 19.1% after 1 cycle, 54.1% after 3 cycles) and 71.2% after 5 cycles. In CP60, the enzyme activity started to drop after 3 cycles, dropped to a similar level to P60 after 5 cycles. There was negligible change in C60 after 5 cycles.

Purity: SEC-HPLC

The results of the purity measurements are shown below in Table 20 (processes 1-2 and first round of process 3) and Table 21 (second round of process 3):

TABLE 20

| | | | Refrigerator | | | Mr. Frosty Container | | | Lyophilizer | |
|---|---|---|---|---|---|---|---|---|---|---|
| Sample | SEC | T0 | 1 FT | 3 FT | 5 FT | 1 FT | 3 FT | 5 FT | 1 FT | 3 FT |
| P60 | Monomer % | 99.7 | 99.7 | 99.6 | 99.5 | 99.7 | 99.7 | 99.7 | 93.4 | 92.1 |
| | HMW % | 0.2 | 0.2 | 0.2 | 0.2 | 0.3 | 0.2 | 0.2 | 5.8 | 7.6 |
| | LMW % | 0.0 | 0.2 | 0.2 | 0.3 | 0.1 | 0.1 | 0.1 | 0.9 | 0.3 |
| C60 | Monomer % | 99.8 | 99.9 | 99.9 | 99.9 | 99.8 | 99.8 | 99.8 | 99.7 | 99.9 |
| | HMW % | 0.2 | 0.2 | 0.1 | 0.1 | 0.2 | 0.2 | 0.2 | 0.2 | 0.1 |
| | LMW % | ND | ND | ND | ND | ND | ND | ND | 0.2 | ND |
| CP60 | Monomer % | 99.8 | 99.7 | 99.7 | 99.7 | 99.8 | 99.8 | 99.8 | 99.6 | 99.9 |
| | HMW % | 0.2 | 0.2 | 0.2 | 0.2 | 0.2 | 0.2 | 0.2 | 0.2 | 0.1 |
| | LMW % | ND | 0.1 | 0.1 | 0.1 | ND | ND | ND | 0.2 | ND |

TABLE 21

| Sample | | | Lyophilizer | | |
|---|---|---|---|---|---|
| Name | SEC | T0 | 1 FT | 3 FT | 5 FT |
| P60 | Monomer % | 99.8 | 87.8 | 54.4 | 31.8 |
| | HMW % | 0.2 | 12.2 | 45.6 | 68.2 |
| | LMW % | ND | ND | 0.1 | <0.1 |
| C60 | Monomer % | 99.8 | 99.8 | 99.8 | 99.7 |
| | HMW % | 0.2 | 0.2 | 0.2 | 0.3 |
| | LMW % | ND | ND | ND | ND |
| CP60 | Monomer % | 99.8 | 99.6 | 98.3 | 31.3 |
| | HMW % | 0.2 | 0.4 | 1.7 | 68.7 |
| | LMW % | ND | ND | <0.1 | <0.1 |

No SEC monomer percentage change was detected in any sample after up to 5 cycles of quick F/T (process 1) or slow F/T (process 2).

In the first slow F/T study (process 3), P60 samples showed obvious SEC monomer percentage decline (mainly due to formation of HMW species) after 3 cycles. And no distinct change happened in C60 and CP60. In the 2nd process 3 slow F/T study (0.5° C./min), the monomer in P60 samples started to drop after 1 cycle and finally dropped 68.1% after 5 cycles. And in CP60, the monomer percentage stated to drop after 3 cycles, but to a much less extent than in P60; however, it reached the same level as in P60 after 5 cycles. There was no change on monomer percentage in C60 after up to 5 cycles.

The SEC purity results were consistent with the performance in enzymatic concentration and activity, confirming that freezing/heating rate, number of F/T cycles and buffer type might impact ATB200 stability during freeze-thaw process. Buffers containing sodium phosphate did not protect ATB200 as well during freeze-thaw cycles, based on the SEC results.

Summary

ATB200 formulated in citrate buffer (C60) withstood multiple freeze-thaw cycles better than the other two buffers (P60 and CP60). Regardless of the freeze-thaw process, ATB200 remained stable in citrate buffer.

Formulation Example 3: Excipient

Eight formulations (E1-8) were prepared with various excipients. The ATB200 enzyme concentration in excipient evaluation study was 5 mg/mL. Three buffers, two stabilizers and one surfactant were selected to assess the protein stability in formulations described in Table 22 below.

TABLE 22

| Sample | Buffer | pH | NaCl | Trehalose | Mannitol | Polysorbate 80 |
|---|---|---|---|---|---|---|
| E1 | 25 mM Phosphate | 6.0 | 50 mM | 2% | / | 0.05% |
| E2 | | | | / | 2% | 0.05% |
| E3 | 25 mM Citrate | | | 2% | / | 0.05% |
| E4 | | | | / | 2% | 0.05% |
| E5 | 25 mM Phosphate | | | / | 2% | / |
| E6 | 25 mM Citrate | | | / | 2% | / |
| E7 | 25 mM Phosphate- | | | 2% | / | 0.05% |
| E8 | Citrate combination buffer | | | / | 2% | 0.05% |

Sample Preparation 25 mM sodium phosphate buffer containing 50 mM NaCl at pH 6.0, 25 mM sodium citrate buffer containing 50 mM NaCl at pH 6.0, and 25 mM sodium phosphate-citrate combination buffer containing 50 mM NaCl at pH 6.0 were prepared separately. The ATB200 enzyme solution was exchanged into the three buffers using dialysis cassette. Dialyses were carried out at 5° C. with a gentle stirring, each with 3 buffer changes, once every 6~10 hours.

After dialysis, trehalose, mannitol or PS80 were added to the dialysate to prepare the formulations as listed in Table 22. Finally, appropriate volume of formulation buffers was added to adjust the final ATB200 concentration to 5 mg/mL. The solutions were aseptically filtered with 0.22-µm PES filter.

Each formulation was aseptically filled into 2-mL glass vials in a bio-safety hood with about 1 mL filling volume. Vials were stoppered and then crimped immediately after filling.

Sample Testing

Formulations E1-8 were tested under 4 different conditions. Vials of each formulation were stored at 5° C. for 12 weeks (12W) and 40° C. for 8 weeks (8W), freeze-thawed (0.5° C./min) for 5 cycles and agitated at 100 rpm for 5 days at 25° C. The sampling and testing plan is described in Table 23. Samples were tested initially (T0), 2 weeks (2W), 4 weeks (4W), 8 weeks (8W) and 12 weeks (12W).

TABLE 23

| Treatment Condition | T0 | 2 W | 4 W | 8 W | 12 W |
|---|---|---|---|---|---|
| Storage at 5° C. | X | X | X | X | X |
| Storage at 40° C. | | X | X | X | / |

TABLE 23-continued

| Treatment Condition | T0 | 2 W | 4 W | 8 W | 12 W |
|---|---|---|---|---|---|
| Freeze-Thaw, −80° C. to 25° C. in freezer and −47° C. to 25° C. using lyophilizer | | 1 cycle X | 3 cycles X | 5 cycles X | |
| Agitation, 100 rpm, 25° C. | | 5 Days X, (Z) | | / | |

X: Appearance measurement

Results

Appearance

The results of the appearance for the freeze-thaw study measurements are shown below in Table 24 (using refrigerator) and Table 25 (using lyophilizer):

TABLE 24

| | | Freezer | | |
|---|---|---|---|---|
| | T0 | 1 FT | 3 FT | 5 FT |
| E1 E2 E3 E4 | Colorless, slightly opalescent, free of visible particles | Colorless, slightly opalescent, free of visible particles | | |
| E5 | | Colorless, slightly opalescent, numerous tiny visible particles | Colorless, opalescent, numerous visible particles | Colorless, opalescent, numerous visible particles |
| E6 | | Colorless, clear, free of visible particles | Colorless, opalescent, numerous tiny visible particles | Colorless, opalescent, numerous tiny visible particles |
| E7 E8 | | Colorless, slightly opalescent, free of visible particles | | |

TABLE 25

| | | Lyophilizer | | |
|---|---|---|---|---|
| | T0 | 1 FT | 3 FT | 5 FT |
| E1 E2 E3 E4 | Colorless, slightly opalescent, free of visible particles | Colorless, slightly opalescent, free of visible particles | | |
| E5 | | Colorless, opalescent, numerous visible particles | Colorless, opalescent, numerous visible particles | Colorless, opalescent, numerous visible particles |

TABLE 25-continued

| | Lyophilizer | | |
|---|---|---|---|
| T0 | 1 FT | 3 FT | 5 FT |
| E6 | Colorless, opalescent, numerous tiny visible particles | Colorless, opalescent, numerous tiny visible particles | Colorless, opalescent, numerous tiny visible particles |
| E7 | Colorless, slightly opalescent, free of visible particles | | |
| E8 | | | |

During the freeze-thaw study, visible particles slightly increased with the increase of freeze-thaw cycles in F5 and F6, which did not contain PS80. No difference was observed in other formulations.

Summary

Formulations without PS80 (F5 and F6) did not perform as well as the formulations with PS80 in the freeze-thaw study, evidenced by the formation of visible particles after multiple freeze-thaw cycles.

Formulation Example 4: Hemolysis in Whole Human Blood

A series of dilutions of blood (1:2, 1:3, 1:4, 1:5, and 1:10) from a human donor were prepared in saline. When mixed with de-ionized water, the dilution that resulted in an OD at 540 nm between 0.8 and 1.2 was used in the assay and is referred to as the blood substrate. Four types of samples were tested: the test article, placebo, positive control and negative control. The test article featured ATB200 rhGAA in a formulation with 25 mM sodium citrate, 2% mannitol and 0.05% polysorbate 80 at a pH of 6.0. The placebo was the same as the test article except there was no ATB200 rhGAA. The positive control article was sterile water for injection and had a pH of 5. The negative control article was saline (0.9 NaCl) and had a pH of 5.

The test article (ATB200) at 300, 600 and 1000 µg/ml with saline, the placebo with saline, the negative control (saline) and the positive control (water) were mixed with the blood substrate from the human donor. Samples were incubated without agitation for 1 hour at 37° C. After incubation, the tubes were centrifuged for 10 minutes at approximately 100× g at room temperature. The amount of hemoglobin in the supernatant of each sample was analyzed spectrophotometrically at 540 nm.

The percent hemolysis for the test article was determined by the formula:

$$\% \text{ hemolysis} = \frac{\text{Abs. of } TA/\text{placebo w/blood} - \text{Abs. of saline w/blood} - \text{Abs. of } TA/\text{placebo}}{\text{Abs. of water w/blood} - \text{Abs. of saline w/blood}}$$

The percent hemolysis of water plus blood is 100%. Saline was the negative control. Hemolysis less than or equal to 10% was considered insignificant. The percent hemolysis was calculated for each concentration of the test article and for the placebo.

Table 26 below shows the results of the samples tested.

TABLE 26

| Treatment | Concentration (µg/mL) | $OD_{540}$ Without Blood | $OD_{540}$ With Blood | % Hemolysis* |
|---|---|---|---|---|
| Saline[a] | — | — | 0.016 | — |
| Water[b] | — | — | 1.002 | 100 |
| ATB200 | 300 | 0.001 | 0.016 | −0.10 |
| ATB200 | 600 | 0.002 | 0.003 | −1.52 |
| ATB200 | 1000 | 0.003 | 0.004 | −1.52 |
| Placebo for ATB200 | —[c] | 0.000 | 0.003 | −1.32 |
| Placebo for ATB200 | —[d] | 0.000 | 0.003 | −1.32 |
| Placebo for ATB200 | —[e] | 0.003 | 0.028 | 0.91 |

[a] = negative control for hemolysis
[b] = positive control for hemolysis
[c] = placebo diluted in saline in the same ratio as the 300 µg/mL test article
[d] = placebo diluted in saline in the same ratio as the 600 µg/mL test article
[e] = placebo diluted in saline in the same ratio as the 1000 µg/mL test article
*% hemolysis was determined using the OD for the water as the positive control Incubation of the human blood substrate with the three samples of placebo, diluted in saline in the same ratio as the three test article doses, did not cause any significant hemolysis of the human blood. The percent hemolysis for the placebo-diluted samples was calculated to be −1.3, −1.3, and 0.9%, respectively. Incubation of the human blood substrate with ATB200 at 300, 600 and 1000 µg/ml did not cause any significant hemolysis of the human blood. The percent hemolysis for the test article samples was calculated to be −0.1, −1.5% and −1.5%, respectively.

In conclusion, the ATB200 formulation was compatible with human blood at all dilutions.

Formulation Example 5: Flocculation in Human Plasma and Serum

Test article dosing solutions (3 concentrations) and the placebo (3 concentrations) were mixed with equal volumes of human plasma and serum from a donor. The test article featured ATB200 rhGAA in a formulation with 25 mM sodium citrate, 2% mannitol and 0.05% polysorbate 80 at a pH of 6.0. The placebo was the same as the test article except there was no ATB200 rhGAA.

One ml of each dose of test article or placebo, was mixed with an equal volume of plasma, serum and saline. Samples were incubated for 30 minutes at room temperature. After incubation the tubes were examined macroscopically and microscopically for precipitation or coagulation. An aliquot from each tube was centrifuged at 14,000 rpm in a microcentrifuge for 10 minutes. Each tube was examined for the presence or absence of a pellet. Precipitation/coagulation and pellets were scored as follows:

0=negative
1=very slight precipitation or pellet
2=minimal precipitation or pellet
3=moderate precipitation or pellet
4=significant precipitation or pellet Table 27 below shows the results of the samples tested.

TABLE 27

| Treatment | Final Concentration (μg/mL) | Plasma | | | Serum | | | Saline | | |
|---|---|---|---|---|---|---|---|---|---|---|
| | | Macro | Micro | Pellet | Macro | Micro | Pellet | Macro | Micro | Pellet |
| Placebo for ATB200 | —[a] | 0 | 0 | 0 | 0 | 0 | 0 | — | — | — |
| Placebo for ATB200 | —[b] | 0 | 0 | 0 | 0 | 0 | 0 | — | — | — |
| Placebo for ATB200 | —[c] | 0 | 0 | 0 | 0 | 0 | 0 | — | — | — |
| ATB200 | 300 | 0 | 0 | 0 | 0 | 0 | 0 | 0 | 0 | 0 |
| ATB200 | 600 | 0 | 0 | 0 | 0 | 0 | 0 | 0 | 0 | 0 |
| ATB200 | 1000 | 0 | 0 | 0 | 0 | 0 | 0 | 0 | 0 | 0 |

[a] = placebo was diluted in saline in the same ratio as the 300 μg/mL final concentration test article dosing formulation
[b] = placebo was diluted in saline in the same ratio as the 600 μg/mL final concentration test article dosing formulation
[c] = placebo was diluted in saline in the same ratio as the 1000 μg/mL final concentration test article dosing formulation No precipitation was observed macroscopically or microscopically in the human plasma or serum when mixed with each ATB200 concentration. No precipitation was noted in the placebo samples. When all placebo or ATB200 samples were centrifuged, no pellets were observed.

Based on the results of this study, the ATB200 formulation was found to be compatible with human plasma and serum up to and including a final concentration of 1000 μg/ml.

Example: Pharmacokinetic and Safety Data on Recombinant Acid A-Glucosidase ATB200 Co-Administered with Miglustat in ERT-Experienced and ERT-Naïve Patients with Pompe Disease This study was designed to primarily evaluate the safety, tolerability, and pharmacokinetics (PK) of ATB200 co-administered with miglustat. A PK/pharmacodynamic (PD) translational model from Gaa knockout mouse predicted that a combination of ATB200 20 mg/kg with a high dose (e.g. 260 mg) of miglustat in humans would provide optimal glycogen reduction.

In the description below, "high dose" of miglustat refers to a dose of about 260 mg and "low dose" of miglustat refers to a dose of about 130 mg.

The objective was to evaluate the preliminary total GAA protein, ATB200 and miglustat PK data, and safety markers from 10 patients in this of this phase 1/2 study.

Figure 21:
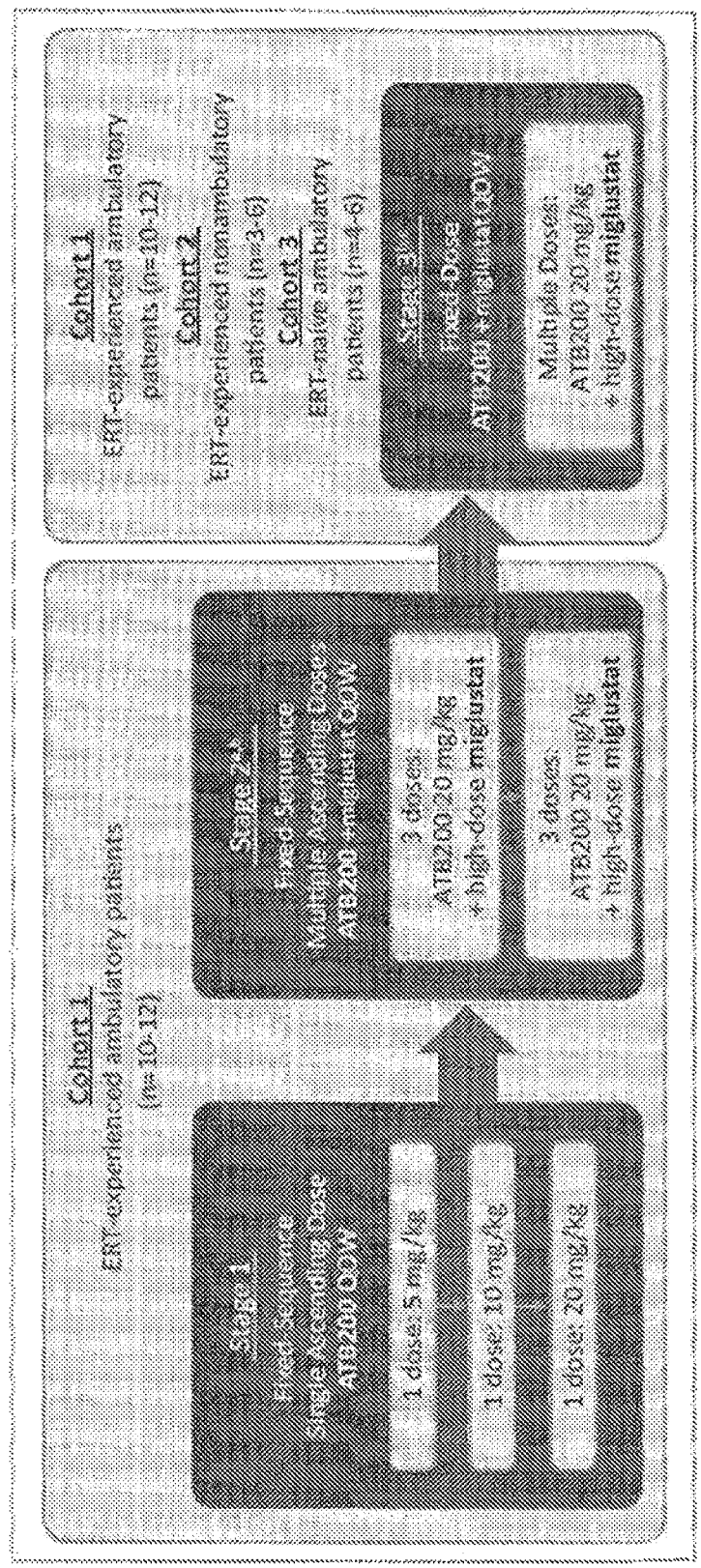
FIG. 21 shows the study design of an open-label, fixed-sequence, ascending-dose, first-in-human, phase 1/2 study to assess the safety, tolerability, PK, PD, and efficacy of intravenous infusions of ATB200 co-administered with oral miglustat in adults with Pompe disease.

This is an open-label, fixed-sequence, ascending-dose, first-in-human, phase 1/2 study to assess the safety, tolerability, PK, PD, and efficacy of intravenous infusions of ATB200 co-administered with oral miglustat in adults with Pompe disease (FIG. 21). Mean total GAA protein and miglustat PK results from the first 8 Cohort 1 patients through Visit 9 and the first 2 Cohort 3 patients were assessed.

[a]Safety data from 2 sentinel patients from Cohort 1 were reviewed at each dose level before dosing in Cohorts 2 and 3.
[b]During Stages 2 and 3, miglustat was orally administered prior to the start of ATB200 intravenous infusion. For all doses, ATB200 was intravenously infused for a 4-hour duration.
[c]The first 2 patients in Cohorts 2 and 3 served as sentinel patients for their respective cohorts. Key inclusion criteria:
  Males and females aged 18-65 years who were diagnosed with Pompe disease based on documented deficiency of GAA enzyme activity or by GAA genotyping
  Received ERT with alglucosidase alfa for 2-6 years (or ≥2 years for Cohort 2) prior to trial initiation (Cohort 1)
  Currently receiving alglucosidase alfa at a frequency of every other week and completed the last 2 infusions without a drug-related adverse event resulting in dose interruption (Cohorts 1 and 2)
  Must be able to walk between 200 and 500 meters on the 6-Minute Walk Test (Cohorts 1 and 3)
  Upright forced vital capacity must be 30%-80% of predicted normal value (Cohorts 1 and 3)
  Must be wheelchair-bound and unable to walk unassisted (Cohort 2)

PK Analysis:
  Blood samples for plasma total GAA protein and activity concentration were collected
  Stage 1: prior to start of ATB200 infusion and 1, 2, 3, 3.5, 4, 4.5, 5, 6, 8, 10, 12, and 24 hour(s) post-start of infusion
  Stages 2 and 3: 1, 2, 3, 4, 4.5, 5, 6, 7, 9, 11, 13, and 25 hour(s) post-miglstat oral administration
  Blood samples for plasma miglustat concentrations were taken just prior to miglustat oral administration (time 0) and 1, 1.5, 2, 2.5, 3, 4, 5, 6, 9, 11, and 25 hour(s) after miglustat oral administration. Plasma miglustat is determined by a validated LC-MS/MS assay
  Total GAA protein concentrations in plasma for ATB200 5, 10, and 20 mg/kg were determined by a validated LC-MS/MS quantification of rhGAA-specific "signature" peptide(s)

A preliminary analysis was completed in 8 patients in Cohort 1 who completed Stages 1 and 2 and 2 patients in Cohort 3 who started Stage 3
  Initial ERT-switch patients are representative of the Pompe disease population, with mean 5.02 years on ERT (Table 28)

TABLE 28

Baseline Characteristics

| Baseline Characteristics (N = 12[a]) | ERT-Experienced Ambulatory (n = 10) | Naïve (n = 2) |
|---|---|---|
| Time on ERT (Lumizyme ®/Myozyme ®), years, mean (STDV) | 5.02 (1.2) | N/A |
| Age, years, mean (range) | 47.7 (8.19) | 33.0 (12.73) |
| Sex, M/F, % | 80/20 | 0/100 |
| 6 MWT, meters, mean (STDV) | 398.4 (95.92) | 432.1 (67.81) |
| Upright FVC, mean %, predicted (STDV) | 51.9 (13.84) | 51.0 (26.87) |

6 MWT = 6-minute walk test; FVC = forced vital capacity; N/A = not available; STDV = standard deviation.
[a]n = 10 from Cohort 1 (ambulatory ERT-switch) through interim data analysis; n = 2 from Cohort 3 (naive).

Total GAA Protein

Figure 22A:
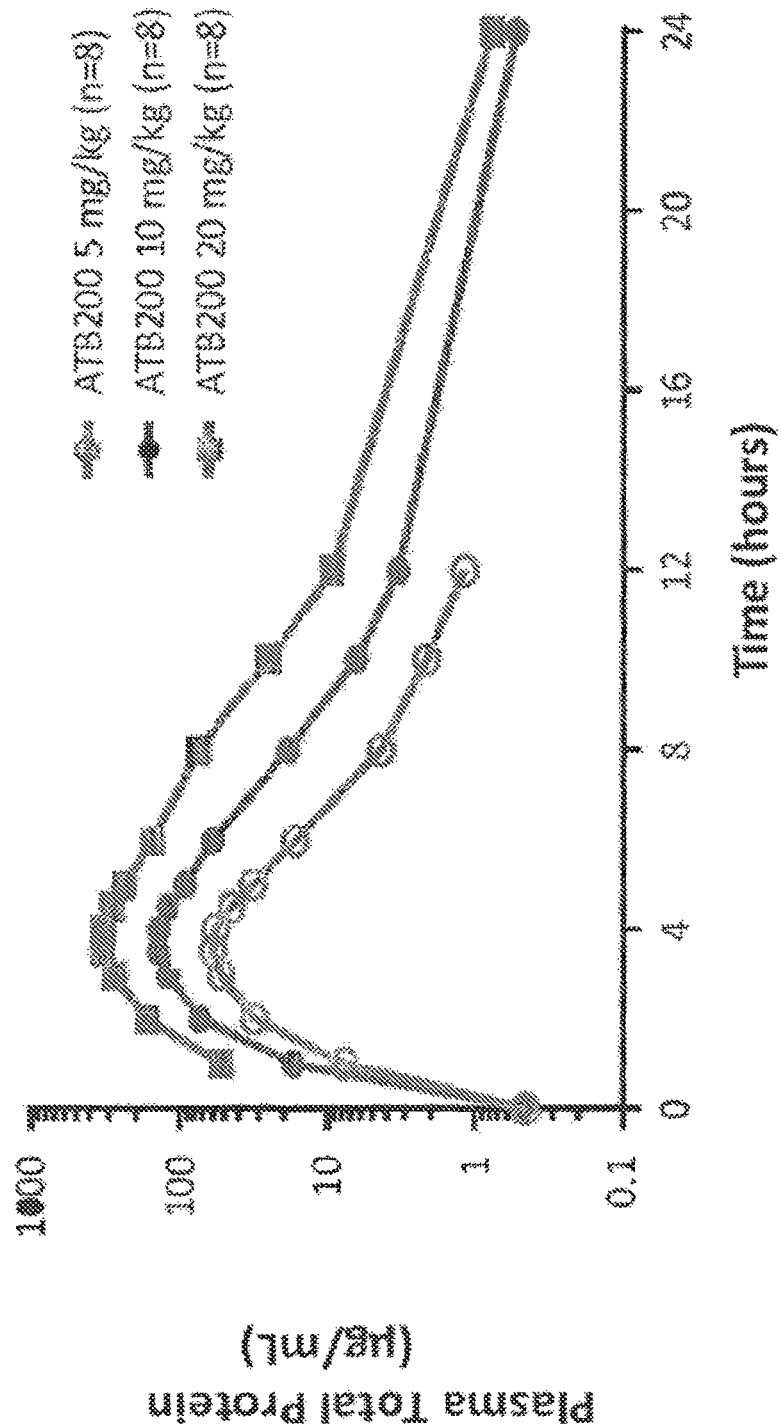
FIGS. 22A-22B are graphs showing the concentration-time profiles of GAA total protein in plasma in human subjects after dosing of 5, 10 or 20 mg/kg ATB200, 20 mg/kg ATB200 and 130 mg miglustat, or 20 mg/kg ATB200 and 260 mg miglustat.
Figure 22B:
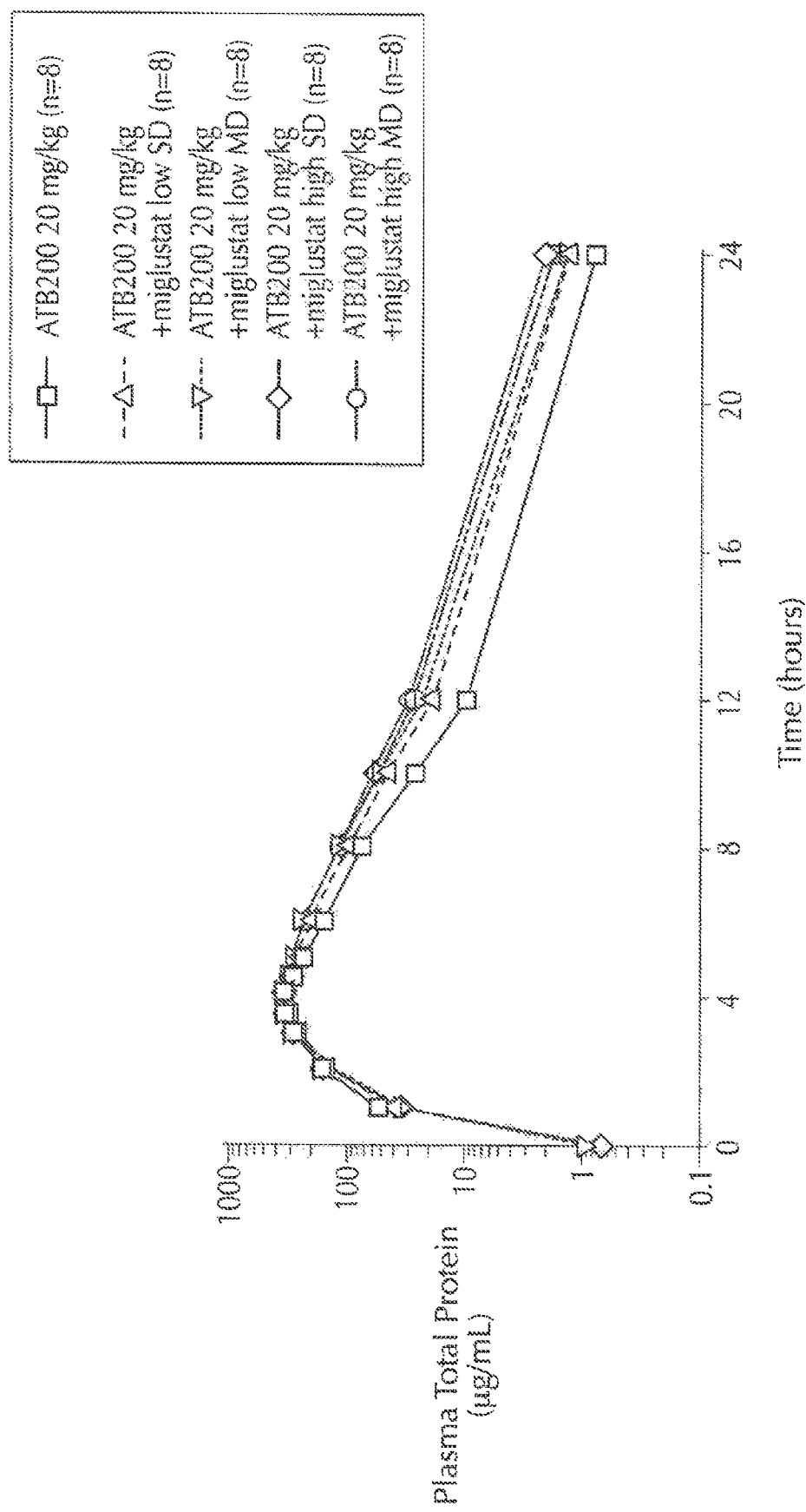
Figure 22C:
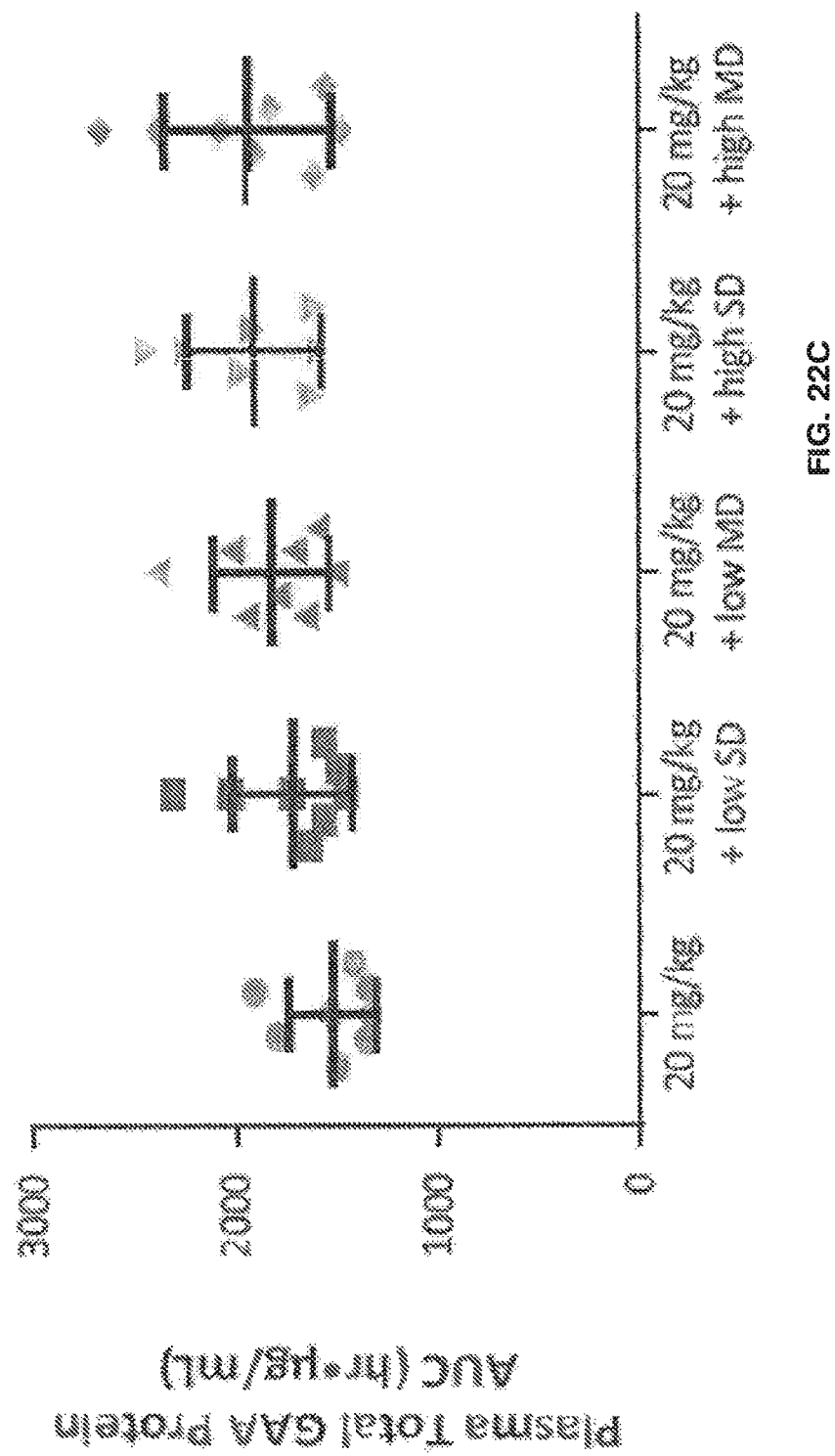
FIG. 22C is a graph showing the AUC of GAA total protein in plasma in human subjects after dosing of 20 mg/kg ATB200, 20 mg/kg ATB200 and 130 mg miglustat, or 20 mg/kg ATB200 and 260 mg miglustat.
Figure 22D:
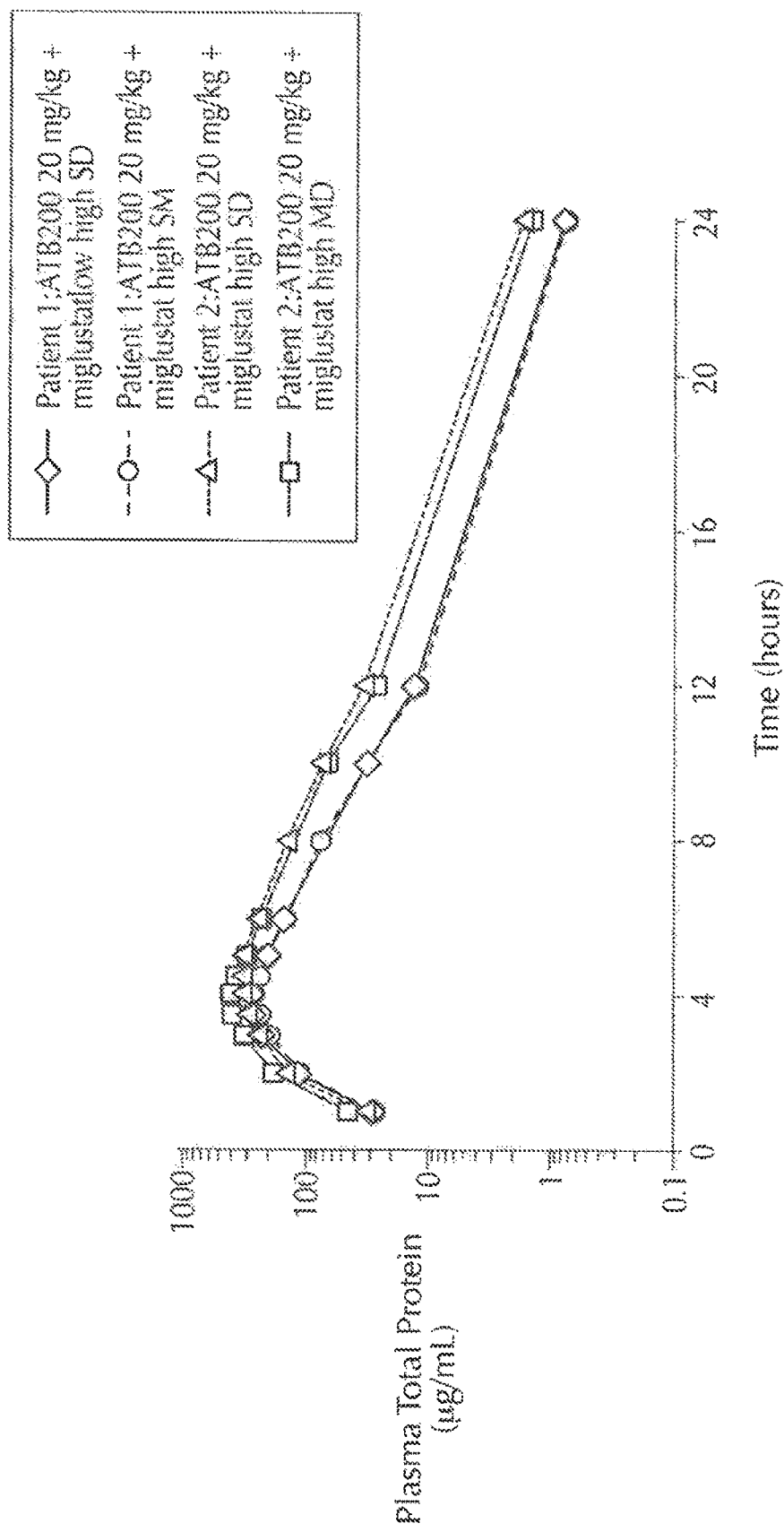
FIG. 22D is a graph showing the concentration-time profiles of GAA total protein in plasma in two individual human subjects after dosing of 20 mg/kg ATB200 and 260 mg miglustat.

When given alone, ATB200 increases in a slightly greater-than-dose-proportional manner (Table 29 and FIGS. 22A-22D). Variability appears to increase with miglustat dose (FIG. 22C). Co-administration of ATB200 20 mg/kg with the high dose of miglustat (260 mg) increased total GAA protein exposure (AUC) by approximately 25% relative to ATB200 alone at 20 mg/kg. The distribution half-life (α-phase) increased by 45%, suggesting that the high dose of miglustat stabilizes ATB200 in plasma. An increase in the distribution half-life is accompanied by an increase in AUC from time to maximum plasma concentration to approximately 12 hours post-dose. The increases in AUC and half-life can be observed on the log scale, during the terminal elimination phase (FIG. 22B). ATB200 demonstrated a relatively high volume of distribution. The disposition of plasma total GAA protein appears similar between ERT-naive (Cohort 3) and ERT-experienced patients (Cohort 1) (FIGS. 22A and 22D).

TABLE 29

Total GAA Protein

| Cohort | Treatment | $C_{max}$ (ng/mL)[a] | $t_{max}$ (hr)[b] | $AUC_{0-t}$ (ng*hr/mL)[a] | $AUC_{0-\infty}$ (ng*hr/mL)[a] | $\beta t_{1/2}$ (hr)[c] | $\alpha t_{1/2}$ (hr)[c] | $CL_T$ (L/hr)[c] | $V_{ss}$ (L)[c] |
|---|---|---|---|---|---|---|---|---|---|
| 1 | 5 mg/kg alone[d] | 61 (18.1) | 3.8 (3.0-4.0) | 215 (16.7) | 218 (16.4) | 1.9 (16.7) | 1.1 (10.2) | 2.1 (16.9) | 4.62 (12.7) |
| 1 | 10 mg/kg alone[d] | 144 (16.6) | 4.0 (3.5-4.0) | 578 (20.3) | 584 (20.4) | 1.6 (46.1) | 1.3 (10.5) | 1.59 (25.4) | 3.87 (16.5) |
| 1 | 20 mg/kg alone[d] | 345 (10.1) | 4.0 (3.5-4.0) | 1508 (14.5) | 1512 (14.4) | 2.1 (29.7) | 1.5 (6.5) | 1.22 (21.7) | 3.52 (12.4) |
| 1 | ATB200 20 mg/kg + miglustat low SD[d] | 334 (16-2) | 4.0 (3.5-4.0) | 1694 (17.7) | 1701 (17.5) | 2.4 (16.6) | 1.8 (10.2) | 1.09 (22.9) | 3.76 (13.3) |
| 1 | ATB200 20 mg/kg + miglustat low MD[d] | 353 (13.7) | 4.0 (3.5-5.0) | 1804 (15.7) | 1808 (15.8) | 2.5 (8.1) | 1.9 (21.8) | 1.02 (21.4) | 3.73 (12.3) |
| 1 | ATB200 20 mg/kg + miglustat high SD[e] | 349 (13.9) | 4.0 (3.5-4.0) | 1878 (17.5) | 1886 (17.5) | 2.7 (13.1) | 2.3 (18.9) | 0.98 (26.5) | 3.74 (12.3) |
| 1 | ATB200 20 mg/kg + miglustat high MD[d] | 356 (20.2) | 4.0 (3.5-4.0) | 1886 (21.3) | 1901 (21.7) | 2.5 (20.5) | 2.1 (16.1) | 0.98 (27.3) | 3.6 (18.7) |
| 3 | ATB200 20 mg/kg + miglustat high MD[f] | 291 (21.6) | 4.3 (4.0-4.5) | 1597 (34.8) | 1600 (34.9) | 2.4 (5.4) | 2 (14.5) | 0.69 (28.9) | 2.61 (17.3) |
| 3 | ATB200 20 mg/kg + miglustat high MD[f] | 330 (27.5) | 4.0 (4.0-4.0) | 1672 (32.7) | 1676 (32.6) | 2.6 (8.7) | 1.9 (9.0) | 0.66 (26.6) | 2.33 (23.2) |

AUC = area under the curve; $CL_T$ = total body clearance; $C_{max}$ = maximum drug concentration; CV = coefficient of variability; MD = multiple doses; SD = single dose; $t_{1/2}$ = half-life; tmax = time to maximum drug concentration; $V_{ss}$ = apparent volume of distribution in steady state.
[a]Geometric mean (CV %).
[b]Median (min-max).
[c]Arithmetic mean (CV %.)
[d]n = 8.
[e]n = 7.
[f]n = 2.

Miglustat PK

Figure 23:
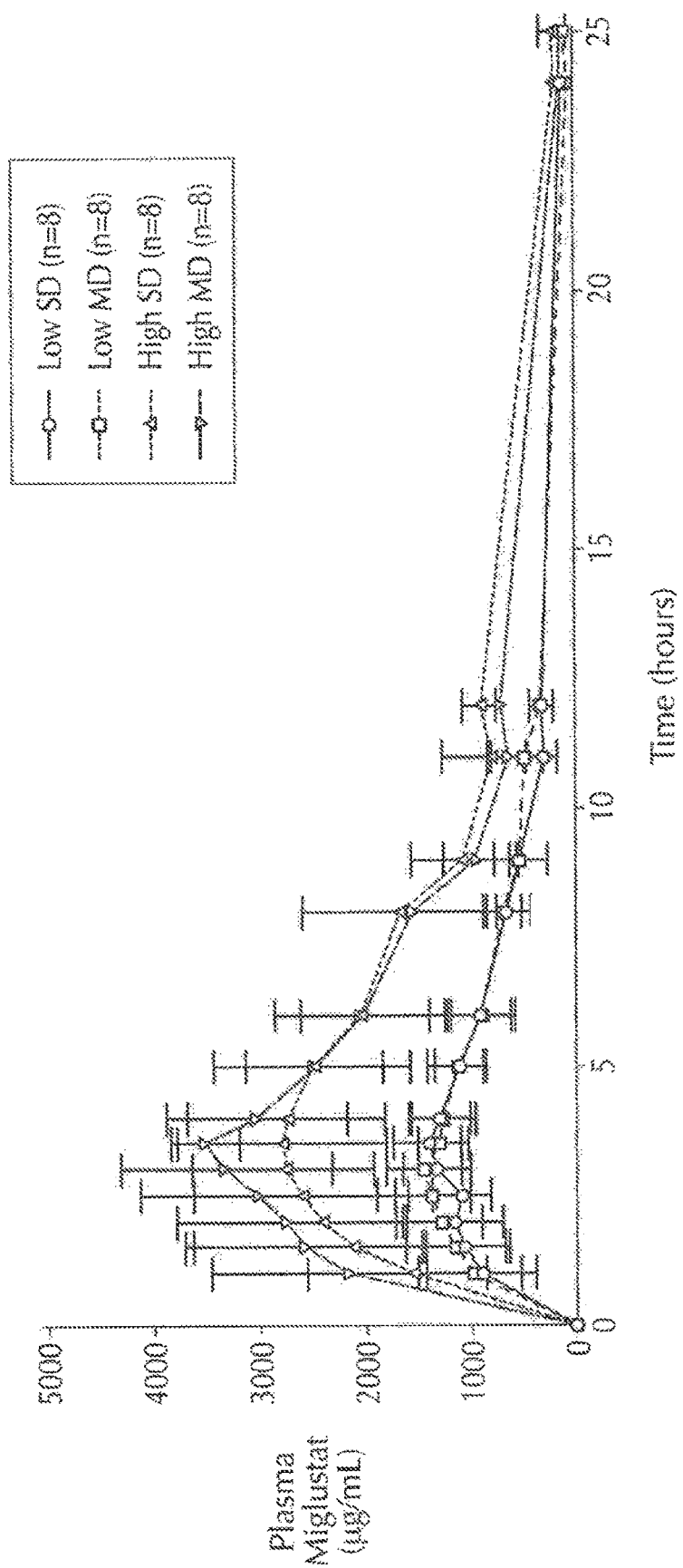
FIG. 23 is a graph showing the concentration-time profiles of miglustat in plasma in human subjects after dosing of 130 mg or 260 mg of miglustat.

Miglustat demonstrated dose-proportional kinetics (Table 30 and FIG. 23). Plasma miglustat appears similar between single and multiple doses.

TABLE 30

Miglustat PK Summary

| Treatment | $C_{max}$ (ng/mL)[a] | $t_{max}$ (h)[b] | $AUC_{0-t}$ (ng*h/mL)[a] | $AUC_{0-\infty}$ (ng*h/mL)[a] | $t1_{/2}$ (h)[c] | CL/F (L/h)[c] | $V_z$/F (L)[c] |
|---|---|---|---|---|---|---|---|
| Low SD | 1486 (29.9) | 3.5 (1.5-3.5) | 11,807 (25.6) | 12,565 (26.8) | 5.6 (11.7) | 10.6 (23) | 85.8 (23.4) |
| Low MD | 1518 (27.6) | 3.0 (1.5-3.5) | 12,254 (26.4) | 13,094 (28.3) | 5.9 (32.1) | 10.2 (23.9) | 86.7 (43.9) |
| High SD | 3059 (36.1) | 3.5 (1.5-5) | 23,999 (35) | 25,859 (34.4) | 5.7 (29.9) | 10.6 (33) | 86.3 (45.7) |
| High MD | 3569 (25.5) | 3.0 (1.0-4.0) | 24,970 (24.1) | 25,972 (23) | 5.3 (15.6) | 10.3 (26.4) | 81 (41.8) |

$V_z$ = apparent volume of distribution in terminal state.
[a]Geometric mean (CV %).
[b]Median (min-max).
[c]Arithmetic mean (CV %).

Pharmacodynamics

Figure 24A:
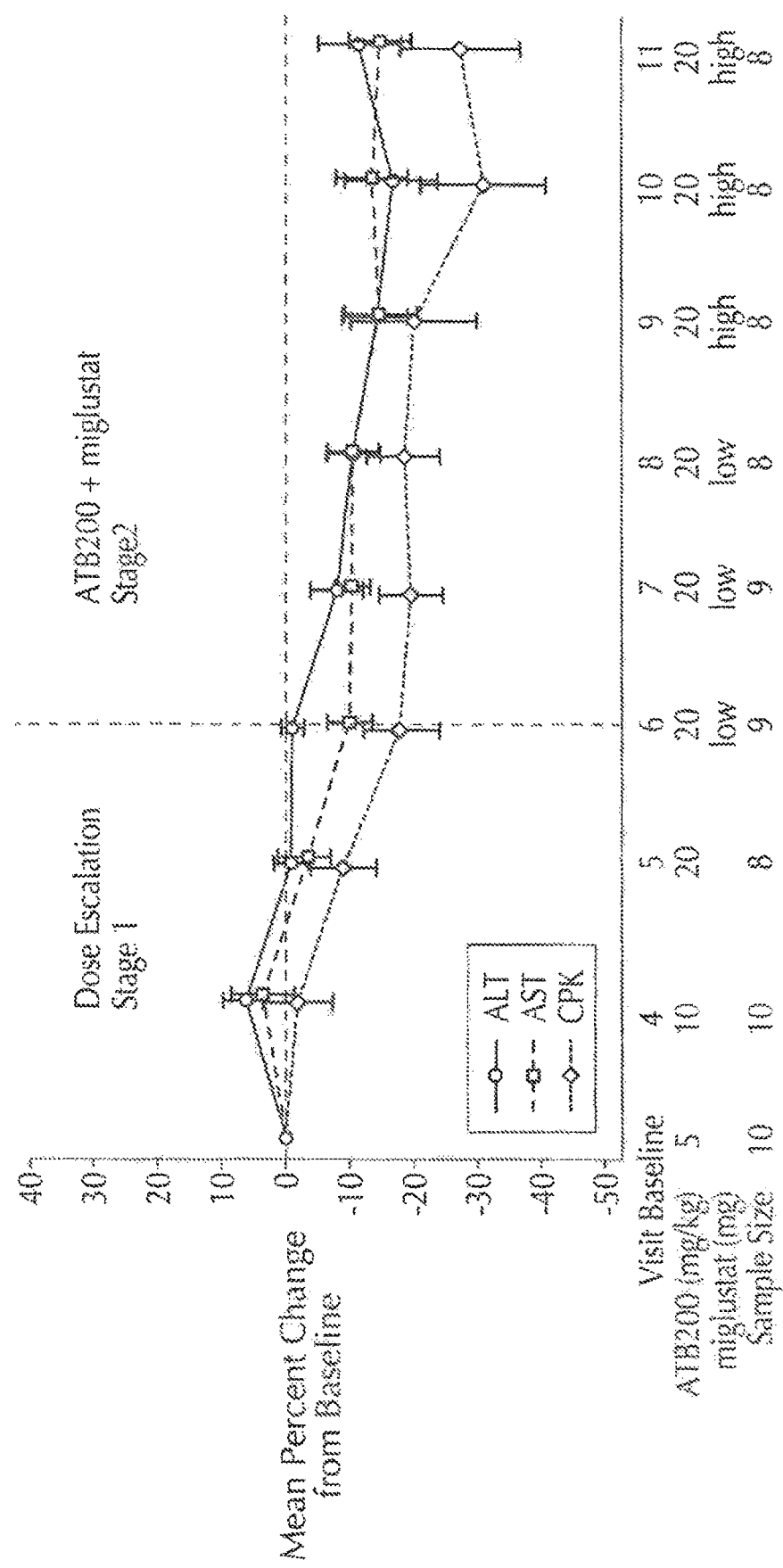
FIGS. 24A-24D are graphs showing changes in alanine aminotransferase (ALT), aspartate aminotransferase (AST), creatine phosphokinase (CPK) and hexose tetrasaccharide (Hex4) levels in human patients after administration of ascending doses of ATB200 (5, 10 and 20 mg/kg) followed by co-administration of ATB200 (20 mg/kg) and miglustat (130 and 260 mg).
Figure 24B:
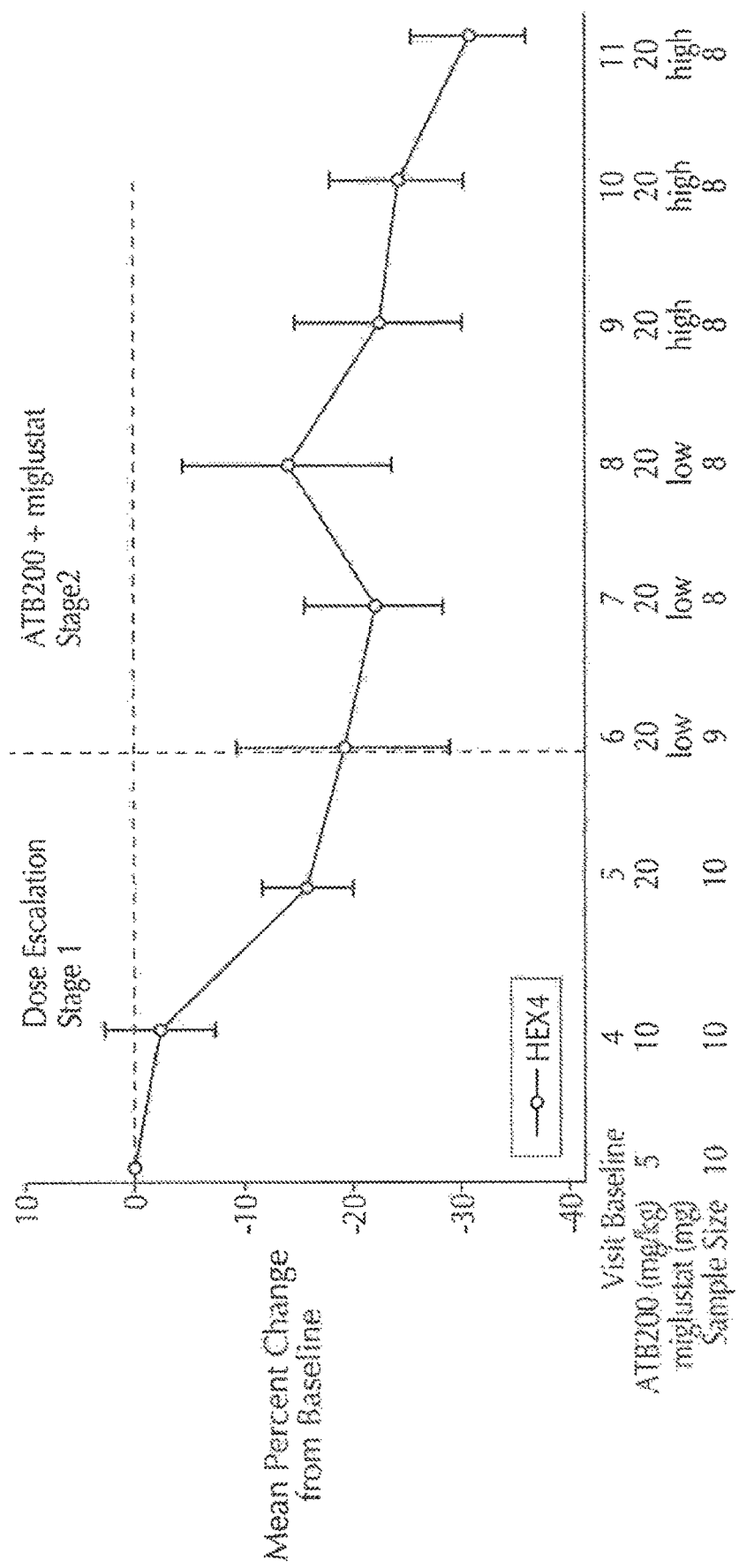
Figure 24C:
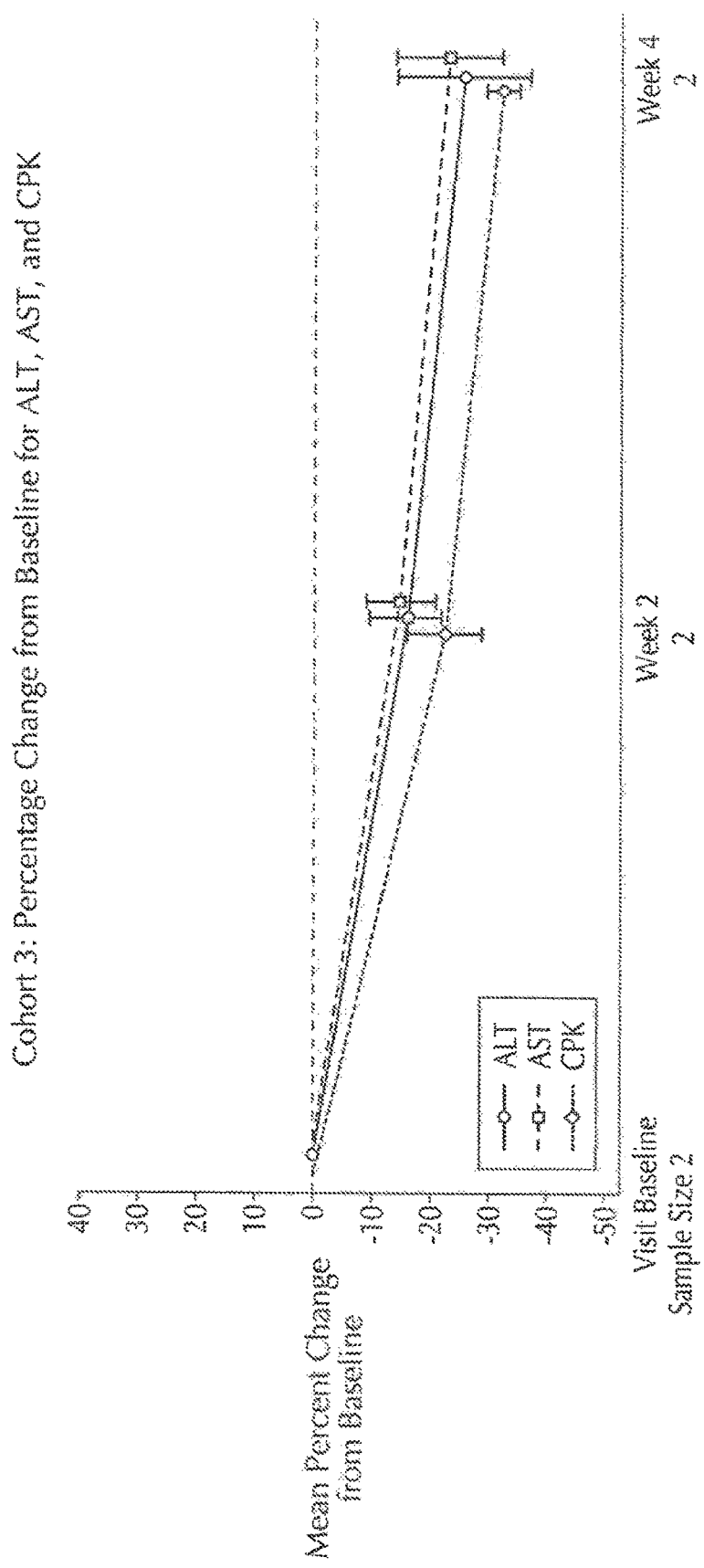
Figure 24D:
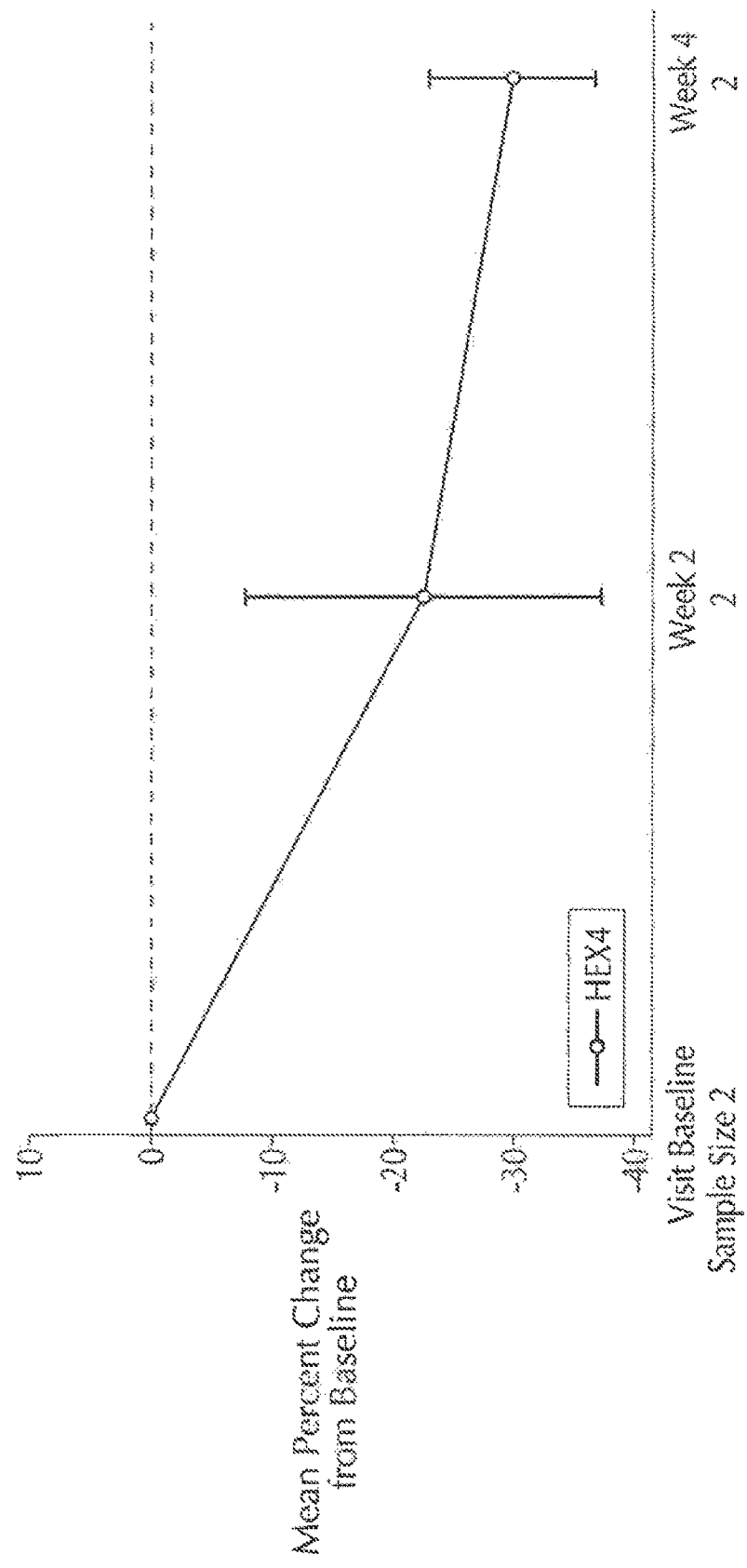

By the 11th visit in ERT-experienced patients from Cohort 1 (FIGS. 24A and 24B):

- Alanine aminotransferase (ALT) decreased in 5 of 8 patients; 4/4 patients with elevated baseline levels normalized
- Aspartate aminotransferase (AST) decreased in 6 of 8 patients; 3/4 patients with elevated baseline levels normalized
- Creatine phosphokinase (CPK) decreased in 6 of 8 patients; 2/6 patients with elevated baseline levels normalized
- Urine glucose tetrasaccharide (HEX4) levels decreased in 8 of 8 patients By week 4, all 4 biomarker levels decreased in the 2 patients in the treatment-naive cohort (Cohort 3) (FIGS. 24C and 24D).

In FIG. 24A-24D, data are represented as mean±standard error.

Safety

- No serious adverse events (AEs) or infusion-associated reactions were reported after 155+ total infusions in all patients
- Treatment-emergent AEs, reported in 11/13 (84%) patients, were generally mild and transient.
- Treatment-related AEs reported in 7/13 (53%) patients: nausea (n=1), fatigue (n=1), headache (n=1), tremor (n=2), acne (n=1), tachycardia (n=1), and hypotension (n=1).

CONCLUSIONS

- ATB200 alone and in combination with miglustat has been safe and well tolerated, with no infusion-associated reactions to date.
- ATB200 alone showed greater-than-dose-proportional increases in exposure, which was further enhanced with miglustat, suggesting a stabilizing effect of chaperone on ATB200.
- After switching from standard of care to ATB200/miglustat, patients generally showed an improvement in biomarkers of muscle damage, with many patients demonstrating normalization by week 18.
- The initial 2 treatment-naive patients treated with ATB200/miglustat demonstrated robust reduction in all biomarkers of muscle damage

```
SEQUENCES
                                              SEQ ID NO: 1
Met Gly Val Arg His Pro Pro Cys Ser His Arg Leu Leu Ala Val Cys

Ala Leu Val Ser Leu Ala Thr Ala Ala Leu Leu Gly His Ile Leu Leu

His Asp Phe Leu Leu Val Pro Arg Glu Leu Ser Gly Ser Ser Pro Val

Leu Glu Glu Thr His Pro Ala His Gln Gln Gly Ala Ser Arg Pro Gly

Pro Arg Asp Ala Gln Ala His Pro Gly Arg Pro Arg Ala Val Pro Thr

Gln Cys Asp Val Pro Pro Asn Ser Arg Phe Asp Cys Ala Pro Asp Lys

Ala Ile Thr Gln Glu Gln Cys Glu Ala Arg Gly Cys Cys Tyr Ile Pro

Ala Lys Gln Gly Leu Gln Gly Ala Gln Met Gly Gln Pro Trp Cys Phe

Phe Pro Pro Ser Tyr Pro Ser Tyr Lys Leu Glu Asn Leu Ser Ser Ser

Glu Met Gly Tyr Thr Ala Thr Leu Thr Arg Thr Thr Pro Thr Phe Phe

Pro Lys Asp Ile Leu Thr Leu Arg Leu Asp Val Met Met Glu Thr Glu

Asn Arg Leu His Phe Thr Ile Lys Asp Pro Ala Asn Arg Arg Tyr Glu

Val Pro Leu Glu Thr Pro Arg Val His Ser Arg Ala Pro Ser Pro Leu

Tyr Ser Val Glu Phe Ser Glu Glu Pro Phe Gly Val Ile Val His Arg

Gln Leu Asp Gly Arg Val Leu Leu Asn Thr Thr Val Ala Pro Leu Phe

Phe Ala Asp Gln Phe Leu Gln Leu Ser Thr Ser Leu Pro Ser Gln Tyr

Ile Thr Gly Leu Ala Glu His Leu Ser Pro Leu Met Leu Ser Thr Ser

Trp Thr Arg Ile Thr Leu Trp Asn Arg Asp Leu Ala Pro Thr Pro Gly

Ala Asn Leu Tyr Gly Ser His Pro Phe Tyr Leu Ala Leu Glu Asp Gly

Gly Ser Ala His Gly Val Phe Leu Leu Asn Ser Asn Ala Met Asp Val

Val Leu Gln Pro Ser Pro Ala Leu Ser Trp Arg Ser Thr Gly Gly Ile

Leu Asp Val Tyr Ile Phe Leu Gly Pro Glu Pro Lys Ser Val Val Gln

Gln Tyr Leu Asp Val Val Gly Tyr Pro Phe Met Pro Pro Tyr Trp Gly

Leu Gly Phe His Leu Cys Arg Trp Gly Tyr Ser Ser Thr Ala Ile Thr

Arg Gln Val Val Glu Asn Met Thr Arg Ala His Phe Pro Leu Asp Val
```

-continued

```
Gln Trp Asn Asp Leu Asp Tyr Met Asp Ser Arg Arg Asp Phe Thr Phe
Asn Lys Asp Gly Phe Arg Asp Phe Pro Ala Met Val Gln Glu Leu His
Gln Gly Gly Arg Arg Tyr Met Met Ile Val Asp Pro Ala Ile Ser Ser
Ser Gly Pro Ala Gly Ser Tyr Arg Pro Tyr Asp Glu Gly Leu Arg Arg
Gly Val Phe Ile Thr Asn Glu Thr Gly Gln Pro Leu Ile Gly Lys Val
Trp Pro Gly Ser Thr Ala Phe Pro Asp Phe Thr Asn Pro Thr Ala Leu
Ala Trp Trp Glu Asp Met Val Ala Glu Phe His Asp Gln Val Pro Phe
Asp Gly Met Trp Ile Asp Met Asn Glu Pro Ser Asn Phe Ile Arg Gly
Ser Glu Asp Gly Cys Pro Asn Asn Glu Leu Glu Asn Pro Pro Tyr Val
Pro Gly Val Val Gly Gly Thr Leu Gln Ala Ala Thr Ile Cys Ala Ser
Ser His Gln Phe Leu Ser Thr His Tyr Asn Leu His Asn Leu Tyr Gly
Leu Thr Glu Ala Ile Ala Ser His Arg Ala Leu Val Lys Ala Arg Gly
Thr Arg Pro Phe Val Ile Ser Arg Ser Thr Phe Ala Gly His Gly Arg
Tyr Ala Gly His Trp Thr Gly Asp Val Trp Ser Ser Trp Glu Gln Leu
Ala Ser Ser Val Pro Glu Ile Leu Gln Phe Asn Leu Leu Gly Val Pro
Leu Val Gly Ala Asp Val Cys Gly Phe Leu Gly Asn Thr Ser Glu Glu
Leu Cys Val Arg Trp Thr Gln Leu Gly Ala Phe Tyr Pro Phe Met Arg
Asn His Asn Ser Leu Leu Ser Leu Pro Gln Glu Pro Tyr Ser Phe Ser
Glu Pro Ala Gln Gln Ala Met Arg Lys Ala Leu Thr Leu Arg Tyr Ala
Leu Leu Pro His Leu Tyr Thr Leu Phe His Gln Ala His Val Ala Gly
Glu Thr Val Ala Arg Pro Leu Phe Leu Glu Phe Pro Lys Asp Ser Ser
Thr Trp Thr Val Asp His Gln Leu Leu Trp Gly Glu Ala Leu Leu Ile
Thr Pro Val Leu Gln Ala Gly Lys Ala Glu Val Thr Gly Tyr Phe Pro
Leu Gly Thr Trp Tyr Asp Leu Gln Thr Val Pro Ile Glu Ala Leu Gly
Ser Leu Pro Pro Pro Ala Ala Pro Arg Glu Pro Ala Ile His Ser
Glu Gly Gln Trp Val Thr Leu Pro Ala Pro Leu Asp Thr Ile Asn Val
His Leu Arg Ala Gly Tyr Ile Ile Pro Leu Gln Gly Pro Gly Leu Thr
Thr Thr Glu Ser Arg Gln Gln Pro Met Ala Leu Ala Val Ala Leu Thr
Lys Gly Gly Glu Ala Arg Gly Glu Leu Phe Trp Asp Asp Gly Glu Ser
Leu Glu Val Leu Glu Arg Gly Ala Tyr Thr Gln Val Ile Phe Leu Ala
Arg Asn Asn Thr Ile Val Asn Glu Leu Val Arg Val Thr Ser Glu Gly
Ala Gly Leu Gln Leu Gln Lys Val Thr Val Leu Gly Val Ala Thr Ala
Pro Gln Gln Val Leu Ser Asn Gly Val Pro Val Ser Asn Phe Thr Tyr
Ser Pro Asp Thr Lys Val Leu Asp Ile Cys Val Ser Leu Leu Met Gly
Glu Gln Phe Leu Val Ser Trp Cys
                                            SEQ ID NO: 2
Gln Gln Gly Ala Ser Arg Pro Gly Pro Arg Asp Ala Gln Ala His Pro
Gly Arg Pro Arg Ala Val Pro Thr Gln Cys Asp Val Pro Pro Asn Ser
Arg Phe Asp Cys Ala Pro Asp Lys Ala Ile Thr Gln Glu Gln Cys Glu
Ala Arg Gly Cys Cys Tyr Ile Pro Ala Lys Gln Gly Leu Gln Gly Ala
Gln Met Gly Gln Pro Trp Cys Phe Phe Pro Pro Ser Tyr Pro Ser Tyr
```

-continued

```
Lys Leu Glu Asn Leu Ser Ser Ser Glu Met Gly Tyr Thr Ala Thr Leu

Thr Arg Thr Thr Pro Thr Phe Phe Pro Lys Asp Ile Leu Thr Leu Arg

Leu Asp Val Met Met Glu Thr Glu Asn Arg Leu His Phe Thr Ile Lys

Asp Pro Ala Asn Arg Arg Tyr Glu Val Pro Leu Glu Thr Pro Arg Val

His Ser Arg Ala Pro Ser Pro Leu Tyr Ser Val Glu Phe Ser Glu Glu

Pro Phe Gly Val Ile Val His Arg Gln Leu Asp Gly Arg Val Leu Leu

Asn Thr Thr Val Ala Pro Leu Phe Phe Ala Asp Gln Phe Leu Gln Leu

Ser Thr Ser Leu Pro Ser Gln Tyr Ile Thr Gly Leu Ala Glu His Leu

Ser Pro Leu Met Leu Ser Thr Ser Trp Thr Arg Ile Thr Leu Trp Asn

Arg Asp Leu Ala Pro Thr Pro Gly Ala Asn Leu Tyr Gly Ser His Pro

Phe Tyr Leu Ala Leu Glu Asp Gly Gly Ser Ala His Gly Val Phe Leu

Leu Asn Ser Asn Ala Met Asp Val Val Leu Gln Pro Ser Pro Ala Leu

Ser Trp Arg Ser Thr Gly Gly Ile Leu Asp Val Tyr Ile Phe Leu Gly

Pro Glu Pro Lys Ser Val Val Gln Gln Tyr Leu Asp Val Val Gly Tyr

Pro Phe Met Pro Pro Tyr Trp Gly Leu Gly Phe His Leu Cys Arg Trp

Gly Tyr Ser Ser Thr Ala Ile Thr Arg Gln Val Val Glu Asn Met Thr

Arg Ala His Phe Pro Leu Asp Val Gln Trp Asn Asp Leu Asp Tyr Met

Asp Ser Arg Arg Asp Phe Thr Phe Asn Lys Asp Gly Phe Arg Asp Phe

Pro Ala Met Val Gln Glu Leu His Gln Gly Gly Arg Arg Tyr Met Met

Ile Val Asp Pro Ala Ile Ser Ser Ser Gly Pro Ala Gly Ser Tyr Arg

Pro Tyr Asp Glu Gly Leu Arg Arg Gly Val Phe Ile Thr Asn Glu Thr

Gly Gln Pro Leu Ile Gly Lys Val Trp Pro Gly Ser Thr Ala Phe Pro

Asp Phe Thr Asn Pro Thr Ala Leu Ala Trp Trp Glu Asp Met Val Ala

Glu Phe His Asp Gln Val Pro Phe Asp Gly Met Trp Ile Asp Met Asn

Glu Pro Ser Asn Phe Ile Arg Gly Ser Glu Asp Gly Cys Pro Asn Asn

Glu Leu Glu Asn Pro Pro Tyr Val Pro Gly Val Val Gly Gly Thr Leu

Gln Ala Ala Thr Ile Cys Ala Ser Ser His Gln Phe Leu Ser Thr His

Tyr Asn Leu His Asn Leu Tyr Gly Leu Thr Glu Ala Ile Ala Ser His

Arg Ala Leu Val Lys Ala Arg Gly Thr Arg Pro Phe Val Ile Ser Arg

Ser Thr Phe Ala Gly His Gly Arg Tyr Ala Gly His Trp Thr Gly Asp

Val Trp Ser Ser Trp Glu Gln Leu Ala Ser Ser Val Pro Glu Ile Leu

Gln Phe Asn Leu Leu Gly Val Pro Leu Val Gly Ala Asp Val Cys Gly

Phe Leu Gly Asn Thr Ser Glu Glu Leu Cys Val Arg Trp Thr Gln Leu

Gly Ala Phe Tyr Pro Phe Met Arg Asn His Asn Ser Leu Leu Ser Leu

Pro Gln Glu Pro Tyr Ser Phe Ser Glu Pro Ala Gln Gln Ala Met Arg

Lys Ala Leu Thr Leu Arg Tyr Ala Leu Leu Pro His Leu Tyr Thr Leu

Phe His Gln Ala His Val Ala Gly Glu Thr Val Ala Arg Pro Leu Phe

Leu Glu Phe Pro Lys Asp Ser Ser Thr Trp Thr Val Asp His Gln Leu

Leu Trp Gly Glu Ala Leu Leu Ile Thr Pro Val Leu Gln Ala Gly Lys

Ala Glu Val Thr Gly Tyr Phe Pro Leu Gly Thr Trp Tyr Asp Leu Gln
```

-continued

```
Thr Val Pro Ile Glu Ala Leu Gly Ser Leu Pro Pro Pro Ala Ala

Pro Arg Glu Pro Ala Ile His Ser Glu Gly Gln Trp Val Thr Leu Pro

Ala Pro Leu Asp Thr Ile Asn Val His Leu Arg Ala Gly Tyr Ile Ile

Pro Leu Gln Gly Pro Gly Leu Thr Thr Thr Glu Ser Arg Gln Gln Pro

Met Ala Leu Ala Val Ala Leu Thr Lys Gly Gly Glu Ala Arg Gly Glu

Leu Phe Trp Asp Asp Gly Glu Ser Leu Glu Val Leu Glu Arg Gly Ala

Tyr Thr Gln Val Ile Phe Leu Ala Arg Asn Asn Thr Ile Val Asn Glu

Leu Val Arg Val Thr Ser Glu Gly Ala Gly Leu Gln Leu Gln Lys Val

Thr Val Leu Gly Val Ala Thr Ala Pro Gln Gln Val Leu Ser Asn Gly

Val Pro Val Ser Asn Phe Thr Tyr Ser Pro Asp Thr Lys Val Leu Asp

Ile Cys Val Ser Leu Leu Met Gly Glu Gln Phe Leu Val Ser Trp Cys
```

What is claimed is:

1. A pharmaceutical formulation comprising:
   (a) a population of recombinant human acid α-glucosidase (rhGAA) molecules, wherein the rhGAA molecules are expressed in Chinese hamster ovary (CHO) cells and comprise a first, second, third, fourth, fifth, sixth, and seventh potential N-glycosylation site at amino acids corresponding to N84, N177, N334, N414, N596, N826, and N869 of SEQ ID NO:2, respectively, wherein 40%-60% of the N-glycans on the rhGAA molecules are complex type N-glycans, and wherein at least 50% of the rhGAA molecules comprise a glycan bearing bis-mannose-6-phosphate (bis-M6P) at the first potential N-glycosylation site;
   (b) a citrate buffer, and
   (c) at least one excipient selected from the group consisting of mannitol, polysorbate 80, and combinations thereof,
   wherein the formulation has a pH of from about 5.0 to about 7.0.

2. The pharmaceutical formulation of claim 1, wherein the rhGAA molecules are present in a concentration of about 5 mg/mL to about 50 mg/mL.

3. The pharmaceutical formulation of claim 2, wherein the rhGAA molecules are present in a concentration of about 15 mg/mL.

4. The pharmaceutical formulation of claim 1, wherein the formulation has a pH of from about 5.5 to about 7.0.

5. The pharmaceutical formulation of claim 4, wherein the formulation has a pH of about 6.0.

6. The pharmaceutical formulation of claim 1, wherein the citrate buffer comprises a potassium, sodium, or ammonium salt.

7. The pharmaceutical formulation of claim 1, wherein the citrate buffer comprises sodium citrate.

8. The pharmaceutical formulation of claim 1, wherein the citrate buffer is present in a concentration of about 10 mM to about 100 mM.

9. The pharmaceutical formulation of claim 8, wherein the citrate buffer is present in a concentration of about 25 mM.

10. The pharmaceutical formulation of claim 1, wherein trehalose, sucrose, glycine, or combinations thereof is excluded.

11. The pharmaceutical formulation of claim 1, wherein the at least one excipient is mannitol present in a concentration of about 10 mg/mL to about 50 mg/mL.

12. The pharmaceutical formulation of claim 1, wherein the at least one excipient is polysorbate 80 present in a concentration of about 0.2 mg/mL to about 0.5 mg/mL.

13. The pharmaceutical formulation of claim 1, wherein the at least one excipient comprises mannitol and polysorbate 80, and wherein the mannitol is present at a concentration of about 20 mg/mL and the polysorbate 80 is present at a concentration of about 0.5 mg/mL.

14. The pharmaceutical formulation of claim 1, further comprising:
   (a) an alkalizing agent; and/or
   (b) an acidifying agent,
   wherein the alkalizing agent and/or acidifying agent are present in amounts to maintain the pharmaceutical formulation at a pH of from about 5.0 to about 6.0.

15. The pharmaceutical formulation of claim 1, wherein at least 75% of the rhGAA molecules comprise a glycan bearing bis-M6P at the first potential N-glycosylation site.

16. The pharmaceutical formulation of claim 1, wherein the rhGAA molecules comprise from about 3.0 mol to about 5.0 mol mannose-6-phosphate (M6P) residues per mol rhGAA.

17. The pharmaceutical formulation of claim 1, wherein the rhGAA molecules comprise at least 3 mol M6P residues per mole of and at least 4 of mol sialic acid residues per mole rhGAA.

18. The pharmaceutical formulation of claim 1, wherein 75% to about 80% of the rhGAA molecules comprise a glycan bearing bis-M6P at the first potential N-glycosylation site, about 40% to about 60% of the rhGAA molecules comprise a glycan bearing mono-mannose-6-phosphate (mono-M6P) at the second potential N-glycosylation site, about 40% to about 60% of the rhGAA molecules comprise a glycan bearing bis-M6P at the fourth potential N-glycosylation site, and about 25% to about 40% of the rhGAA molecules comprise a glycan bearing mono-M6P at the fourth potential N-glycosylation site.

19. The pharmaceutical formulation of claim 1, wherein the pharmaceutical formulation consists essentially of:
   (a) the population of rhGAA molecules;
   (b) sodium citrate;
   (c) citric acid monohydrate;
   (d) mannitol;
   (e) polysorbate 80;
   (f) water;
   (g) optionally, an acidifying agent; and
   (h) optionally, an alkalizing agent,
   wherein the formulation has a pH of from about 5.0 to about 6.0.

20. The pharmaceutical formulation of claim 1, wherein the pharmaceutical formulation consists essentially of:
   (a) the population of rhGAA molecules, present at a concentration of about 15 mg/mL;
   (b) sodium citrate buffer, present at a concentration of about 25 mM;
   (c) mannitol, present at a concentration of about 20 mg/mL;
   (d) polysorbate 80, present at a concentration of about 0.5 mg/mL; and
   (e) water;
   (f) optionally, an acidifying agent; and
   (g) optionally, an alkalizing agent,
   wherein the formulation has a pH of from about 5.0 to about 6.0.

21. A pharmaceutical composition comprising the formulation of claim 1 after lyophilization.

22. A method of treating Pompe disease comprising administering to a patient in need thereof the pharmaceutical formulation of claim 1.

23. The method of claim 22, further comprising diluting the pharmaceutical formulation prior to administration to the patient.

* * * * *

SEQUENCE LISTING

<160> NUMBER OF SEQ ID NOS: 2

<210> SEQ ID NO 1
<211> LENGTH: 952
<212> TYPE: PRT
<213> ORGANISM: Homo sapiens

<400> SEQUENCE: 1

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
        50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
                100                 105                 110

Ala Lys Gln Gly Leu Gln Gly Ala Gln Met Gly Gln Pro Trp Cys Phe
            115                 120                 125

Phe Pro Pro Ser Tyr Pro Ser Tyr Lys Leu Glu Asn Leu Ser Ser Ser
        130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240
```

```
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
                260                 265                 270
Trp Thr Arg Ile Thr Leu Trp Asn Arg Asp Leu Ala Pro Thr Pro Gly
                275                 280                 285
Ala Asn Leu Tyr Gly Ser His Pro Phe Tyr Leu Ala Leu Glu Asp Gly
                290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
                340                 345                 350
Gln Tyr Leu Asp Val Val Gly Tyr Pro Phe Met Pro Pro Tyr Trp Gly
                355                 360                 365
Leu Gly Phe His Leu Cys Arg Trp Gly Tyr Ser Ser Thr Ala Ile Thr
                370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
                420                 425                 430
Gln Gly Gly Arg Arg Tyr Met Met Ile Val Asp Pro Ala Ile Ser Ser
                435                 440                 445
Ser Gly Pro Ala Gly Ser Tyr Arg Pro Tyr Asp Glu Gly Leu Arg Arg
450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
                500                 505                 510
Asp Gly Met Trp Ile Asp Met Asn Glu Pro Ser Asn Phe Ile Arg Gly
                515                 520                 525
Ser Glu Asp Gly Cys Pro Asn Asn Glu Leu Glu Asn Pro Pro Tyr Val
                530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
                580                 585                 590
Thr Arg Pro Phe Val Ile Ser Arg Ser Thr Phe Ala Gly His Gly Arg
                595                 600                 605
Tyr Ala Gly His Trp Thr Gly Asp Val Trp Ser Ser Trp Glu Gln Leu
                610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
```

```
Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
            805                 810                 815

His Leu Arg Ala Gly Tyr Ile Ile Pro Leu Gln Gly Pro Gly Leu Thr
        820                 825                 830

Thr Thr Glu Ser Arg Gln Gln Pro Met Ala Leu Ala Val Ala Leu Thr
835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
            885                 890                 895

Ala Gly Leu Gln Leu Gln Lys Val Thr Val Leu Gly Val Ala Thr Ala
        900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 2
<211> LENGTH: 896
<212> TYPE: PRT
<213> ORGANISM: Homo sapiens

<400> SEQUENCE: 2

Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Pro Ser Tyr Pro Ser Tyr
65              70                  75                  80
```

-continued

```
Lys Leu Glu Asn Leu Ser Ser Ser Glu Met Gly Tyr Thr Ala Thr Leu
                 85                  90                  95
Thr Arg Thr Thr Pro Thr Phe Phe Pro Lys Asp Ile Leu Thr Leu Arg
            100                 105                 110
Leu Asp Val Met Met Glu Thr Glu Asn Arg Leu His Phe Thr Ile Lys
            115                 120                 125
Asp Pro Ala Asn Arg Arg Tyr Glu Val Pro Leu Glu Thr Pro Arg Val
130                 135                 140
His Ser Arg Ala Pro Ser Pro Leu Tyr Ser Val Glu Phe Ser Glu Glu
145                 150                 155                 160
Pro Phe Gly Val Ile Val His Arg Gln Leu Asp Gly Arg Val Leu Leu
                165                 170                 175
Asn Thr Thr Val Ala Pro Leu Phe Phe Ala Asp Gln Phe Leu Gln Leu
            180                 185                 190
Ser Thr Ser Leu Pro Ser Gln Tyr Ile Thr Gly Leu Ala Glu His Leu
            195                 200                 205
Ser Pro Leu Met Leu Ser Thr Ser Trp Thr Arg Ile Thr Leu Trp Asn
            210                 215                 220
Arg Asp Leu Ala Pro Thr Pro Gly Ala Asn Leu Tyr Gly Ser His Pro
225                 230                 235                 240
Phe Tyr Leu Ala Leu Glu Asp Gly Gly Ser Ala His Gly Val Phe Leu
                245                 250                 255
Leu Asn Ser Asn Ala Met Asp Val Val Leu Gln Pro Ser Pro Ala Leu
            260                 265                 270
Ser Trp Arg Ser Thr Gly Gly Ile Leu Asp Val Tyr Ile Phe Leu Gly
            275                 280                 285
Pro Glu Pro Lys Ser Val Val Gln Gln Tyr Leu Asp Val Val Gly Tyr
290                 295                 300
Pro Phe Met Pro Pro Tyr Trp Gly Leu Gly Phe His Leu Cys Arg Trp
305                 310                 315                 320
Gly Tyr Ser Ser Thr Ala Ile Thr Arg Gln Val Val Glu Asn Met Thr
                325                 330                 335
Arg Ala His Phe Pro Leu Asp Val Gln Trp Asn Asp Leu Asp Tyr Met
                340                 345                 350
Asp Ser Arg Arg Asp Phe Thr Phe Asn Lys Asp Gly Phe Arg Asp Phe
            355                 360                 365
Pro Ala Met Val Gln Glu Leu His Gln Gly Gly Arg Arg Tyr Met Met
            370                 375                 380
Ile Val Asp Pro Ala Ile Ser Ser Ser Gly Pro Ala Gly Ser Tyr Arg
385                 390                 395                 400
Pro Tyr Asp Glu Gly Leu Arg Arg Gly Val Phe Ile Thr Asn Glu Thr
                405                 410                 415
Gly Gln Pro Leu Ile Gly Lys Val Trp Pro Gly Ser Thr Ala Phe Pro
            420                 425                 430
Asp Phe Thr Asn Pro Thr Ala Leu Ala Trp Trp Glu Asp Met Val Ala
            435                 440                 445
Glu Phe His Asp Gln Val Pro Phe Asp Gly Met Trp Ile Asp Met Asn
            450                 455                 460
Glu Pro Ser Asn Phe Ile Arg Gly Ser Glu Asp Gly Cys Pro Asn Asn
465                 470                 475                 480
Glu Leu Glu Asn Pro Pro Tyr Val Pro Gly Val Val Gly Gly Thr Leu
                485                 490                 495
```

```
Gln Ala Ala Thr Ile Cys Ala Ser Ser His Gln Phe Leu Ser Thr His
                500                 505                 510
Tyr Asn Leu His Asn Leu Tyr Gly Leu Thr Glu Ala Ile Ala Ser His
            515                 520                 525
Arg Ala Leu Val Lys Ala Arg Gly Thr Arg Pro Phe Val Ile Ser Arg
        530                 535                 540
Ser Thr Phe Ala Gly His Gly Arg Tyr Ala Gly His Trp Thr Gly Asp
545                 550                 555                 560
Val Trp Ser Ser Trp Glu Gln Leu Ala Ser Val Pro Glu Ile Leu
                565                 570                 575
Gln Phe Asn Leu Leu Gly Val Pro Leu Val Gly Ala Asp Val Cys Gly
                580                 585                 590
Phe Leu Gly Asn Thr Ser Glu Glu Leu Cys Val Arg Trp Thr Gln Leu
                595                 600                 605
Gly Ala Phe Tyr Pro Phe Met Arg Asn His Asn Ser Leu Leu Ser Leu
                610                 615                 620
Pro Gln Glu Pro Tyr Ser Phe Ser Glu Pro Ala Gln Gln Ala Met Arg
625                 630                 635                 640
Lys Ala Leu Thr Leu Arg Tyr Ala Leu Leu Pro His Leu Tyr Thr Leu
                645                 650                 655
Phe His Gln Ala His Val Ala Gly Glu Thr Val Ala Arg Pro Leu Phe
                660                 665                 670
Leu Glu Phe Pro Lys Asp Ser Ser Thr Trp Thr Val Asp His Gln Leu
                675                 680                 685
Leu Trp Gly Glu Ala Leu Leu Ile Thr Pro Val Leu Gln Ala Gly Lys
                690                 695                 700
Ala Glu Val Thr Gly Tyr Phe Pro Leu Gly Thr Trp Tyr Asp Leu Gln
705                 710                 715                 720
Thr Val Pro Ile Glu Ala Leu Gly Ser Leu Pro Pro Pro Ala Ala
                725                 730                 735
Pro Arg Glu Pro Ala Ile His Ser Glu Gly Gln Trp Val Thr Leu Pro
                740                 745                 750
Ala Pro Leu Asp Thr Ile Asn Val His Leu Arg Ala Gly Tyr Ile Ile
                755                 760                 765
Pro Leu Gln Gly Pro Gly Leu Thr Thr Thr Glu Ser Arg Gln Gln Pro
                770                 775                 780
Met Ala Leu Ala Val Ala Leu Thr Lys Gly Gly Glu Ala Arg Gly Glu
785                 790                 795                 800
Leu Phe Trp Asp Asp Gly Glu Ser Leu Glu Val Leu Glu Arg Gly Ala
                805                 810                 815
Tyr Thr Gln Val Ile Phe Leu Ala Arg Asn Asn Thr Ile Val Asn Glu
                820                 825                 830
Leu Val Arg Val Thr Ser Glu Gly Ala Gly Leu Gln Leu Gln Lys Val
                835                 840                 845
Thr Val Leu Gly Val Ala Thr Ala Pro Gln Gln Val Leu Ser Asn Gly
                850                 855                 860
Val Pro Val Ser Asn Phe Thr Tyr Ser Pro Asp Thr Lys Val Leu Asp
865                 870                 875                 880
Ile Cys Val Ser Leu Leu Met Gly Glu Gln Phe Leu Val Ser Trp Cys
                885                 890                 895
```